United States Patent
Shi et al.

(10) Patent No.: US 8,927,509 B2
(45) Date of Patent: Jan. 6, 2015

(54) APTAMER MODULATORS OF COMPLEMENT PROTEIN C3 AND BIOLOGICALLY ACTIVE PROTEOLYTIC PRODUCTS THEREOF

(75) Inventors: Hua Shi, Ithaca, NY (US); Albert J. T. Millis, Schenectady, NY (US); Kimi Nishikawa, Greenwich, NY (US); Prabhat Kumar Mallik, Watervliet, NY (US)

(73) Assignee: The Research Foundation of State University of New York, Albany, NY (US)

( * ) Notice: Subject to any disclaimer, the term of this patent is extended or adjusted under 35 U.S.C. 154(b) by 498 days.

(21) Appl. No.: 12/469,483

(22) Filed: May 20, 2009

(65) Prior Publication Data

US 2012/0141382 A1 Jun. 7, 2012

Related U.S. Application Data

(60) Provisional application No. 61/054,717, filed on May 20, 2008.

(51) Int. Cl.

| | | |
|---|---|---|
| *A01N 43/04* | (2006.01) | |
| *A61K 31/70* | (2006.01) | |
| *C07H 21/02* | (2006.01) | |
| *A61K 49/18* | (2006.01) | |
| *A61K 31/7088* | (2006.01) | |
| *A61K 41/00* | (2006.01) | |
| *B82Y 5/00* | (2011.01) | |
| *C12N 15/115* | (2010.01) | |

(52) U.S. Cl.
CPC ......... *A61K 49/1872* (2013.01); *A61K 31/7088* (2013.01); *A61K 41/0052* (2013.01); *A61K 49/1809* (2013.01); *A61K 49/1863* (2013.01); *B82Y 5/00* (2013.01); *C12N 15/115* (2013.01); *C12N 2310/16* (2013.01)
USPC ....................................... 514/44 R; 536/23.1

(58) Field of Classification Search
CPC combination set(s) only.
See application file for complete search history.

(56) References Cited

U.S. PATENT DOCUMENTS

| | | | |
|---|---|---|---|
| 6,458,559 B1 | 10/2002 | Shi et al. | |
| 6,566,343 B2 * | 5/2003 | Biesecker et al. | 514/44 R |
| 2004/0053310 A1 | 3/2004 | Shi et al. | |
| 2005/0282190 A1 | 12/2005 | Shi et al. | |

FOREIGN PATENT DOCUMENTS

| | | |
|---|---|---|
| WO | 9742317 A1 | 11/1997 |
| WO | 2006096754 A2 | 9/2006 |
| WO | 2006133271 A2 | 12/2006 |

OTHER PUBLICATIONS

Yefenof, et al. (1990) The Journal of Immunology, v.144(4):1538-43, "Potentiation of NK Cytotoxicity by Antibody-C3b/iC3b Heteroconjugates."*
Bao et al., "Administration of a Soluble Recombinant Complement C3 Inhibitor Protects Against Renal Disease in MRL/lpr Mice," J. Am. Soc. Nephrol. 14:670-679 (2003).
Carrasquillo et al., "Controlled Delivery of the Anti-VEGF Aptamer EYE001 with Poly(lactic-co-glycolic)Acid Microspheres," IOVS 44(1):290-299 (2003).
Lee et al., "A Therapeutic Aptamer Inhibits Angiogenesis by Specifically Targeting the Heparin Binding Domain of Vegf165," PNAS 102(52):18902-18907 (2005).
Farokhzad et al., "Nanoparticle-Aptamer Bioconjugates: A New Approach for Targeting Prostate Cancer Cells," Cancer Research 64:7668-7672 (2004).
Chu et al., "Aptamer Mediated siRNA Delivery," Nucleic Acids Research 34(10):e73:1-6 (2006).
Lupold et al., "Identification and Characterization of Nuclease-Stabilized RNA Molecules that Bind Human Prostate Cancer Cells via the Prostate-Specific Membrane Antigen," Cancer Research, 62:4029-4033 (2002).
Shangguan et al., "Aptamers Evolved from Live Cells as Effective Molecular Probes for Cancer Study," PNAS 103 (32):11838-11843 (2006).
Shangguan et al., "Aptamers Evolved from Cultured Cancer Cells Reveal Molecular differences of Cancer Cells in Patient Samples," Clinical Chemistry 53(6):1153-1155 (2007).
Mallikaratchy et al., "Aptamer Directly Evolved from Live Cells Recognizes Membrane Bound Immunoglobin Heavy Mu Chain in Burkitt's Lymphoma Cells," Molecular & Cellular Proteomics 6(12):2230-2238 (2007).
Chen et al., "Inhibition of Heregulin Signaling by an Aptamer that Preferentially Binds to the Oligomeric Form of Human Epidermal Growth Factor Receptor-3," PNAS 100(16):9226-9231 (2003).
Shangguan et al., "Identification of Liver Cancer-Specific Aptamers Using Whole Live Cells," Anal. Chem. 80 (3):721-728 (2008) Abstract Only.
Nimjee et al., "Aptamers: An emerging Class of Therapeutics," Annu. Rev. Med. 56:555-583 (2005).
Pestourie et al., "Aptamers Against Extracellular Targets for In Vivo Applications," Biochimie 2405:1-10 (2005).

* cited by examiner

*Primary Examiner* — Jennifer McDonald
(74) *Attorney, Agent, or Firm* — LeClairRyan, a Professional Corporation

(57) ABSTRACT

This invention relates to nucleic acid aptamers that recognize and bind the complement protein C3 or its biologically active proteolytic products and methods of their use. Particularly preferred are bi-functional aptamer construct that binding specifically with C3b or iC3b, and another target protein. Use of these molecular constructs for commandeering the opsonization process is also described herein.

20 Claims, 12 Drawing Sheets

SEQUENCE LISTING

<160> NUMBER OF SEQ ID NOS: 21

<210> SEQ ID NO 1
<211> LENGTH: 108
<212> TYPE: DNA
<213> ORGANISM: Artificial
<220> FEATURE:
<223> OTHER INFORMATION: aptamer template "Temp50"
<220> FEATURE:
<221> NAME/KEY: misc_feature
<222> LOCATION: (26)..(75)
<223> OTHER INFORMATION: n is a, c, g, or t

<400> SEQUENCE: 1
accgagtcca gaagcttgta gtactnnnnn nnnnnnnnnn nnnnnnnnnn nnnnnnnnnn          60
nnnnnnnnnn nnnnngccta gatggcagtt gaattctccc tatagtga                     108

<210> SEQ ID NO 2
<211> LENGTH: 40
<212> TYPE: DNA
<213> ORGANISM: Artificial
<220> FEATURE:
<223> OTHER INFORMATION: primer "ForT7"

<400> SEQUENCE: 2
gtaatacgac tcactatagg gagaattcaa ctgccatcta                               40

<210> SEQ ID NO 3
<211> LENGTH: 22
<212> TYPE: DNA
<213> ORGANISM: Artificial
<220> FEATURE:
<223> OTHER INFORMATION: primer "RevUniv"

<400> SEQUENCE: 3
accgagtcca gaagcttgta gt                                                  22

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
ccgagtccag aagcttgtag t                                                   21

<210> SEQ ID NO 5
<211> LENGTH: 100
<212> TYPE: RNA
<213> ORGANISM: Artificial
<220> FEATURE:
<223> OTHER INFORMATION: Aptamer "AptC3-1"

<400> SEQUENCE: 5
gggagaauuc aacugccauc uaggcuagaa gaauaugacg gauugaccgu aucaggguag  60
ccgaagggag acagaaguac uacaagcuuc uggacucggu  100

<210> SEQ ID NO 6
<211> LENGTH: 100
<212> TYPE: RNA
<213> ORGANISM: Artificial
<220> FEATURE:
<223> OTHER INFORMATION: Aptamer "AptC3-2"

<400> SEQUENCE: 6
gggagaauuc aacugccauc uaggcaaauc cgcgagcgcc gguaccggug gcgcaugccc  60
acacagcacu aaacgaguac uacaagcuuc uggacucggu  100

<210> SEQ ID NO 7
<211> LENGTH: 37
<212> TYPE: DNA
<213> ORGANISM: Artificial
<220> FEATURE:
<223> OTHER INFORMATION: primer

<400> SEQUENCE: 7
gtaatacgac tcactatagg gctagaagaa tatgacg  37

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
cggctaccct gatacggtc  19

<210> SEQ ID NO 9
<211> LENGTH: 42
<212> TYPE: RNA
<213> ORGANISM: Artificial
<220> FEATURE:
<223> OTHER INFORMATION: Aptamer "MiniAptC3-1"

<400> SEQUENCE: 9
gggcuagaag aauaugacgg auugaccgua ucaggguagc cg  42

<210> SEQ ID NO 10
<211> LENGTH: 40
<212> TYPE: DNA
<213> ORGANISM: Artificial
<220> FEATURE:
<223> OTHER INFORMATION: primer

<400> SEQUENCE: 10
gtaatacgac tcactatagg gagaattcaa ctgccatcta  40

<210> SEQ ID NO 11
<211> LENGTH: 17
<212> TYPE: DNA
<213> ORGANISM: Artificial
<220> FEATURE:
<223> OTHER INFORMATION: primer

<400> SEQUENCE: 11
gggcatgcgc caccggt  17

<210> SEQ ID NO 12
<211> LENGTH: 60
<212> TYPE: RNA
<213> ORGANISM: Artificial
<220> FEATURE:
<223> OTHER INFORMATION: Minimization derivative of AptC3-2

<400> SEQUENCE: 12
gggagaauuc aacugccauc uaggcaaauc cgcgagcgcc gguaccggug gcgcaugccc    60

<210> SEQ ID NO 13
<211> LENGTH: 107
<212> TYPE: RNA
<213> ORGANISM: Artificial
<220> FEATURE:
<223> OTHER INFORMATION: AptGFP-AP3

<400> SEQUENCE: 13
gcgugagacg ucuugaugaa auccggcucg gcaaugguuc guggcgaauu ggguggggaa    60
aguccuuaaa agagggccac cacagaagcu guggaguua acagcaa                  107

<210> SEQ ID NO 14
<211> LENGTH: 134
<212> TYPE: RNA
<213> ORGANISM: Artificial
<220> FEATURE:
<223> OTHER INFORMATION: Type A1 aptamer Apt[C3-GFP]

<400> SEQUENCE: 14
gggagccuga uggcagggcg aauugggugg ggaaaguccu uaaaagaggg ccaccacaga    60
agcaaugggc uucuggacuc gguccegcuc ggcuagaaga auaugacgga uugaccguau   120
caggguagcc gagc                                                     134

<210> SEQ ID NO 15
<211> LENGTH: 97
<212> TYPE: DNA
<213> ORGANISM: Artificial
<220> FEATURE:
<223> OTHER INFORMATION: primer

<400> SEQUENCE: 15
gtaatacgac tcactatagg gagcctgatg gcagggcgaa ttgggtgggg aaagtcctta    60
aaagagggcc accacagaag caatgggctt ctggact                            97

<210> SEQ ID NO 16
<211> LENGTH: 76
<212> TYPE: DNA
<213> ORGANISM: Artificial
<220> FEATURE:
<223> OTHER INFORMATION: primer

<400> SEQUENCE: 16
gctcggctac cctgatacgg tcaatccgtc atattcttct agccgagcgg gaccgagtcc    60
agaagcccat tgcttc                                                   76

<210> SEQ ID NO 17
<211> LENGTH: 141
<212> TYPE: RNA
<213> ORGANISM: Artificial
<220> FEATURE:
<223> OTHER INFORMATION: Type A2 Aptamer

<400> SEQUENCE: 17

```
gggagccuga uggcagggcg aauugggugg ggaaaguccu uaaaagaggg ccaccacaga      60 agcaauggg  uucuggacuc ggucccuuuu uuugcucggc uagaagaaua ugacggauug     120
accguaucag gguagccgag c                                                141
```

<210> SEQ ID NO 18
<211> LENGTH: 83
<212> TYPE: DNA
<213> ORGANISM: Artificial
<220> FEATURE:
<223> OTHER INFORMATION: primer

<400> SEQUENCE: 18

```
gctcggctac cctgatacgg tcaatccgtc atattcttct agccgagcaa aaaagggac      60 cgagtccaga agcccattgc ttc                                              83
```

<210> SEQ ID NO 19
<211> LENGTH: 129
<212> TYPE: RNA
<213> ORGANISM: Artificial
<220> FEATURE:
<223> OTHER INFORMATION: Type B1 Aptamer

<400> SEQUENCE: 19

```
gggcuucugg acucgcccug auggcagggc gaauugggug gggaaagucc uuaaaagagg      60
gccaccacag aagcccuuuu uuucucggcu agaagaauau gacggauuga ccguaucagg     120
guagccgag                                                              129
```

<210> SEQ ID NO 20
<211> LENGTH: 90
<212> TYPE: DNA
<213> ORGANISM: Artificial
<220> FEATURE:
<223> OTHER INFORMATION: primer

<400> SEQUENCE: 20

```
gtaatacgac tcactatagg gcttctggac tcgccctgat ggcagggcga attgggtggg      60
gaaagtcctt aaaagagggc caccacagaa                                       90
```

<210> SEQ ID NO 21
<211> LENGTH: 77
<212> TYPE: DNA
<213> ORGANISM: Artificial
<220> FEATURE:
<223> OTHER INFORMATION: primer

<400> SEQUENCE: 21

```
ctcggctacc ctgatacggt caatccgtca tattcttcta gccgagaaaa aagggcttc      60 tgtggtggcc ctctttt                                                     77
```

APTAMER MODULATORS OF COMPLEMENT PROTEIN C3 AND BIOLOGICALLY ACTIVE PROTEOLYTIC PRODUCTS THEREOF

This application claims the priority benefit of U.S. Provisional Patent Application Ser. No. 61/054,717, filed May 20, 2008, which is hereby incorporated by reference in its entirety.

This invention was made with government support under grant number W81XWH-06-1-0599 awarded by the U.S. Army Medical Research and Materiel Command. The government has certain rights in the invention.

FIELD OF THE INVENTION

This invention relates to nucleic acid aptamers that recognize and bind the complement protein C3 or its biologically active proteolytic products and methods of their use.

BACKGROUND OF THE INVENTION

The human complement system constitutes an important part of innate immunity, which has three major physiological activities (Walport, "Complement. First of two parts," *New Engl. J. Med.* 344:1058-1066 (2001) Walport, "Complement. Second of two parts," *New Engl. J. Med.* 344:1140-1144 (2001)). First, it defends the host against bacterial infections through opsonization (a process that makes antigens more susceptible to phagocytosis), activation of leukocytes, and lysis of bacterial cells. Second, it connects innate and acquired immunity by augmenting antibody response and enhancing immunologic memory. Third, it disposes of waste from tissue such as immune complexes, apoptotic cells, and products of inflammatory injury. The complement system has about 35 cell surface and soluble plasma proteins. In plasma, they amount to more than 3 g per liter and constitute approximately 15% of the globulin fraction. These proteins are synthesized mainly in the liver.

The complement system is activated through three pathways, all of them leading to the generation of the homologous variants of the protease C3-convertase (Walport, "Complement. First of two parts," *New Engl. J. Med.* 344:1058-1066 (2001); Walport, "Complement. Second of two parts," *New Engl. J. Med.* 344:1140-1144 (2001)). As shown in FIG. 1, the classical complement pathway typically requires antibodies for initiation, while the alternate pathway can be activated by spontaneous C3 hydrolysis ("tickover") without the presence of antibodies. The mannose-binding lectin pathway belongs to the non-specific immune response as well. C3-convertase cleaves and activates component C3, creating C3a and C3b and causing a cascade of further cleavage and activation events. C3b binding to the surface of pathogens (opsonization) leads to recognition by C3 receptors, such as CR1 or CR3 on phagocytic cells, which enhances the engulfment of the opsonized particles. C5b initiates the membrane attack pathway, which results in formation of the membrane attack complex ("MAC"), including C5b, C6, C7, C8, and polymeric C9. In addition to these two major effector mechanisms (opsonization and the formation of the MAC), there are other effects of complement activation. For example, C5a is an important chemotactic factor that helps recruit inflammatory cells. Both C3a and C5a have anaphylatoxin activity, which results in mast cell degranulation, increased vascular permeability, smooth muscle contraction, etc.

The complement system emerged about 600-700 million years ago and over the course of evolution it has been endowed with a wide range of functions. Unlike components involved in acquired immunity, complement proteins do not have the intrinsic capability to discriminate between self and non-self antigens, and have the potential to damage or destroy any particles (molecules, supramolecular assemblies, or cells) to which they bind. Therefore, in addition to its role in immune defense, the complement system contributes to tissue damage in many clinical conditions. As a means of preventing homologous attack, the complement system is tightly regulated by a group of proteins called regulators of complement activation ("RCA"), and host cell damage is often the consequence of unregulated complement activation. While complement activation is not an etiological factor in any known disease, it may play an essential role in the pathogenesis of many diseases. Tissue injury can be caused directly by MAC or indirectly by the generation of the anaphylatoxic peptides C3a and C5a.

Complement has been implicated in numerous infectious, allergic, biocompatibility, shock, rheumatological, renal, hematological, dermatological, neurological, and vascular/pulmonary diseases and disorders. Therefore, there is a pressing need for effective complement inhibitors to prevent and treat these disease states (Sahu et al., "Complement Inhibitors: A Resurgent Concept in Anti-Inflammatory Therapeutics," *Immunopharmacology* 49:133-148 (2000)). Ideally, the choice of complement protein or proteins as drug targets should be made according to the specific pathological condition of interest. Following this logic, complement inhibitors have been developed for a few targets. However, in most clinical conditions, it is difficult to determine which pathway initiated the activation, and activation of one pathway often leads to the recruitment of another. Therefore, a complement inhibitor that blocks all three pathways would be useful. Because all three pathways converge at the C3 activation step, blocking this step would inhibit C3a and C5a generation and MAC formation, which are implicated in complement-mediated damage of host cells.

There are several types of C3 inhibitors being developed. One type of inhibitor makes use of naturally occurring proteins that bind to C3 or its derivatives, in particular cell surface complement receptors. The recombinant form of these receptors lacking the transmembrane region and the cytoplasmic tail of the parent molecule is soluble and able to neutralize C3 through binding. The first recombinant complement inhibitor was soluble CR1 ("sCR1"), which has been tested in clinical trials for complement inhibition in ischemia-reperfusion injury (Weisman et al., "Soluble Human Complement Receptor Type 1: In Vivo Inhibitor of Complement Suppressing Post-ischemic Myocardial Inflammation and Necrosis," *Science* 249:146-151 (1990)). Recently, the extracellular domain of human complement receptor of the immunoglobulin superfamily ("CRIg") has also been developed to serve as an inhibitor of the alternative pathway and shown to reverse inflammation and bone destruction in experimental arthritis (Katschke et al., "A Novel Inhibitor of the Alternative Pathway of Complement Reverses Inflammation and Bone Destruction in Experimental Arthritis" *The Journal of Experimental Medicine* 204:1319-1325 (2007)). Another type of C3 inhibitor is a peptide aptamer such as Compstatin, a 13-residue cyclic peptide isolated from a combinatorial library (Sahu et al., "Inhibition of Human Complement by a C3-binding Peptide Isolated from a Phage-displayed Random Peptide Library," *Journal of Immunology* 157:884-891 (1996)). This peptide binds to C3 and inhibits its cleavage by C3 convertase. Its effect has been tested in several clinically relevant models.

Aptamers have previously been designed for uptake by a specialized structure called the flagellar pocket of the parasitic organism *Trypanosoma brucei*, with the goal of directing RNA-conjugated toxins to the lysosomal compartment of the organism as a therapy to treat parasitic infection in humans (Homann et al., "Uptake and Intracellular Transport of RNA Aptamers in African Trypanosomes Suggest Therapeutic 'Piggy-back' Approach," *Bioorg. Med. Chem.* 9:2571-2580 (2001)). However, this approach was limited to directing a toxin-conjugated aptamer to a specific compartment within a parasitic organism and not designed to exploit a receptor on the organism's surface or make use of the lysosome's function to break down aptamer-bound endogenous or exogenous molecules. Toxins considered for this approach, with the intention of disrupting lysosomes using molecules that undergo conformational changes on encountering a pH shift, included poly(2-ethyl acrylic acid), poly(lysine dodecanamide), and melittin, a component of honeybee venom (Goringer et al., "RNA Aptamers as Potential Pharmaceuticals Against Infections with African Trypanosomes," *Handbook of Experimental Pharmacology* 173:375-93 (2006)). It has also been suggested that targeting the trypanosome's surface with aptamers conjugated to antigens renders the parasites susceptible to recognition by antibodies (Lorger et al., "Targeting the Variable Surface of African Trypanosomes with Variant Surface Glycoprotein-specific, Serum-stable RNA Aptamers," *Eukaryotic Cell* 2(1):84-94 (2003)). More recently, a nanobody targeting strategy has been developed ("Experimental Therapy of African Trypanosomiasis with a Nanobody-conjugated Human Trypanolytic Factor," *Nature Medicine* 12(5):580-4 (2006)). However, none of these approaches involved promoting destruction of endogenous or exogenous molecules by targeting these molecules to the lysosome.

The idea of conscripting the complement system, especially the alternative pathway, in cancer immunotherapy was proposed more than 20 years ago, but then neglected for a long time as the major emphasis was put on cell-mediated immune response against cancer (Cooper, "Complement and Cancer: Activation of the Alternative Pathway as a Theoretical Base for Immunotherapy," *Advances in Immunity and Cancer Therapy* 1:125-166 (1985)). However, with the introduction of monoclonal antibodies ("mAbs"), complement has come into play with great potential as an effector system in cancer immunotherapy (Macor et al., "Complement as Effector System in Cancer Immunotherapy," *Immunology Letters* 111:6-13 (2007)). Most mAbs that mediate antibody-dependent cellular cytotoxicity ("ADCC") also activate the complement system. Complement has a number of advantages over other systems in that it is made of molecules that can easily penetrate the tumor mass and many of these molecules can be supplied locally by cells nearby. C3b/iC3b deposited on tumor cells promotes adhesion of effector cells such as macrophages and NK cells through complement receptors, whereby cytotoxicity may ensue with the help of additional signals. A potential problem with this approach is the inhibitory effect of membrane-bound complement regulatory proteins ("mCRPs") that are often overexpressed on tumor cells, which is a mechanism used by these cells evade complement attack (Jurianz et al., "Complement Resistance of Tumor Cells Basal and Induced Mechanisms," *Molecular Immunology* 36:929-939 (1999)). However, efficient elimination of opsonized tumor cells can be achieved by blocking or overwhelming these mCRPs.

Compared to the protein-based reagents mentioned above, such as recombinant extracellular domains of complement receptors, monoclonal antibodies, and peptide aptamers, nucleic acid aptamers possess some compelling advantages. Nucleic acid molecules not only carry information in their linear sequences, but also fold into well-defined shapes that may be recognized specifically by proteins or other partners. The method known as in vitro selection or Systematic Evolution of Ligands by Exponential Enrichment ("SELEX") attempts to generate novel nucleic acid ligands known as aptamers by applying genetic selection directly to a population of nucleic acid molecules through a process that emulates Darwinian evolution (Tuerk et al., "Systematic Evolution of Ligands by Exponential Enrichment: RNA Ligands to Bacteriophage T4 DNA Polymerase," *Science* 249:505-510 (1990); Ellington et al., "In Vitro Selection of RNA Molecules that Bind Specific Ligands," *Nature* 346:818-822 (1990)). To generate RNA aptamers, the SELEX experiment starts with a large randomized sequence pool containing $10^{14}$-$10^{16}$ different species that fold into different shapes determined by their different sequences. This pool is then subjected to iterative cycles of selection and amplification. In each cycle, a target such as a protein molecule is used to select from the pool RNA molecules that bind it. Following the separation of bound RNA from unbound, the bound fraction is amplified by RT-PCR to generate a new pool for the next cycle. Usually, RNA ligands with the highest affinity for the target protein will dominate the population in 8-12 rounds. At the end of the process, the winning aptamers are cloned and sequenced for further characterization.

The aptamers generated by this process are capable of binding to a wide variety of targets with high affinity and specificity (Gold et al., "Diversity of Oligonucleotide Functions," *Annual Rev. Biochem.* 64:763-797 (1995); Wilson et al., "In Vitro Selection of Functional Nucleic Acids," *Annual Rev. Biochem.* 68:611-647 (1999)). Both DNA and RNA aptamers often bind their targets with dissociation constants ($K_d$) in the low nanomolar or picomolar range ($1 \times 10^{-7}$-$10^{-12}$M) and are able to discriminate between related proteins that share common structural features. In addition to their widespread utility as molecular probes in basic research and diagnostic applications, aptamers are quickly becoming an exciting new class of therapeutic agents (Nimjee et al., "Aptamers: An Emerging Class of Therapeutics," *Annual Rev. Medicine* 56:555-583 (2005)). With the advent of genomics and proteomics, protein-protein interaction is recognized as a promising category of drug targets. However, protein surfaces in direct contact with each other usually involve an area of about 1600 Å$^2$ with relatively flat topography, causing concerns about the capacity for binding specificity of small molecules of less than 500 Da with less than 500 Å$^2$ of total solvent-accessible surface area (Golemis et al., "Protein Interaction-targeted Drug Discovery: Evaluating Critical Issues," *BioTechniques* 32:636-638, 640, 642 (2002); Lo Conte et al., "The Atomic Structure of Protein-protein Recognition Sites," *J. Mol. Biol.* 285:2177-2198 (1999); Juliano et al., "Macromolecular Therapeutics: Emerging Strategies for Drug Discovery in the Postgenome Era," *Molecular Interventions* 1:40-53 (2001)). Individual aptamers are usually 25-50 nucleotides long and weigh 8-16 kDa, which makes them better able to interact with proteins. Like antibodies, they can be made to order specifically for a particular protein. But unlike antibodies, aptamers are produced by a scalable in vitro process and display low to no immunogenicity or toxicity even when administered in pre-clinical doses 1000-fold greater than doses used in therapeutic application (Pendergrast et al., "Nucleic Acid Aptamers for Target Validation and Therapeutic Applications," *J. Biomolecular Techniques* 16:224-234 (2005)).

Aptamers also compare favorably with other oligonucleotide-based pharmaceuticals. The targets of reagents like antisense and siRNA are located exclusively in the intracellular compartments as they act at the gene or mRNA level; delivery of these molecules to the target sites is a formidable task. In contrast, aptamers can exert their function against extracellular targets, which are much easier to access (Pestourie et al., "Aptamers Against Extracellular Targets for In Vivo Applications," *Biochimie* 87:921-930 (2005)). Although natural RNA and DNA have poor pharmacokinetics when administered by intravenous or subcutaneous injection, they can be chemically improved to enhance their stability and to control their clearance (Pendergrast et al., "Nucleic Acid Aptamers for Target Validation and Therapeutic Applications," *J. Biomolecular Techniques* 16:224-234 (2005)). For example, to render aptamers resistant to nuclease degradation, RNA modified at the 2' position of pyrimidines with fluoro or amino groups can be used for selection. Additional post-selection modification or substitution can further increase aptamer residence time in the blood. For example, renal clearance of aptamers smaller than 40 kD can be reduced through conjugation with polyethylene glycol ("PEG"), attachment to liposomes, or cholesterol. Moreover, the activity of aptamers can be controlled by oligonucleotide antidotes that base-pair with the aptamers to prevent them from forming the correct shape to bind their targets (Rusconi et al., "Antidote-mediated Control of an Anticoagulant Aptamer In Vivo," *Nature Biotechnology* 22:1423-1428 (2004)).

The first aptamer-based therapeutic approved for clinical use, Macugen (pegaptanib sodium injection), is a modified RNA aptamer directed to an isoform of vascular endothelial growth factor (VEGF$_{165}$) and used to treat the wet form of age-related macular degeneration ("AMD") as a locally acting drug (Ruckman et al., "2'-Fluoropyrimidine RNA-based Aptamers to the 165-amino Acid Form of Vascular Endothelial Growth Factor (VEGF$_{165}$) Inhibition of Receptor Binding and VEGF-induced Vascular Permeability through Interactions Requiring the Exon 7-encoded Domain," *J. Biol. Chem.* 273:20556-20567 (1998); Lee et al., "A Therapeutic Aptamer Inhibits Angiogenesis by Specifically Targeting the Heparin Binding Domain of VEGF$_{165}$," *Proc. Nat'l Acad. Sci. U.S.A.* 102:18902-18907 (2005)). The Macugen aptamer was generated by SELEX in the form of 2' fluoro-pyrimidine RNA (2'F-Py RNA) and underwent post-selection 2'O-methyl-purine modifications. Its ends were further protected by 5' PEG adducts and a 3' dT attached via a 3'-3' linkage. This aptamer binds to its target with a K$_d$ of 50 pM and arrests the progression of wet AMD by preventing blood vessel growth. Clinical safety studies show that this drug is well tolerated at doses up to 10-fold higher than the 0.3-mg dose approved for the treatment of AMD (Chakravarthy et al., "Year 2 Efficacy Results of 2 Randomized Controlled Clinical Trials of Pegaptanib for Neovascular Age-related Macular Degeneration," *Ophthalmology* 113:1508, e1501-1525 (2006); Apte et al., "Pegaptanib 1-year Systemic Safety Results from a Safety-pharmacokinetic Trial in Patients with Neovascular Age-related Macular Degeneration," *Ophthalmology* 114:1702-1712 (2007)). In addition to Macugen, there are many other aptamers and aptamer-enabled technologies being evaluated in various stages of clinical trials for numerous diseases, including cancer. Notably, a 2'F-Py RNA aptamer for the prostate-specific membrane antigen ("PSMA") was conjugated with docetaxel-encapsulated nanoparticles for targeted uptake by the prostate cancer cells (Lupold et al., "Identification and Characterization of Nuclease-stabilized RNA Molecules that Bind Human Prostate Cancer Cells Via the Prostate-specific Membrane Antigen," *Cancer Research* 62:4029-4033 (2002); Farokhzad et al., "Targeted Nanoparticle-aptamer Bioconjugates for Cancer Chemotherapy in vivo," *Proc. Nat'l Acad. Sci. U.S.A.* 103:6315-6320 (2006)). In a xenograft nude mouse model of prostate cancer, these bioconjugates showed significant anticancer efficacy without the systemic toxicity common to chemotherapeutics.

Because aptamers are produced by an in vitro process, the initial therapeutic leads can be isolated rapidly, and the production can be readily scaled up in a cost-effective manner. Because nucleic acids can easily regain activity following exposure to denaturing conditions, their shelf life is long. They can be administered by either intravenous or subcutaneous injection. Previously, aptamers against C5 have been developed as complement inhibitors (US Patent Application Publication No. 2006/0018871 A1) and aptamers against C3b have been similarly developed as complement inhibitors (PCT Application Publ. No. WO 97/42317).

The present invention is directed to individual aptamers for C3 and its derivatives as complement inhibitors, and composite aptamers binding C3 or its derivatives and a target protein to mediate opsonization by C3b/iC3b.

SUMMARY OF THE INVENTION

A first aspect of the present invention relates to a nucleic acid aptamer having a first domain that binds to a complement protein C3 or biologically active proteolytic product thereof.

A second aspect of the present invention relates to a molecular complex, which includes the nucleic acid aptamer according to the first aspect of the present invention and a complement protein C3 or biologically active proteolytic product thereof bound to the nucleic acid aptamer at the first domain.

A third aspect of the present invention relates to a molecular complex, which includes a nucleic acid aptamer having a first domain that binds to a complement protein C3 or biologically active proteolytic product thereof and a second domain that binds to a molecule different from the complement protein C3 or biologically active proteolytic product thereof. The molecular complex also includes a complement protein C3 or biologically active proteolytic product thereof bound to the nucleic acid aptamer at the first domain and a target protein bound to the nucleic acid aptamer at the second domain.

A fourth aspect of the present invention relates to a cell having a target protein on its surface to which the second domain of the molecular complex according to the third aspect of the present invention is bound.

A fifth aspect of the present invention is directed to a method of inhibiting activity of complement protein C3 or a biologically active proteolytic product thereof. This method involves providing a nucleic acid aptamer according to the first aspect of the present invention. A complement protein C3 or biologically active proteolytic product thereof is contacted with the nucleic acid aptamer under conditions effective to bind to the complement protein C3 or biologically active proteolytic product thereof and thereby inhibit activity thereof.

A sixth aspect of the present invention is directed to a method of promoting opsonization of a cell or an extracellular protein. This method involves providing a nucleic acid aptamer having a first domain that binds to a biologically active proteolytic product of complement protein C3 and a second domain that binds to a molecule different from the biologically active proteolytic product of complement protein C3. A cell surface protein on a cell or an extracellular protein is contacted with the aptamer, whereby the aptamer binds the target protein at the second domain and a biologically active proteolytic product of complement protein C3 at the first domain, thereby promoting opsonization of the cell or extracellular protein.

A seventh aspect of the present invention is directed to a method of treating a disease or disorder involving undesirable cellular damage in a patient. This method involves providing a nucleic acid aptamer according to the first aspect of the present invention, where the aptamer binds to and inhibits the function of complement protein C3 or biologically active proteolytic product thereof. The nucleic acid aptamer is administered to the patient under conditions effective to treat a disease or disorder involving undesirable cellular damage in the patient.

An eighth aspect of the present invention is directed to a method of treating cancer in a patient. This method involves providing a nucleic acid aptamer having a first domain that binds to a biologically active proteolytic product of complement protein C3 and a second domain that binds to a molecule different from the biologically active proteolytic product of complement protein C3, where the molecule different from the biologically active proteolytic product of complement protein C3 is a cancer cell surface protein. The nucleic acid aptamer is administered to a patient under conditions effective to promote opsonization of the cancer cell and thereby treat the patient for cancer.

A ninth aspect of the present invention is directed to a method of treating cancer in a patient. This method involves providing a nucleic acid aptamer having a first domain that binds to a biologically active proteolytic product of complement protein C3 and a second domain that binds to a molecule different from the biologically active proteolytic product of complement protein C3. A near-infrared emitting nanoparticle probe is conjugated to the aptamer. The second domain binds a target protein on a surface of a cancer cell. The probe is contacted with photon energy, whereby the probe converts the photon energy to heat energy and releases heat, thereby killing the cell and treating cancer in the patient.

A tenth aspect of the present invention is directed to a method of imaging a tumor in a patient. This method involves administering to a patient a nucleic acid aptamer that recognizes a cancer cell-specific surface protein, where the aptamer is conjugated to an imaging label, and detecting whether the conjugated imaging label is localized within any tissues of the patient.

An eleventh aspect of the present invention is directed to a method of removing an extracellular substance from a sample or body. This method involves providing a sample or body containing an extracellular biomolecule targeted for removal. The sample or body is contacted with an aptamer capable of binding the extracellular biomolecule under conditions effective to bind the extracellular biomolecule to the aptamer. The aptamer-bound biomolecule is caused to be destroyed or removed from the sample or body.

A twelfth aspect of the present invention is directed to a method of identifying compounds that bind C3 or a biologically active proteolytic product thereof. This method involves exposing C3 or biologically active proteolytic product thereof to the aptamer according to the first aspect of the present invention and a test compound and determining whether the test compound prevents aptamer binding to C3 or biologically active proteolytic product thereof. Prevention of binding identifies the compound as one that binds C3 or biologically active proteolytic product thereof.

Accordingly, the present invention relates to aptamers for the complement C3 or its biologically active proteolytic products, C3b, iC3b, or any combination thereof. These aptamers bind to discrete sites on the surface of these proteins. Any particular aptamer may be able to inhibit one or more activities of these proteins; some of them may not interfere with any known activity of these proteins.

The present invention also relates to individual aptamers that inhibit C3 function. These aptamers are therapeutic by virtue of their effects on the complement system, and hence can be used for treatment of diseases with an inflammatory or autoimmune component to prevent host cell damage.

The present invention also relates to individual aptamers that bind to C3b or iC3b, and do not interfere with C3b or iC3b recognition by C3 receptors on phagocytic cells.

The present invention also relates to composite bi-functional aptamers as molecular adaptors. A bi-functional aptamer as described herein has a generic "utility" moiety, e.g., the first domain, composed of one or more "utility attaching" aptamers and a specific "targeting" moiety, e.g., the second domain, comprising one or more target-binding aptamers. A bi-functional aptamer induces the proximity between a target molecule and a utility molecule to elicit biological action on the target through the utility molecule. Target-binding aptamers provide exquisite specificity for a vast number of diverse target molecules and bridge each of them with one or a few types of utility molecules.

One example of the bi-functional aptamers can be used for C3b/iC3b mediated opsonization assisted by an aptamer-based secondary adaptor. In this molecular configuration, the bi-functional aptamer induces the proximity of a target to the active form of the complement component C3, whereby C3b/iC3b can act as opsonins to tag the targets as "foreign" to cause their clearance or damage by phagocytes and other effector cells. Here, bi-functional aptamers improve the efficiency and refine the specificity of C3b/iC3b as opsonins. In particular, the targets can be "self" components that are intended to be down regulated or eliminated.

Another example of the bi-functional aptamers can be used for C3/aptamer-mediated opsonization of cells. When the target protein is a membrane protein exposed on the cell surface, a bi-functional aptamer comprising one or more aptamers for this target protein and one or more aptamers for C3b/iC3b will recruit C3b/iC3b to the cell surface, effectively opsonizing the cell. In particular, when the aforementioned cell is a cancer cell, increased deposition of C3b/iC3b may induce cytotoxicity and, therefore, is therapeutically desirable.

The present invention also relates to CR3-dependent cytotoxicity ("CR3-DCC") of cancer cells induced by bi-functional opsonizing aptamers, described above, and an adjuvant. CR3-DCC is normally reserved for killing fungi that bear β-glucan as an exposed component of their cell wall. Although tumor cells, like other host cells, lack β-glucan as a surface component, β-glucan can be supplied as an adjuvant to manipulate the CR3 so it will be primed to trigger cytotoxicity of iC3b-coated tumor cells.

A further example of the bi-functional aptamers can be used for C3/aptamer mediated opsonization and clearance of extracellular proteins. This is realized by bi-functional aptamers that simultaneously bind an extracellular target protein and C3b/iC3b, thereby triggering the endocytosis of the target protein by phagocytic cells.

The present invention also relates to the use of multivalent molecules such as bifunctional aptamers, bivalent antibodies, or other chemical species to bridge cellular receptors to secreted or extracellular proteins, antigens, pathogens, or toxins to utilize cellular pathways that mediate internalization of ligands by cells, participate in cell signaling, or otherwise exploit receptor function. For example, a variety of receptors function to remove or sample components from the extracellular environment. Multivalent aptamers binding to these receptors can be utilized to reduce levels of an extracellular target, stimulate an immune system response by triggering cell signaling or, alternatively, to mimic natural receptor function such as antigen presentation by linking a peptide or other antigen to a molecule such as major histocompatibility complex ("MHC") I and/or II.

The present invention also relates to the development of imaging and coupled imaging/therapeutic technologies using multivalent aptamers. Novel technologies including such detector molecules as quantum dots and gold or silver nanoparticles are being developed for in vivo imaging and therapeutic applications, and aptamers can play a useful role in targeting these and other detector molecules, including traditional radiolabels, to specific biological entities such as cellular receptors (Hicke et al., "Escort Aptamers: A Delivery Service for Diagnosis and Therapy," *Clin. Invest.* 106:923-928 (2000), which is hereby incorporated by reference in its entirety).

The present invention also relates to the use of aptamers to develop pharmaceutical leads based on their ability to compete for binding with small molecule drugs in high-throughput assays. For example, aptamers that interact with C3, C3b, and iC3b can be useful for identification of small molecule drugs that might bind to and interact with the complement system to inhibit or stimulate the body's immune or inflammatory responses.

BRIEF DESCRIPTION OF THE DRAWINGS

FIG. 8A illustrates binding of Apt[C3-GFP] to either C3 (or its derivatives) or GFP (and its derivatives). The "low" and "high" concentration of GFP, d2EGFP, GFP, mCherry, and Azami Green are 50 nM and 250 nM respectively. The "low" and "high" concentration of iC3b and C3b are 50 nM and 250 nM, of C3 are 20 nM and 100 nM, and of BSA are 500 nM and 1 μM, respectively. FIG. 8B is a schematic diagram of the protocol used to demonstrate triple complex formation. FIG. 8C shows the detection of triple complex formation using western blot analysis with anti-GFP antibody.

FIG. 10A shows co-localization of GFP with iC3b molecules, which were visualized using anti-iC3b antibodies. The THP-1 cells were differentiated, and fixed after endocytosis. In the experimental panel, cells were incubated with Apt[C3-GFP], GFP and iC3b. iC3b was omitted in the control. After permeabilization the cells were sequentially incubated with anti-iC3b antibody followed by Alexa Fluor 594 secondary antibody. FIG. 10B shows co-localization of GFP with lysosomes. Lysosomes were visualized using the LysoTracker™ dye. In the experimental panel, the cells were incubated with Apt[C3-GFP], GFP, iC3b and LysoTracker™. iC3b was omitted in the control. Cells were fixed with 4% paraformaldehyde.

FIG. 11A illustrates the rapid disappearance of the d2EGFP signal compared to that of GFP. The THP-1 cells were incubated with Apt[C3-GFP], iC3b, and either GFP or d2EGFP. Live cells were photographed as in FIG. 9. FIG. 11B illustrates bi-color tracking of the GFP-mCherry fusion protein. An early (15 minutes) and a late (48 hours) stage are shown. In the experimental panel, cells were incubated with Apt[C3-GFP], GFP-mCherry and iC3b. iC3b was omitted in the control. In the first and second row, cells were fixed with 4% paraformaldehyde after incubation with the above components for 15 minutes. In the bottom panel, the cells were incubated for 30 minutes with the same components, followed by washing with complete RPMI-1640 medium, and allowed to grow for 48 hours in complete RPMI-1640 before fixation.

DETAILED DESCRIPTION OF THE INVENTION

The present invention relates generally to the field of nucleic acids and, more particularly, to individual and composite nucleic acid aptamers that recognize and bind the complement protein C3 or its biologically active proteolytic products, C3b, iC3b, or any combination thereof, and methods of their use. The individual aptamers are useful as therapeutics in complement-related inflammatory, autoimmune disorders and other diseases in which C3-mediated complement activation has been implicated. The composite aptamers are useful for inducing specific opsonization by C3b/iC3b of cells or extracellular target molecules to elicit cytotoxicity or clearance by phagocytes or other effector cells. The target cells and molecules to be opsonized include, but are not limited to, cancer cells and cancer-associated proteins.

A first aspect of the present invention relates to a nucleic acid aptamer having a first domain that binds to a complement protein C3 or biologically active proteolytic product thereof.

Figure 1:
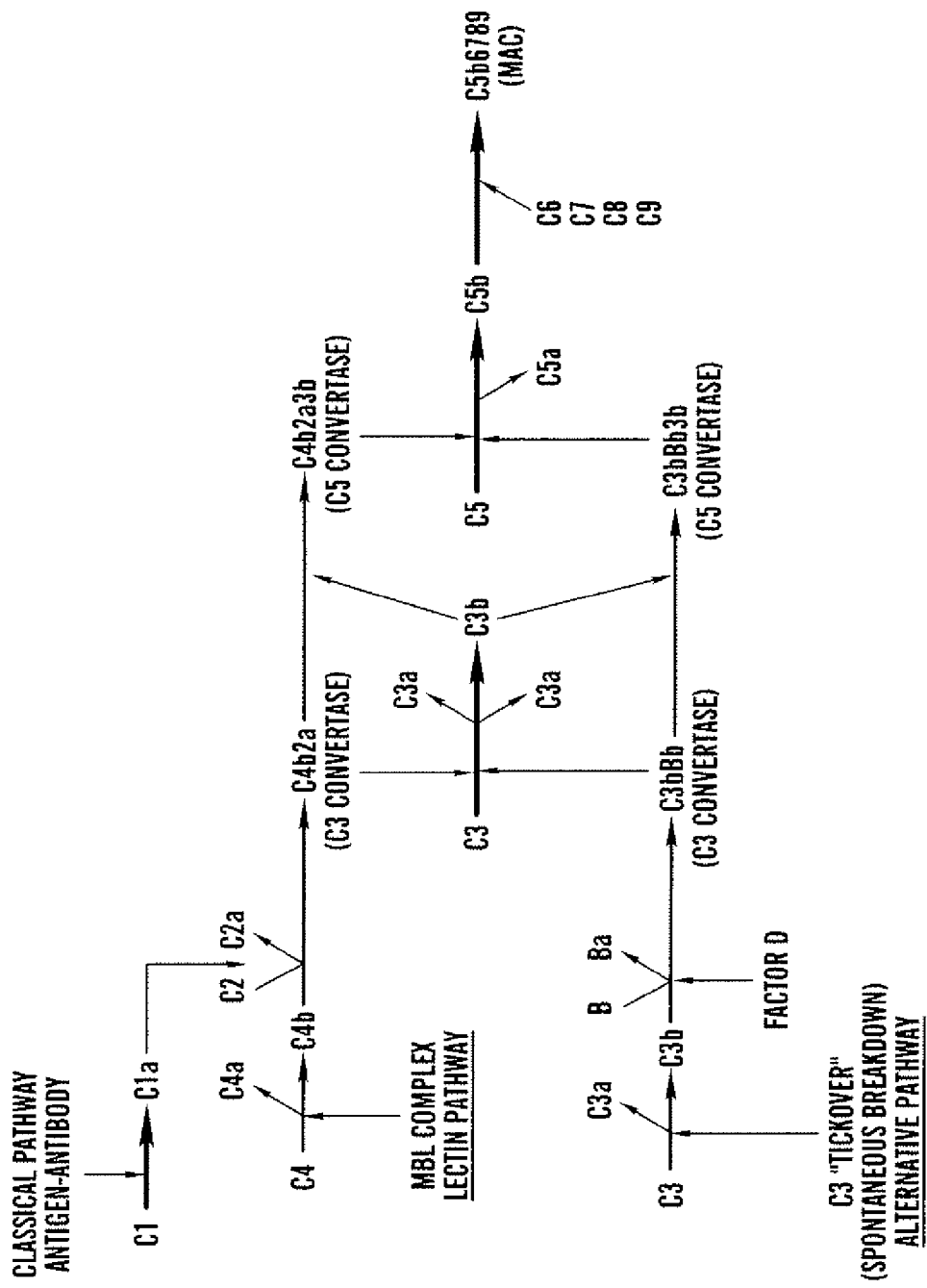
FIG. 1 is a schematic illustration of the three pathways of complement activation. The complement system is activated through three pathways: the classical pathway, the alternative pathway, and the lectin pathway. All of these pathways lead to the generation of homologous variants of the protease C3-convertase. The alternative pathway is considered the evolutionarily original pathway, and can be initiated by spontaneous hydrolysis ("tickover") of C3. The classical pathway participates most directly in the adaptive immune response and typically requires antibodies for initiation. The lectin pathway starts with the binding of mannan-binding lectin ("MBL") to microbial surfaces and converges with the classical pathway at the level of complement C4. The complement system includes about 35 cell surface and soluble plasma proteins, in which the third component, C3, occupies a central position. In all three pathways, the pivotal step is the conversion of C3 to C3b.
Figure 2:
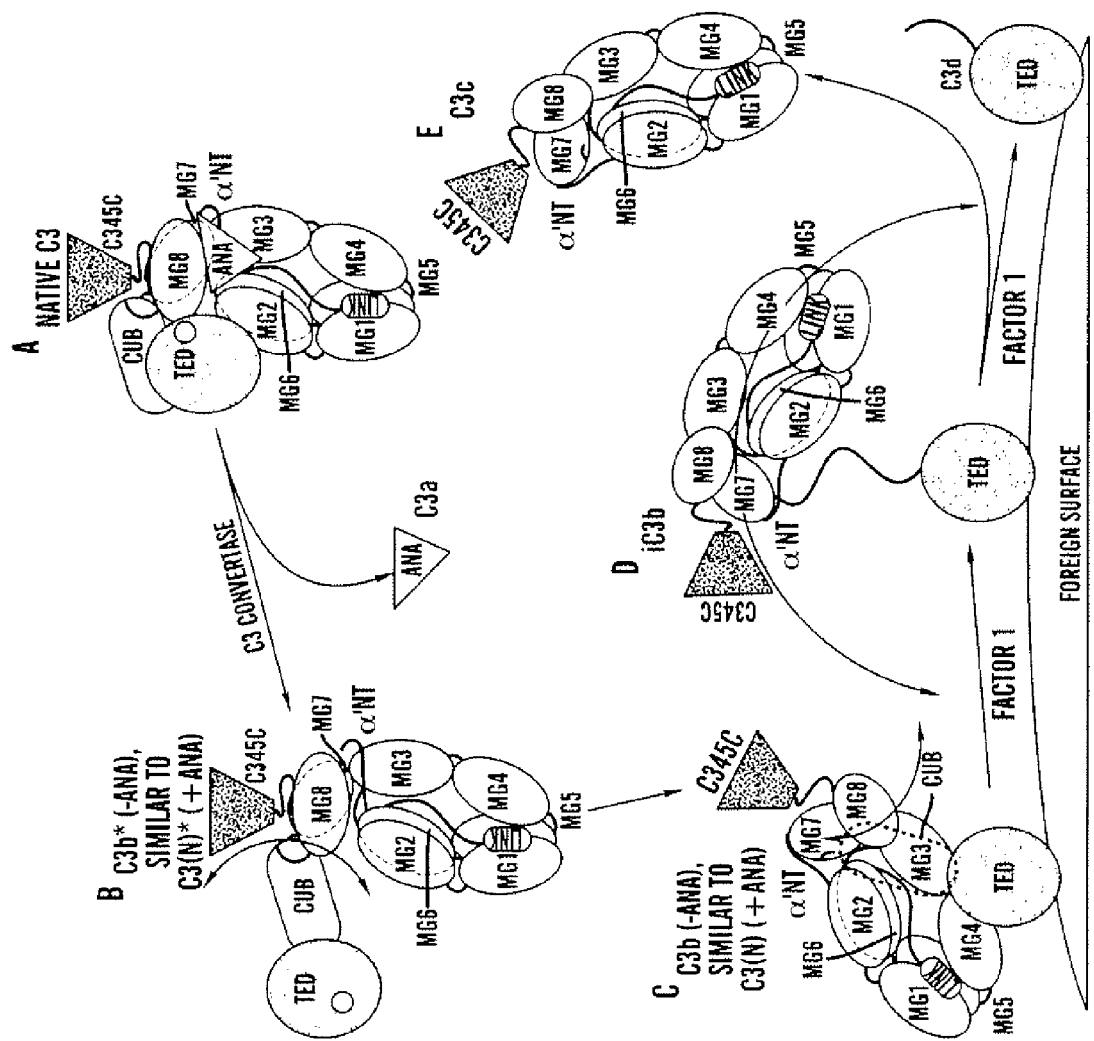
FIG. 2 is a schematic diagram of domain rearrangements and flexibility in C3 products. This figure is taken from Nishida et al., "Structural Transitions of Complement Component C3 and Its Activation Products," *Proc Nat'l Acad. Sci. U.S.A.* 103:19737-19742 (2006), which is hereby incorporated by reference in its entirety.

The native complement protein C3 is a complex and flexible protein with a molecular weight of 185 kDa, and it is biologically inactive. The proteolytic cleavage of C3 causes a dramatic conformational change and yields its active form C3b (Janssen et al., "Structures of Complement Component C3 Provide Insights into the Function and Evolution of Immunity," Nature 437:505-511 (2005); Janssen et al., "Structure of C3b Reveals Conformational Changes that Underlie Complement Activity," Nature 444:213-216 (2006); Wiesmann et al., "Structure of C3b in Complex with CRIg Gives Insights into Regulation of Complement Activation," Nature 444:217-220 (2006); Abdul Ajees et al., "The Structure of Complement C3b Provides Insights into Complement Activation and Regulation," Nature 444:221-225 (2006); Nishida et al., "Structural Transitions of Complement Component C3 and Its Activation Products," Proc. Nat'l Acad. Sci. U.S.A. 103:19737-19742 (2006), each of which is hereby incorporated by reference in its entirety). C3 is composed of two chains, 13 and a, which together form 13 structural domains, as shown in FIG. 2. The 13 chain forms five and a half macroglobulin ("MG") domains and a linker ("LNK") domain, with MG1-4 forming one ring and MG5 and 6 forming a second, overlapping half-ring. The remaining domains are formed by the a chain, with the MG7 and 8 extending the second half-ring and the C345C domain forming a knob-like protrusion connected to the ring via the Anchor domain. Between MG7 and 8 is inserted the "complement C1r/C1s, Uegf, Bmpl" ("CUB") domain, and between the two halves of the CUB domain is in turn inserted a TED. The anaphylatoxin ("ANA") domain is connected to the rest of the molecule through the a' amino-terminal segment ("a'NT") and wedged between MG3 and MG8; the removal of this domain as C3a in the process of C3 activation triggers a series of changes in the resultant C3b. The newly freed a'NT domain passes through a tunnel between the MG2, 3, and 6 domains and emerges on the opposite side of the MG ring. Meanwhile, the flexibility of the CUB domain increases and the TED swings away from MG8 to expose its acyl-imidazole bond to nucleophile attack by nearby pathogenic or antigenic surfaces. The C3b is further converted to iC3b and C3c through successive cleavages in the two halves of the CUB domain. iC3b is the predominant C3 opsonin in vivo. The conformational rearrangements described above are the major changes in the proteolytic conversion of C3 to C3b, and subsequently to iC3b and C3c. In addition to the activated form of the thioester, many other binding sites are also exposed.

C3, C3b, and iC3b are large molecules with many binding sites for other factors. Accordingly, many different classes of aptamers may exist to recognize discrete sites on the surface of these molecules and it is desirable to isolate all of them. However, even when multiple targets or target sites are present during in vitro selection, in most cases the aptamers identified in the final rounds of conventional SELEX only recognize the most abundant or easily recognizable target site. Besides, although RNA is an extraordinarily versatile type of molecule, it cannot be guaranteed that an RNA ligand will always exist for a particular binding site on a protein domain naturally recognized by a non-RNA molecule. On the other hand, multiple different RNA sequence/structure solutions may exist to fit a single site, as seen in the TBP aptamers that bind the DNA binding surface. To isolate multiple classes of aptamers for discrete sites on a single protein molecule, a suite of effective selection schemes have been developed to acquire unprecedented results. This approach pursues exhaustiveness in aptamer identification in a practical sense: every RNA ligand existing in the starting sequence pool should be isolated. This scheme should be equally viable for other types of nucleic acids.

As disclosed in U.S. Patent Application Publication No. 2004/0053310 (which is hereby incorporated by reference in its entirety), a theoretic description of the process of in vitro selection was formulated based on the exponential model of single species growth and decay in a population of different species. According to this model, multiple classes of aptamers may be isolated exhaustively, as every individual in the original pool with affinity to any target above the average affinity of the unselected pool will have a chance to be isolated one by one according to their rank of "growth rate" defined at the beginning of the experiment. In the scheme, the most fit aptamer clone or clones are converted to the least fit one(s) after their identification, thus allowing clones to dominate the selected pools in successive stages in an order according to their original rank of fitness. More specifically, assuming (a) there exist n aptamers $\{Apt_1, Apt_2, \ldots Apt_n\}$, (b) each of these is directed to a distinct target in the set $\{T_1, T_2, \ldots T_n\}$, and (c) these aptamers have equal abundance in the initial unselected pool, then, $Apt_1$ will have the maximal growth rate in the course of selection, and the order ($Apt_1$ $Apt_2 \ldots Apt_n$) will be the order of their initial rank of "growth rate," if either of the two sets of following conditions are met:
1-1: Each target is present at identical concentration, and
1-2: The affinity (A) of the aptamer to their corresponding target has the rank $A_{apt1} > A_{apt2} > \ldots > A_{aptn}$; or
2-1: The affinity of each aptamer to their corresponding target is identical, and
2-2: The concentration of individual targets [T] is present at the rank $[T_1] > [T_2] > \ldots > [T_n]$.

This description identifies three parameters that affect the growth of a candidate clone: initial abundance, relative affinity to targets, and relative target concentration, all of which are difficult to change in some cases. The initial abundance of an aptamer is determined by its information content. While this can be estimated once the sequence is identified, it is impossible to alter experimentally. The relative affinity is also a fixed property. The relative concentration of individual targets can be varied if the targets are separable. But on a macromolecule or supramolecular assembly with multiple sites impossible to separate physically, the relative target concentration is also fixed. However, exhaustive isolation of aptamers requires the capability of manipulating these parameters experimentally to reduce the fitness of those aptamers after their isolation. To address these inconveniences, two experimental approaches were developed by changing instead the "viability" of candidates and the "availability" of target sites. The method disclosed in U.S. Patent Application Publication No. 2004/0053310 (which is hereby incorporated by reference in its entirety) utilizes the concept of "negative selection according to genotype" to eliminate isolated aptamers from the candidate pool to facilitate the identification of other aptamers. The "viability" of known aptamers is reduced by RNase H digestion with the help of marking oligos annealed to the aptamer. Recently, non-amplifiable versions of isolated aptamers have been used in the binding reaction to mask their binding sites. This method reduces the availability of these sites and facilitates the isolation of aptamers for other sites (Shi et al., "RNA Aptamers Directed to Discrete Functional Sites on a Single Protein Structural Domain," *Proc. Nat'l Acad. Sci. U.S.A.* 104:3742-3746 (2007), which is hereby incorporated by reference in its entirety). Both experimental procedures, when combined, ensure the isolation of multiple aptamers for discreet sites on C3, C3b, or iC3b.

The nucleic acid aptamers of the present invention can take any form of nucleic acid molecule, including both natural and chemically modified DNA and RNA, in both D and L enantiomeric forms, as well as derivatives thereof (including, but not limited to 2'-fluoro-, 2'-amino, 2'O-methyl, 5' iodo-, and 5'-bromo-modified polynucleotides). Nucleic acids containing modified nucleotides and the L-nucleic acids (sometimes termed Spiegelmers®) enantiomeric to natural D-nucleic acids are used to enhance biostability, whereby they can be delivered to and function in environments containing nucleases that would degrade the natural form of DNA or RNA.

In one embodiment, the purified protein C3 is used as the target molecule in SELEX experiments to isolate RNA aptamers, and the isolated aptamers are then tested for their affinity to C3, C3b, and iC3b, respectively. In another embodiment, the purified protein C3b is used as the target molecule in SELEX experiments to isolate RNA aptamers, and the isolated aptamers are then tested for their affinity to C3, C3b, and iC3b, respectively. In yet another embodiment, the purified protein iC3b is used as the target molecule in SELEX experiments to isolate RNA aptamers, and the isolated aptamers are then tested for their affinity to C3, C3b, and iC3b, respectively.

Aptamers are selected according to their capability to bind a molecule, and the binding site of the isolated aptamer is not specified by the process of in vitro selection. Among the aptamers for C3 and its derivatives isolated according to the method of exhaustive selection described above, some will be able to inhibit one or more activities of these proteins; others will not interfere with any known activity of these proteins. Those aptamers that inhibit C3 function are therapeutic by virtue of their effects on the complement system.

Nucleic acid aptamers of the present invention may have only a single domain that binds a target (e.g., the complement protein C3 or biologically active proteolytic product thereof), or more than a single binding domain. For example, the nucleic acid aptamer may be in the form of a multivalent aptamer (with multiple binding domains) or a bivalent aptamer (with two binding domains). Aptamers with more than one binding domain may bind multiple sites on a single target, or multiple targets (a multi-functional aptamer).

Compared to small organic compounds and peptides, nucleic acid aptamers are relatively easy to assemble with other structural or functional elements of nucleic acids to form molecules with multiple functional sites. This allows aptamer-based molecular constructs to function not only as inhibitors by blocking binding sites on proteins, but also as novel connectors. Previously, a general method for designing and constructing composite aptamers was disclosed (U.S. Patent Application Publication No. 2005/0282190, which is hereby incorporated by reference in its entirety). This method can be utilized to build a specific type of composite aptamer that functions as a molecular adaptor.

Molecular adaptors connect diverse members of one type of molecule with one or very few molecules of a different type. An example of a molecular adaptor is an antibody. Within the same class of isotype, the generic end of the antibody, the Fc region, is virtually identical among antibodies against different antigens and can be recognized by a limited number of receptors. The exquisite specificity of antibodies resides in the Fab region, with their antigen binding sites (paratopes) encoded by gene segments that have undergone random combinations and mutations to create diversity in shape and charge distribution that matches specific antigens. As a result, a vast number of diverse antigens can be channeled through antibodies to only a few common destinations.

A composite aptamer that can function as a molecular adaptor should possess at least two distinctive types of function (or domains). Multiple aptamers are operably linked together to form a single molecular entity, in which two types of aptamers function independently. The first function (domain) is defined herein as the "targeting" function. This function (domain) is actualized through aptamers for individual molecules of the first (antigen-like) type. The second function (domain) is defined herein as the "utility" function. This function (domain) is actualized through aptamers for a "utility molecule" such as a receptor. Therefore, a composite aptamer that can function as a molecular adaptor must be a bi-functional aptamer. A bi-functional aptamer is not necessarily a bi-valent aptamer, as either function can be actualized through one or more aptamers, in which case each function or domain can be monovalent or multivalent.

Compared to individual or mono-functional multivalent aptamers, bi-functional aptamers entail more design criteria. First, a bi-functional aptamer and the two types of molecules it bridges together must co-exist or be co-compartmentalized so they will be able to meet and form a triple complex or three-party complex. The specific compartments can be blood or serum, extracellular matrix, cytoplasm, nucleus, or other organelle. Second, a critical distinction between the two functions is that the utility aptamer must not have inhibitory effect on the utility molecule, because in this molecular configuration the utility molecule is the effector on the target molecule. Third, the relative affinity (or apparent relative affinity) between the targeting moiety for the target molecule and the utility moiety for the utility molecule should be adjusted so that the former is higher than the latter. This will ensure that the utility molecules are not occupied by "empty carriers," a situation that would decrease the efficiency of the system.

The design and construct of bi-functional composite aptamers may involve a rational modular approach. First, aptamers are selected against the targets, followed by characterization and improvements. Second, aptamers for the utility molecule are isolated and their binding optimized. Finally, the generic utility moiety is grafted to different specific targeting aptamers using methods disclosed previously.

A particularly desirable type of molecular adaptor induces molecular proximity whereby molecular ablation may be achieved through directing a protein to the vicinity of its degradation machinery. As disclosed herein, a bi-functional aptamer for this purpose is a nucleic acid molecule that includes at least two different types of aptamer-derived functional modules. One or more copies of a first type of the functional module are directed towards one or more binding sites on the target protein to be ablated. One or more copies of a second type of the functional module are directed towards one or more components of the protein degradation machinery. Simultaneous binding of the bi-functional aptamer to both the target protein and the component or components of the protein degradation machinery would result in the inhibition and destruction of the target protein by the degradation machinery. Because aptamers can be generated against most proteins and composite molecules containing multiple aptamers can be designed and constructed in a combinatorial manner, the present invention provides a generic means to "knockout" protein targets, and thus have widespread utility in both basic and applied research fields.

According to one particular embodiment, the nucleic acid aptamer of the present invention has a first function (domain) that binds to the biologically active proteolytic product thereof complement protein C3 (C3b or iC3b) and a second function (domain) that binds to a molecule different from the biologically active proteolytic product of complement protein C3. As noted above, either domain can be monovalent or multivalent, in which case a plurality of aptamers can be present for binding the biologically active proteolytic products of C3, a plurality of aptamers can be present for binding the molecule different from the biologically active proteolytic product of C3, or both. The assembly of multi-valent aptamer constructs is described, for example, in U.S. patent application Ser. No. 11/103,122 to Shi et al., filed Apr. 11, 2005 (U.S. Patent Application Publication No. 2005/0282190A1), which is hereby incorporated by reference in its entirety. This prior publication discloses the use of three-way junctions to link together multi-functional and multi-valent aptamer units into a molecular complex.

Aptamers of the present invention can be used to bridge cellular receptors to secreted or extracellular proteins, antigens, pathogens, or toxins to promote their uptake, transmit cellular signals, or to otherwise exploit receptor function. In addition to CR1 and CR3, multiple receptors exist on cell surfaces that recognize a wide range of ligands. In particular, cells of the immune system that are specialized to sense infection or other danger to the organism, such as macrophages and dendritic cells ("DCs") capable of responding to cell debris, whole bacteria, low density lipoproteins ("LDL"), lipopolysaccharides, and other bacterial components (Callahan et al., "Heat-shock Protein 90 Associates with N-terminal Extended Peptides and Is Required for Direct and Indirect Antigen Presentation," *Proc. Nat'l Acad. Sci. U.S.A.* 105: 1662-1667 (2008), which is hereby incorporated by reference in its entirety). One subset of these receptors functions mainly in the uptake of extracellular material (Calderwood et al., "Cell Surface Receptors for Molecular Chaperones," *Methods* 43(3):199-206 (2007), which is hereby incorporated by reference in its entirety). For example, scavenger receptors include eight diverse families of receptors that are expressed on macrophages, endothelial cells, and some types of epithelial cells. These receptors are responsible for clearing excess cholesterol and lipids from the blood. The low density lipoprotein LDL related family of receptors comprises seven transmembrane proteins (LRP1, LRP1b, megalin/LRP2, LDL receptor, very low-density lipoprotein receptor, MEGF7/LRP4, LRP8/apolipoprotein E receptor 2) with strong structural similarities that function in endocytosis and cell signaling. LDL receptor related protein 1 (LRP-1) performs a wide range of functions; at least 40 ligands have been identified that interact with this receptor, including extracellular matrix proteins and cytokines, suggesting roles in cell migration and tissue invasion (May et al., "The LDL Receptor-related Protein (LRP) Family: An Old Family of Proteins with New Physiological Functions," *Annals of Medicine* 39(3):219-28 (2007), which is hereby incorporated by reference in its entirety).

Lipid clearance receptors such as LRP-1 have the potential to clear large amounts of aptamer-targeted proteins: LDL receptors and other lipid uptake receptors take up a large volume of material, with cells of a normal human liver (the main organ of uptake) transporting ~7.5 mg of lipid from the blood each day (Dietschy et al., "Role of Liver In the Maintenance of Cholesterol and Low Density Lipoprotein Homeostasis In Different Animal Species, Including Humans," *J. Lipid Res.* 34(10):1637-59 (1993), which is hereby incorporated by reference in its entirety). Because liposomes are opsonized by iC3b (Yan et al., "Liposome Opsonization," *J. Liposome Res.* 15(1-2):109-39 (2005), which is hereby incorporated by reference in its entirety), lipid clearance represents a secondary mode of action of the aptamers described herein; aptamers bound to iC3b associated with liposomes would most likely be taken up by scavenger receptors on phagocytic cells as well as CR1 and/or CR3.

Promotion of uptake by cellular receptors can be utilized to neutralize a wide variety of extracellular ligands, such as inflammatory cytokines, venomous or pathogen-derived toxins, cell signaling molecules (e.g. endocrine hormones, paracrine signals, neurologic signaling molecules, etc.), or metabolic byproducts of chemotherapeutics which would otherwise be too toxic to be utilized practically in patients. Multivalent aptamers can be bound to synthetic or purified peptides, proteins, or other antigens, and drugs or other therapeutic agents to mediate delivery to specific cell types, such as cancer cells. In another example, multivalent aptamers can be engineered to link synthetic or exogenously derived peptides or other antigens to regions of an MHC I molecule in close proximity to the binding cleft, for the purpose of presentation of exogenous antigen to artificially induce immunity or tolerance to a molecule, toxin, or pathogen of interest.

In addition to aptamers to iC3b, endogenous carrier proteins that represent an intermediate between a targeted extracellular protein and a receptor, aptamers can be made with affinity to alternate carrier proteins and theoretically also to the receptors themselves. A group of alternate endogenous carrier proteins that can be utilized to direct multivalent aptamers linked to target proteins to receptors for uptake or signaling purposes is represented by the heat shock proteins ("HSP"). As an illustration of this principle, bivalent antibodies that simultaneously target the FcγIIIA receptor (CD16) on natural killer cells and CD30, an antigen expressed on most Hodgkin's leukemia cells, have been engineered to target cancer cells for lysis by the immune system (Arndt et al., "A Bispecific Diabody that Mediates Natural Killer Cell Cytotoxicity Against Xenotransplantated Human Hodgkin's Tumors," *Blood* 94(8):2562-8 (1999), which is hereby incorporated by reference in its entirety). Re-engineered bivalent and multivalent antibodies have been developed that include a variable region (Fv) with affinity for the surface of a cancer cell with a fragment of the Fc receptor as a means of targeting cancer cells for destruction by the immune system including the complement pathway (Kortt et al., "Dimeric and Trimeric Antibodies: High Avidity scFvs for Cancer Targeting," *Biomolecular Engineering* 18(3):95-108 (2001), which is hereby incorporated by reference in its entirety). However, these bi- and multivalent antibodies do not function to reduce levels of specific antigens by promoting their uptake by receptors.

Uptake by receptors can be promoted by aptamers exploiting either receptor-specific or non-specific mechanisms. In some cases, receptors function to clear endogenous ligands by means of non-specific endocytosis via binding to clathrin—coated pits. Aptamers to non-receptor specific endocytosis motifs can be used as bridging molecules and/or markers.

As with the GFP—C3 bifunctional aptamer described in the examples below, multivalent aptamers can be used to bridge exogenously derived extracellular antigens to cellular receptors whose major function involves signaling rather than uptake. For example, the major histocompatibility complex ("MHC") class I molecules HLA-A, HLA-B, HLA-C, HLA-D, HLA-E, and HLA-G function in peptide presentation by binding peptides derived from endocytosed proteins in pockets of their antigen-binding clefts (Sullivan et al., "A Structural Perspective On MHC Class Ib Molecules In Adaptive Immunity," *Trends In Immunology* 27(9):413-20 (2006), which is hereby incorporated by reference in its entirety). A soluble form of an MHC I receptor has been generated previously (Goldstein et al., "Purified MHC Class I and Peptide Complexes Activate Naive CD8+ T Cells Independently of the CD28/B7 and LFA-1/ICAM-1 Costimulatory Interactions," *J. Immunol.* 160(7):3180-7 (1998), which is hereby incorporated by reference in its entirety). Multivalent aptamers can be engineered to link synthetic or exogenously derived peptides or other antigens to regions of an MHC I molecule in close proximity to the binding cleft for the purpose of presentation of exogenous antigen to artificially induce immunity or tolerance to a molecule, toxin, or pathogen of interest. Similarly, known peptide motifs for receptor-specific endocytosis, such as NPXY (where Y represents any amino acid), and motifs that direct non-clathrin associated endocytosis, including strings of alternating acidic and nonacidic residues (termed the EX motif) or a string of acidic residues (termed the EE motif), can be used to direct multivalent aptamers bound to target molecules to the clathrin or non-clathrin associated pathways of endocytosis (Gong et al., "Identification and Characterization of a New Class of Trafficking Motifs for Controlling Clathrin-independent Internalization and Recycling," *J. Biol. Chem.* 282(17):13087-97 (2007), which is hereby incorporated by reference in its entirety).

Accordingly, molecules different from the complement protein C3 or biologically active proteolytic product thereof to which a second domain of a nucleic acid aptamer may bind may include, without limitation, target proteins and other target molecules. Suitable target proteins include, without limitation, cell surface proteins, cancer cell-specific surface proteins, and extracellular proteins.

A number of previously identified aptamers can be incorporated into the bi-functional aptamers of the present invention as the second function (or domain). Exemplary aptamers include, without limitation: VEGF-binding aptamers (Carrasquilo et al., "Controlled Delivery of the Anti-VEFG Aptamer EYE001 with Poly(lactic-co-glycolic)Acid Microspheres," *Investigative Ophthalmology & Visual Science* 44:290-299 (2003), which is hereby incorporated by reference in its entirety); PSMA aptamers (Farokhzad et al., "Nanoparticle-Aptamer Bioconjugates: A New Approach for Targeting Prostate Cancer Cells," *Cancer Res.* 64:7668-7672 (2004); PCT Patent Application Publication No. WO 2006/096754; Chu et al., "Aptamer Mediated siRNA Delivery," *Nucl. Acids Res.* 34:e73 (2006); Lupoid et al., "Identification and Characterization of Nuclease-stabilized RNA Molecules That Bind Human Prostate Cancer Cells via the Prostate-specific Membrane Antigen," *Cancer Res.* 62:4029-4033 (2002), which are hereby incorporated by reference in their entirety); leukemia aptamers (Shangguan et al., "Aptamers Evolved from Cultured Cancer Cells Reveal Molecular Differences of Cancer Cells in Patient Samples," *Clinical Chemistry* 53:1153-1155 (2007), which is hereby incorporated by reference in its entirety); aptamers specific for Burkitt's lymphoma cells (Mallikaratchy et al., "Aptamer Directly Evolved from Live Cells Recognizes Membrane Bound Immunoglobin Heavy Mu Chain in Burkitt's Lymphoma Cells," *Molecular & Cellular Proteomics* 6.12:2230-2237 (2008), which is hereby incorporated by reference in its entirety); EGFr aptamers (Chen et al., "Inhibition of Heregulin Signaling by an Aptamer that Preferentially Binds to the Oligomeric Form of Human Epidermal Growth Factor Receptor-3," *Proc. Nat'l Acad. Sci. U.S.A.* 100:9226-9231 (2003), which is hereby incorporated by reference in its entirety); liver cancer specific aptamers (Shangguan et al., "Identification of Liver Cancer-specific Aptamers Using Whole Live Cells," *Anal. Chem.* 80:721-728 (2008), which is hereby incorporated by reference in its entirety); aptamers targeting human epidermal growth factor receptor-3 (HER3) (Chen et al., "Inhibition or Heregulin Signaling by an Aptamer that Preferentially Binds to the Oligomeric Form of Human Epidermal Growth Factor Receptor-3," *Proc. Natl. Acad. Sci. USA* 5:100(16):9226-31 (2003), which is hereby incorporated by reference in its entirety); aptamers targeting human receptor tyrosine kinases, such as RET (Cerchia et al., "Neutralizing Aptamers from Whole-Cell SELEX Inhibit the RET Receptor Tyrosine Kinase," *PLoS Biology* 3(4):e123 (2005), which is hereby incorporated by reference in its entirety); aptamers targeting human serine/threonine kinases, such as Raf-1 (Kimoto et al., "Anti-(Raf-1) RNA Aptamers that Inhibit Ras-induced Raf-1 Activation," *Eur. J. Biochem.* 269:697-704 (2002), which is hereby incorporated by reference in its entirety) and VEGF165 (Ruckman et al., "2'-Fluoropyrimidine RNA-based Aptamers to the 165-Amino Acid Form of Vascular Endothelial Growth Factor (VEGF$_{165}$)," *J. Biol. Chem.* 273 (32):20556-67 (1998), which is hereby incorporated by reference in its entirety); and aptamers targeting platelet-derived growth factor receptor (Pietras et al., "Inhibition of Platelet-derived Growth Factor Receptors Reduces Interstitial Hypertension and Increases Transcapillary Transport in Tumors," *Cancer Res.* 61(7):2929-34 (2001); Floege et al., "Novel Approach to Specific Growth Factor Inhibition in vivo: Antagonism of Platelet-derived Growth Factor in Glomerulonephritis by Aptamers," *Am. J. Pathol.* 154(1):169-79 (1999), which are hereby incorporated by reference in their entirety). Other aptamers useful in the methods of the invention are publicly available at the Aptamer Database (Lee et al., "Aptamer Database," *Nucl. Acids Res.* 32:D95-D100 (2004), which is hereby incorporated by reference in its entirety).

Exemplary aptamers useful for targeting an angiogenic cell type present, for example, in tumors, include, without limitation, EYE0001, and those that target angiopoietin-2 (White et al., "Inhibition of rat corneal angiogenesis by a nuclease-resistant RNA aptamer specific for angiopoietin-2." *Proc. Natl. Acad. Sci. USA* 100(9):5028-33 (2003), which is hereby incorporated by reference in its entirety) and pigpen (Blank et al., "Systematic Evolution of a DNA Aptamer Binding to Rat Brain Tumor Microvessels. Selective Targeting of Endothelial Regulatory Protein Pigpen," *J. Biol. Chem.* 276(19):16464-8 (2001), which is hereby incorporated by reference in its entirety).

In addition, aptamers can be developed according to methods described herein to bind tumor-specific markers. For example, markers bound by the tumor-specific aptamers of the invention include, but are not limited to, those known in the art to be present on CA-125 (e.g., Genbank Accession No. NP_078966); gangliosides G(D2), G(M2), and G(D3); CD20 (e.g., Genbank Accession No. Pl 1836); CD52 (e.g., Genbank Accession No. NP_001794); CD33 (e.g., Genbank Accession No. NP_001763); Ep-CAM (e.g., Genbank Accession No. Pl 16422); CEA (e.g., Genbank Accession No. AAA51972); bombesin-like peptides (e.g., NP_002082, NP_001012530); prostate specific antigen (PSA) (e.g., Genbank Accession No. CAD30844, CAD54617, CAD30845); prostate-specific membrane antigen (PSMA) (e.g., Genbank Accession No. AAC83972); HER2/neu (e.g., Genbank Accession No. AAD56009); epidermal growth factor receptor (e.g., Genbank Accession No. 1006266A); erbB2 (e.g., Genbank Accession No. AAD56009); erbB3 (e.g., Genbank Accession No. P21860); erbB4 (e.g., Genbank Accession No. DAA00042, NP_039250); CD44v6 (e.g., Genbank Accession No. AAB13626, AAB13622, AAB13623); Ki-67 (e.g., Genbank Accession No. CAA46519, CAA46520); VEGF (e.g., Genbank Accession No. AAA35789); VEGFRs (e.g., Genbank Accession No. CAA61916); VEGFR3 (e.g., Genbank Accession No. AAO89505); estrogen receptors (e.g., Genbank Accession No. P3372); Lewis-Y antigen, TGβ1 (e.g., Genbank Accession No. AAX59023); IGF-I receptor (e.g., Genbank Accession No. NP_000866); EGF (e.g., Genbank Accession No. NP_001954); EGFa; c-Kit receptor (e.g., Genbank Accession No. NP_002825, AAB21235); transferrin receptor (e.g., Genbank Accession No. NP_003225); IL-2R (e.g., Genbank Accession No. NP_000869); CO17-1A (Oredipe et al., "Lack of Effect of Recombinant Human Interferon-alpha 2b on Expression of 17-1A Antigen on Human Colon Cancer Cells," *Hybridoma* 11(5):607-15 (1992), which is hereby incorporated by reference in its entirety); tumor-associated antigen MUC1 (e.g., Genbank Accession No. NP_001018017); TGF beta receptor (e.g., Genbank Accession No. NP_004603, NP_003234); and TGF beta (e.g., Genbank Accession No. NPJ_00651, NP_003230). Each of the above-identified Genbank Accessions is hereby incorporated by reference in its entirety. Aptamers of the present invention can recognize tumors derived from a wide variety of tissue types including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain.

Generation of aptamers specific for cancer cells has been previously described in which a modified SELEX procedure is used, with cancer cells providing one selection criteria and a substantially similar non-cancerous cell is used for negative selection (Tang et al., "Selection of Aptamers for Molecular Recognition and Characterization of Cancer Cells," *Anal. Chem.* 79(13):4900-7 (2007); Shangguan et al., "Identification of Liver Cancer-specific Aptamers Using Whole Live Cells," *Anal. Chem.* 80(3):721-8 (2008); Phillips et al., "Applications of Aptamers in Cancer Cell Biology," *Anal. Chim. Acta* 621(2):101-8 (2008), each of which is hereby incorporated by reference in its entirety).

Another aspect of the present invention relates to a molecular complex formed upon binding of a nucleic acid aptamer at its first domain to a complement protein C3 or biologically active proteolytic product thereof. In a preferred embodiment, the aptamer binds C3b or iC3b at its first domain. When the nucleic acid aptamer includes a second domain that binds to a molecule different from the complement protein C3 or biologically active proteolytic product thereof, the molecular complex also includes a target protein bound to the nucleic acid aptamer at the second domain. To the extent that the target protein is a cell surface protein, the molecular complex can be bound to the cell surface via binding of the nucleic acid aptamer to the cell surface protein. According to this aspect of the present invention, the cell may either be ex vivo or in vivo.

As noted above, in certain embodiments, it may be desirable for the bi-functional aptamer to include a plurality of second domains, i.e., be multi-valent for the target protein. This allows the molecular complexes to include two or more copies of the target protein per complex, which can enhance the efficacy of bi-functional aptamers for clearing target proteins from an environment, as discussed hereinafter.

A further aspect of the present invention is directed to a method of inhibiting activity of complement protein C3 or biologically active proteolytic products thereof. This method involves providing a nucleic acid aptamer that binds to and inhibits complement protein C3 or biologically active proteolytic products thereof, and contacting the complement protein C3 or biologically active proteolytic products thereof with the nucleic acid aptamer under conditions effective to bind to the complement protein C3 or biologically active proteolytic product thereof and thereby inhibit activity thereof.

The inhibitory effect of aptamers can be tested by well-established in vitro assays of complement function. One example is the functional hemolytic assay, which provides information on complement function as a whole. The total hemolytic complement assay ($CH_{50}$) measures the activity of the classical pathway, which depends on the sequential activation of the classical pathway components (C1 through C9) to lyse sheep erythrocytes that have been sensitized with optimal amounts of rabbit anti-sheep erythrocyte antibodies. The alternative pathway $CH_{50}$ assay (rabbit $CH_{50}$ or $APCH_{50}$) measures the ability of the alternative pathway and the MAC to lyse rabbit erythrocytes. One $CH_{50}$ or $APCH_{50}$ unit is defined as the quantity or dilution of serum required to lyse 50% of the red cells in the test. Typically, to assess complement activation, a sample, such as human serum or human plasma, is treated in the presence or absence of increasing concentrations of an aptamer (with RNase inhibitor if natural RNA is used). The aptamer-treated sample is subsequently mixed with sheep's red blood cells that have been activated or sensitized with IgG. A water-only sample mixed with sheep red blood cells can act as a total lysis control in order to accurately assess percent lysis of the samples analyzed. The lysing reaction can be stopped by addition of 0.15M NaCl to the sample. Lysis of the red blood cells, induced by the activation of the terminal components of the complement pathway, is assessed by measuring the release of hemoglobin by optical density ("OD") readings of the samples at 415 nm.

Contacting a complement protein C3 or biologically active proteolytic product thereof with the nucleic acid aptamer may be carried out either ex vivo or in vivo.

A further aspect of the present invention is directed to a method of promoting opsonization of a cell. This method involves providing a nucleic acid aptamer having a first domain that binds to a biologically active proteolytic product of complement protein C3 and a second domain that binds to a cell surface protein of the target cell. Upon binding of the cell surface protein on a cell with the aptamer, the cell effectively becomes labeled with a biologically active proteolytic product of complement protein C3 (C3b/iC3b), thereby promoting opsonization of the cell. Opsonization is the process in which opsonins, such as antibodies or complement components, tag pathogens for recognition by neutrophils and macrophages. Opsonization facilitates removal of antigens from the circulation by macrophages in liver and spleen, and from the tissues by monocytes and neutrophils. Human C3 is the most abundant complement protein in serum (1.2 mg/ml), and low levels of C3b/iC3b are constitutively available as part of the alternative pathway of complement activation involved in innate immune responses (Carroll et al., "The Role of Complement and Complement Receptors in Induction and Regulation of Immunity," *Annual Review of Immunology* 16:545-568 (1998), which is hereby incorporated by reference in its entirety). At any given time, about 0.5% of the total C3 present in fresh human plasma is in its hydrolyzed form (Sahu et al., "Structure and Biology of Complement Protein C3, a Connecting Link between Innate and Acquired Immunity," *Immunological Reviews* 180:35-48 (2001), which is hereby incorporated by reference in its entirety). C3b is preferentially cleared by the complement receptor CR1 and iC3b by CR3. Enhancement of the immune response to targeted proteins via linkage to C3b has been demonstrated previously (Villiers et al., "Covalent Binding of C3b to Tetanus Toxin: Influence on Uptake/Internalization of Antigen by Antigen-specific and Non-specific B Cells," *Immunology* 89:348-355 (1996); Villiers et al., "Amplification of the Antibody Response by C3b Complexed to Antigen through an Ester Link," *J. Immunol.* 162:3647-3652 (1999); Villiers et al., "Improvement of Long-lasting Response and Antibody Affinity by the Complexation of Antigen with Complement C3b," *International Immunology* 15:91-95 (2003), which are hereby incorporated by reference in its entirety). Bi-functional polyvalent aptamers with high affinity to both a target and C3b/iC3b can therefore promote clearance of the target by either CR1 or CR3. If the target is on the surface of a cancer cell, bi-functional aptamers will increase the deposition of C3b/iC3b on the cell and help induce or enhance complement-mediated cytotoxicity.

From the perspective of macrophages and other phagocytes, the primary challenge is to discriminate a large number of potential pathogens from self components using a limited number of phagocytic receptors, a problem further compounded by the propensity of pathogens to mutate. To cope with this situation, macrophages evolved two types of receptors. The first type of receptor directly recognizes conserved molecular patterns on pathogens, which have essential roles in pathogen biology but are not found in higher eukaryotes (host or "self"). These molecular patterns, such as mannans in the yeast cell wall, are limited in number and are recognized by the receptors in a manner similar to the way lectins activate the complement system. The second type of receptor introduces diversity to the repertoire of recognition by indirect binding through adaptor molecules, called opsonins, such as antibodies or complement components. For example, the IgG antibodies bind antigens with exquisite specificity through the Fab region and interact with Fc gamma receptors (FcγR) on phagocytes through the generic Fc region to enable the internalization of the coated particles (Indik et al., "The Molecular Dissection of Fc Gamma Receptor Mediated Phagocytosis," *Blood* 86:4389-4399 (1995), which is hereby incorporated by reference in its entirety). There are at least three gene superfamilies of complement receptors, and opsonization by C3b/iC3b provides a moderate degree of diversification for receptor-mediated phagocytosis (van Lookeren et al., "Macrophage Complement Receptors and Pathogen Clearance," *Cellular Microbiology* 9:2095-2102 (2007), which is hereby incorporated by reference in its entirety).

Opsonins are molecular adaptors; and antibodies, as described above, are better adaptors than C3b/iC3b. Similar to the Fc region of antibodies, C3b/iC3b can be recognized by only a few generic receptors that mediate physiological effects. However, the recognition and linkage of C3b/iC3b with the particles they tag is much less specific and less efficient than that by the Fab region of an antibody. Instead of non-covalent binding based on matching shape and charge distribution, C3b uses its thioester as a "warhead" for covalent attachment to the particle being opsonized. Although C3b shows a preference for certain hydroxyl groups, it does not have the intrinsic ability to discriminate between self and non-self. Only 10% of C3b molecules become linked to antigenic surfaces through the ester moiety, and the other 90% react with water and are released into the aqueous phase (Sahu et al., "Structure and Biology of Complement Protein C3, a Connecting Link Between Innate and Acquired Immunity," *Immunological Reviews* 180:35-48 (2001), which is hereby incorporated by reference in its entirety).

The present invention equips C3b/iC3b with a secondary adaptor having higher specificity and efficiency, with the intention to tag certain unwanted "self" proteins or cells as "foreign" to elicit an immune response against them. The specificity and efficiency of target recognition by aptamers would rival or exceed the paratopes of antibodies, and turn a liability of C3b—not being able to distinguish the self from the foreign—into an advantage. Aptamers against their targets are raised in vitro from a combinatorial sequence pool. This process is conceptually similar to the way Fab regions are selected and amplified in vivo, but a much larger shape space is searched. To construct a secondary adaptor for C3b/iC3b, an aptamer raised against a target will be covalently connected to an aptamer that binds C3b/iC3b to form a bi-functional aptamer that bridges the target and the C3b/iC3b molecule. In this arrangement, the C3b/iC3b molecule and the bi-functional aptamer together would function with specificity and efficiency similar to an antibody in the process of opsonization, and with the additional capability of tagging unwanted "self" as "foreign." The unwanted "self" components being tagged include, but are not limited to, oncogenic proteins and cancer cells.

Because the aptamer that recognizes C3b/iC3b serves as the "utility" moiety of the molecule to connect the specific "targeting" moiety to the "utility molecule" C3b/iC3b, this aptamer should not interfere with functions of C3b/iC3b, such as their capability of being recognized by their cognate receptors on the surface of effector cells. To find an aptamer fitting for the "utility" described here and to optimize the aptamer-C3b/iC3b connection, aptamers will be screened for discrete sites on the surface of C3b/iC3b to identify those that do not inhibit complement function and can be recognized by receptors such as CR1 or CR3.

According to one embodiment, the cell to be opsonized can be a cancer cell, in which case the cell surface protein is preferably a cancer cell-specific surface protein (such as one of those listed above) and the second domain of the aptamer is specific for that surface protein.

Thus, another aspect of the present invention is directed to a method of treating cancer in a patient. This method involves providing a nucleic acid aptamer having a first domain that binds to a biologically active proteolytic product of complement protein C3 and a second domain that binds to a molecule different from the biologically active proteolytic product of complement protein C3, where the molecule different from the biologically active proteolytic product of C3 is a cell surface protein of a cancer cell. The nucleic acid aptamer is administered to a patient under conditions effective to promote opsonization of the cancer cell and thereby treat the patient for cancer.

Cancer cells originate from normal cells ("self"), and mutate to become insensitive to normal growth control, to become immortal, to be able to invade surrounding tissue and to be able to form metastases at a distant place. The development of cancer is accompanied by qualitative and quantitative changes in the proteins expressed on the cancer cell surface. Some of these changes are prominent and distinctive enough to be used as markers to identify the cancer cells. Some markers can be recognized as non-self by the immune system due to mutation and thus serve as tumor antigens (Gelderman et al., "Complement Function in mAb-mediated Cancer Immunotherapy," *Trends in Immunology* 25:158-164 (2004); Macor et al., "Complement as Effector System in Cancer Immunotherapy," *Immunology Letters* 111:6-13 (2007), which are hereby incorporated by reference in their entirety).

These markers, when recognized and bound by the targeting moiety of bi-functional opsonizing aptamers, can recruit C3b/iC3b to the surface of cancer cells.

In choosing a cancer cell surface marker as a target for aptamers, these markers should preferably be expressed exclusively on the majority of cancer cells, and in any case the level of expression on tumor cells should be significantly higher than that on normal cells from which the tumor has originated. It is also desirable that a specific marker is expressed on metastatic cells as the primary tumor is often removed surgically, and metastatic growth and recurrence of the tumor are often the cause of death.

Exemplary cancer cell markers are identified above, and aptamers against any such cancer cell surface proteins can be used to label the cancer cells for opsonization. As discussed herein, aptamers have been raised against a number of these cancer cell targets.

When the aptamers of the present invention are administered to treat or prevent a cancerous condition, a pharmaceutical composition containing the aptamer can also contain, or can be administered in conjunction with, other therapeutic agents or treatment regimens presently known or hereafter developed for the treatment of various types of cancer. Examples of other therapeutic agents or treatment regimens include, without limitation, radiation therapy, chemotherapy, surgical intervention, and combinations thereof.

One consideration in carrying out this and other methods of the present invention is that to produce aptamers that are functional in vivo, in vitro selection must be performed against targets in their native conformation, a prerequisite that may be difficult to achieve for membrane proteins (Pestourie et al., "Comparison of Different Strategies to Select Aptamers Against a Transmembrane Protein Target," *Oligonucleotides* 16:323-335 (2006), which is hereby incorporated by reference in its entirety). As a result, fewer aptamers have been generated for membrane proteins than soluble targets. Because the application of most aptamers for membrane proteins is the recognition of their targets on cell surface, a straightforward approach is to raise the aptamer against the recombinant soluble extracellular domain of the target protein. This approach has generated a few high-quality aptamers, notably those for PSMA (Lupold et al., "Identification and Characterization of Nuclease-stabilized RNA Molecules that Bind Human Prostate Cancer Cells via the Prostate-specific Membrane Antigen," *Cancer Res.* 62:4029-4033 (2002), which is hereby incorporated by reference in its entirety) and human epidermal growth factor receptor-3 (EGFR-3) (Chen et al., "Inhibition of Heregulin Signaling by an Aptamer that Preferentially Binds to the Oligomeric Form of Human Epidermal Growth Factor Receptor-3." *Proc. Nat'l Acad. Sci. U.S.A.* 100:9226-9231 (2003), which is hereby incorporated by reference in its entirety). However, using recombinant extracellular domains of membrane protein sometimes yields aptamers with low or no affinity to the protein in a cell surface environment (Pestourie et al., "Comparison of Different Strategies to Select Aptamers Against a Transmembrane Protein Target," *Oligonucleotides* 16:323-335 (2006), which is hereby incorporated by reference in its entirety). To solve this problem, some investigators have used intact cells as targets to select aptamers (Shangguan et al., "Aptamers Evolved from Live Cells as Effective Molecular Probes for Cancer Study," *Proc. Nat'l Acad. Sci. U.S.A.* 103: 11838-11843 (2006); Cerchia et al., "Neutralizing Aptamers from Whole-cell SELEX Inhibit the RET Receptor Tyrosine Kinase," *PLoS Biology* 3:e123 (2005), which are hereby incorporated by reference in their entirety). In this type of "fishing" experiment, while aptamers may be isolated without prior target identification, it is difficult, if not impossible, to control the enrichment dynamics of aptamers for a particular target molecule. There are vast numbers of molecules exposed to the aptamer candidate pool serving as unintended targets, which may select undesirable aptamers that will come to dominate the selected pool and prevent the isolation of desirable aptamers for the intended target. A third approach is to use membrane preparations with naturally enriched target (e.g., *Torpedo californica* electroplax membrane (Ulrich et al., "In Vitro Selection of RNA Molecules that Displace Cocaine From the Membrane-bound Nicotinic Acetylcholine Receptor," *Proc. Nat'l Acad. Sci. U.S.A.* 95:14051-14056 (1998), which is hereby incorporated by reference in its entirety) and rat forebrain membrane (Cui et al., "Selection of Stable RNA Molecules that Can Regulate the Channel-opening Equilibrium of the Membrane-bound Gamma-aminobutyric Acid Receptor," *Biochemistry* 43:16442-16449 (2004), which is hereby incorporated by reference in its entirety) in SELEX experiments. But in general, this type of resource is not available for any given membrane protein. To avoid the experimental difficulties and problems associated with these approaches, a novel method was pioneered to use target molecule-enriched membrane preparation to select aptamers.

One preferred method has three components that extend the conventional method of SELEX. First, it is desirable to achieve the highest surface density possible for the target protein per cell mass by expressing it in a recombinant form using a system with a dramatically increased level of production. The expression construct for the target protein, on a vector containing the SV40 replication origin, will be introduced into human embryonic kidney 293S (HEK 293S) cells using a standard transient transfection protocol. A SV40 large T-antigen (Tag) gene is co-expressed in these cells to boost the expression of the target protein up to 7-fold at the single-cell level (Huang et al., "Enhancing Protein Expression in Single HEK 293 Cells," *J. Neurosci. Methods* 142:159-166 (2005), which is hereby incorporated by reference in its entirety). Second, a cell membrane preparation is used rather than intact cells as the target for selection. Two days after transfection, cells are harvested, washed, and homogenized. After low-speed centrifugation to get rid of cell debris, the supernatant will be subject to ultracentrifugation to collect the cell membrane fragment pellet. In this preparation the target density can reach 0.6 pmol/mg (Huang et al., "RNA Aptamers Selected Against the GluR2Glutamate Receptor Channel," *Biochemistry* 46:12648-12655 (2007), which is hereby incorporated by reference in its entirety). Third, negative selection is used to winnow out aptamers to all non-target molecules that may be present in the target-containing membrane preparation. The same kind of membrane fragments for parental un-transfected cells are prepared without target expression. After each selection cycle, RNAs bound to the target preparation will be retrieved and then the RNA pool will be incubated with the membrane preparation lacking target expression. Only RNAs that do not bind to this latter preparation will be collected for further cycles of amplification and selection. This method is convenient to use and entails minimal additional procedures beyond standard protocols. Compared to using cell lines permanently expressing the protein of interest, transient expression is simple and time saving. Thorough mixing of the membrane fragments and the aptamer candidate pool can be achieved by keeping the reaction mixture on a nutator. A conventional partitioning device, such as a nitrocellulose filter, can be used without modification.

Figure 3:
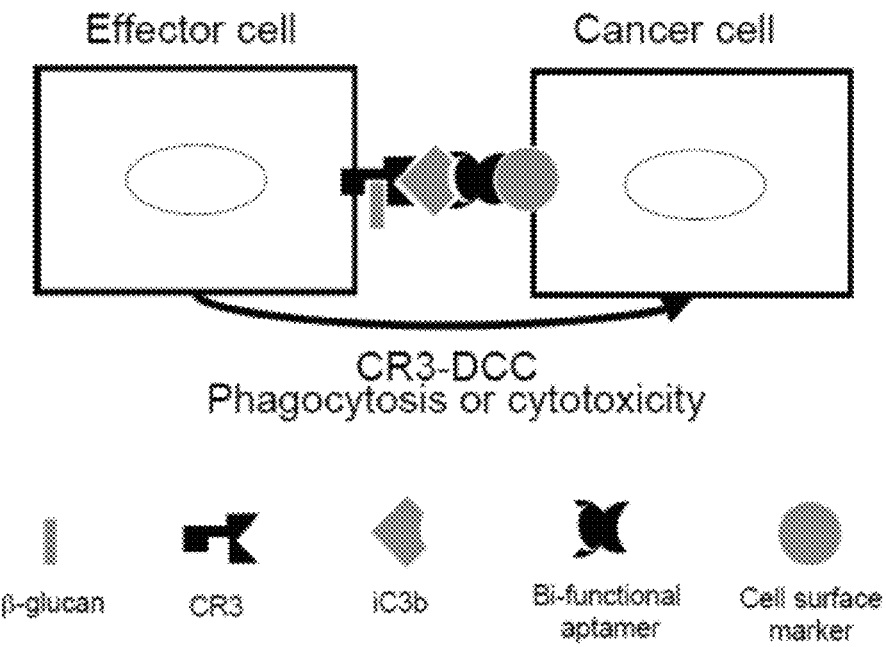
FIG. 3 is a schematic illustration of the proposed mechanism of aptamer-mediated CR3-dependent cellular cytotoxicity ("CR3-DCC"). The bi-functional aptamer induces the deposition of iC3b on the surface of cancer cells through binding to a surface protein marker. Ligation of iC3b by β-glucan primed CR3 on the surface of an effector cell induces cytotoxicity or phagocytosis by the effector cell.

There are essentially two mechanisms by which complement causes damage to cancer cells: direct killing by the membrane attack complex ("MAC") and cell-mediated cytotoxicity. One of the problems to solve in exploiting these mechanisms in cancer therapy is to counter the inhibitory effect of membrane-bound complement regulatory proteins ("mCRPs") that are often overexpressed on tumor cells. The present invention focuses on the second mechanism to generate iC3b-opsonized tumor cells and to facilitate their elimination by effector cells. More specifically, increasing the deposition of iC3b on the surface of tumor cells will overwhelm the mCRPs and trigger cytotoxicity through CR3 with the help of an adjuvant, as shown in FIG. 3.

Because C3 and other complement components lack the intrinsic ability to discriminate between self and non-self, cells must distinguish themselves by expressing mCRPs to avoid homologous complement attack. Overexpression of mCRPs is an important strategy of immune evasion by tumor cells (Fishelson et al., "Obstacles to Cancer Immunotherapy Expression of Membrane Complement Regulatory Proteins (mCRPs) In Tumors," *Molecular Immunology* 40:109-123 (2003), which is hereby incorporated by reference in its entirety). In vitro studies have demonstrated potent inhibitory effects of mCRPs on mAb-induced C3b deposition, C5a generation, and MAC-mediated lysis. For example, CD46 is a cofactor for factor I-mediated degradation of C3b and C4b to iC3b and iC4b, respectively, preventing formation of new convertase (Niehans et al., "Human Carcinomas Variably Express the Complement Inhibitory Proteins CD46 (Membrane Cofactor Protein), CD55 (Decay-accelerating Factor), and CD59 (Protectin)," *Am. J. Pathology* 149:129-142 (1996), which is hereby incorporated by reference in its entirety). Tumor cells can also bind soluble complement inhibitors from serum such as Factor H by up-regulating sialic acid-rich proteins (Fedarko et al., "Elevated Serum Bone Sialoprotein and Osteopontin In Colon, Breast, Prostate, and Lung Cancer," *Clin. Cancer Res.* 7:4060-4066 (2001), which is hereby incorporated by reference in its entirety). Factor H regulates complement activation on self-cells by means of both its cofactor activity for factor I-mediated C3b cleavage, and decay accelerating activity against the alternative pathway C3 convertase, C3bBb. Blocking or overwhelming mCRP function may enhance the complement susceptibility of tumor cells. However, the widespread expression of mCRPs on normal cells makes their tumor-exclusive blockade difficult in vivo without a specific and efficient addressing device to guide them to tumor cells.

Instead, two approaches are taken to increase the deposition of the predominant C3-derived opsonin, iC3b, on tumor cells, in the hope of utilizing its receptor CR3 (CD11b-CD18) on the surface of phagocytes and NK cells to mediate CR3-dependent cellular cytotoxicity ("CR3-DCC") (Ross et al., "Therapeutic Intervention with Complement and Beta-glucan In Cancer," *Immunopharmacology* 42:61-74 (1999), which is hereby incorporated by reference in its entirety). First, aptamers for multiple cell surface targets are utilized. These aptamers, after being incorporated into bi-functional aptamers, can be used together as a cocktail to recruit more C3b/iC3b to the cell surface. Second, within a single bi-functional aptamer molecule, more than one aptamer for C3b/iC3b can be connected to a single aptamer for the target, thus increasing the number of C3b/iC3b molecules on the cell surface. Moreover, for each target more than one aptamer may be isolated. With aptamers recognizing different "epitopes" of a target, composite aptamers can be generated with chelating or cross-linking activities to manipulate the density of iC3b recruited to the cell surface.

CR3-DCC is normally reserved for killing fungi that bear β-glucan as an exposed component of their cell wall. Induction of cytotoxicity by iC3b-coated yeast requires the dual ligation of CR3 to both cell wall β-glucan and iC3b: β-glucan binds to a C-terminal lectin domain of CD11b to prime CR3 for cytotoxic degranulation responses after it also binds iC3b by an N-terminal I-domain binding site of CD11b (Vetvicka et al., "Soluble Beta-glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-opsonized Target Cells," *J. Clin. Investigation*, 98:50-61 (1996); Xia et al., "The Beta-glucan-binding Lectin Site of Mouse CR3 (CD11b/CD18) and Its Function In Generating a Primed State of the Receptor that Mediates Cytotoxic Activation In Response to iC3b-opsonized Target Cells," *J. Immunol.* 162:2281-2290 (1999), which are hereby incorporated by reference in their entirety). Although tumor cells, like other host cells, lack β-glucan as a surface component, β-glucan can be supplied as an adjuvant to manipulate the CR3 so it will be primed to trigger cytotoxicity of iC3b-coated tumor cells (Ross et al., "Therapeutic Intervention with Complement and Beta-glucan In Cancer," *Immunopharmacology* 42:61-74 (1999), which is hereby incorporated by reference in its entirety). Mice injected intravenously with combined soluble yeast β-glucan and anti-tumor complement-activating mAbs exhibited tumor regression and long-term survival; this therapeutic effect did not occur in mice deficient in either C3 or CR3, indicating the requirement for iC3b deposited on tumor cells (Yan et al., "Beta-glucan, a "Specific" Biologic Response Modifier that Uses Antibodies to Target Tumors for Cytotoxic Recognition by Leukocyte Complement Receptor Type 3 (CD11b/CD18)," *J. Immunol.* 163:3045-3052 (1999); Hong et al., "Beta-glucan Functions as an Adjuvant for Monoclonal Antibody Immunotherapy by Recruiting Tumoricidal Granulocytes as Killer Cells," *Cancer Res.* 63:9023-9031 (2003), which are hereby incorporated by reference in their entirety).

Some large molecular size β-glucans, such as that from barley, can also function as adjuvant when given orally to mice (Cheung et al., "Orally Administered Beta-glucans Enhance Anti-tumor Effects of Monoclonal Antibodies," *Cancer Immunology and Immunotherapy* 51:557-564 (2002), which is hereby incorporated by reference in its entirety). To explore the feasibility of aptamer-mediated CR3-DCC, cell-based assays will be used in vitro to test whether β-glucan can enable CR-positive effector cells to eliminate bi-functional aptamer bound tumor cells.

There are two primary mechanisms through which particles are internalized by cells. Small particles (<0.5 µm in diameter), such as macromolecules and viruses, enter cells through receptor-mediated endocytosis, which is a clathrin-based mechanism. Large particles (>0.5 µm) are taken up into cells by actin-dependent phagocytosis. C3b receptors are involved in both types of internalization (Aderem et al., "Mechanisms of Phagocytosis in Macrophages," *Annual Rev. Immunology* 17:593-623 (1999), which is hereby incorporated by reference in its entirety). Endocytosis of C3b receptors by human polymorphonuclear leukocytes and monocytes has been observed using anti-C3b receptor antibodies. Fluorescently labeled antibodies located C3b receptors in coated endocytic pits and coated vesicles within the cytoplasm, indicating that C3b receptors may directly mediate endocytosis (Fearon et al., "Membrane Distribution and Adsorptive Endocytosis by C3b Receptors on Human Polymorphonuclear Leukocytes," *J. Exp. Med.* 153:1615-1628 (1981); Abrahamson et al., "Endocytosis of the C3b Receptor of Complement Within Coated Pits In Human Polymorphonuclear Leukocytes and Monocytes," *Laboratory Investigation* 48:162-168 (1983), which are hereby incorporated by reference in their entirety).

In the classical pathway of complement activation, soluble antigens are cleared from the body by formation of immune complexes including antigen, antibody, and complement components such as C3b and iC3b. Opsonization with antibody and complement components facilitates removal of antigens from the circulation by macrophages in the liver and spleen, and from the tissues by monocytes and neutrophils. C3b is preferentially cleared by the complement receptor CR1 and iC3b by CR3 (Yan et al., "Critical Role of Kupffer Cell CR3 (CD11b/CD18) In the Clearance of IgM-opsonized Erythrocytes or Soluble Beta-glucan," *Immunopharmacology* 46:39-54 (2000), which is hereby incorporated by reference in its entirety). Enhancement of the immune response to targeted proteins via linkage to C3b has been demonstrated previously (Villiers et al., "Covalent Binding of C3b to Tetanus Toxin: Influence on Uptake/internalization of Antigen by Antigen-specific and Non-specific B Cells," *Immunology* 89:348-355 (1996); Villiers et al., "Amplification of the Antibody Response by C3b Complexed to Antigen Through an Ester Link," *J. Immunol.* 162:3647-3652 (1999); Villiers et al., "Improvement of Long-lasting Response and Antibody Affinity by the Complexation of Antigen with Complement C3b," *International Immunology* 15:91-95 (2003), which are hereby incorporated by reference in their entirety). Bi-functional polyvalent aptamers that target extracellular proteins can therefore promote clearance of these target proteins by either CR1 or CR3. A particularly desirable type of target molecules is the unwanted "self" proteins. A particularly desirable type of unwanted "self" proteins is cancer-associated proteins. An example of cancer related proteins is vascular endothelial growth factor ("VEGF") and others identified herein. Other aptamers against extracellular targets are described, for example, in Nimjee et al., "Aptamers: An Emerging Class of Therapeutics," *Annual Review of Medicine* 56:555-583 (2005) and Pestourie et al., "Aptamers Against Extracellular Targets for In Vivo Applications," *Biochimie* 87:921-930 (2005), which are hereby incorporated by reference in their entirety.

Endocytosis of aptamers has been reported previously (Homann et al., "Uptake and Intracellular Transport of RNA Aptamers In African Trypanosomes Suggest Therapeutic "Piggy-back" Approach," *Bioorg. Med. Chem.* 9(10):2571-80 (2001), which is hereby incorporated by reference in its entirety). In this study, RNA aptamers for a 42 kDa surface protein of *Trypanosoma brucei* were found to become rapidly internalized by endocytosis and are transported to the lysosome by vesicular transport. The identified internalization and transport pathway was used to target aptamer-coupled biotin molecules to the lysosome. The authors suggested that the RNAs can be used as 'piggy-back' molecules to target aptamer-coupled compounds/toxins to the lysosomal compartment of the parasite. The failure of these authors to recognize that aptamers can be used to bind to molecules that exist extracellularly and promote their clearance, rather than simply target molecules that have previously (or artificially) been coupled to the aptamer, illustrates that the present invention is not obvious to one skilled within the art. In fact, it teaches away from the invention presented herein.

Another aspect of the present invention is directed to a method of treating a disease or disorder involving undesirable cellular damage in a patient. This method involves providing a nucleic acid aptamer according to the first aspect of the present invention, where the aptamer binds to and inhibits the function of complement protein C3 or biologically active proteolytic product thereof. The nucleic acid aptamer is administered to the patient under conditions effective to treat a disease or disorder involving undesirable cellular damage in the patient.

The complement system can mediate undesirable cellular damage in many diseases and disorders. These include, but are not limited to, inflammatory or autoimmune disease, myasthenia gravis, systemic lupus erythaematosus, ischaemia-reperfusion states, hyperacute rejection of transplants, organ failure conditions (e.g., adult respiratory distress syndrome ("ARDS")), age-related macular degeneration, asthma (Taube et al., "Inhibition of Complement Activation Decreases Airway Inflammation and Hyperresponsiveness," *Am. J. Resp. Crit. Care Medicine* 168:1333-1341 (2003), which is hereby incorporated by reference in its entirety), Alzheimer's disease ("AD"), and related neurodegenerative disorders. These diseases and conditions are treatable with complement inhibitors. In particular, inactivation of C3 would lead to inhibition of C3a and C5a generation and of C5b-C9 formation, all of which are implicated in complement-mediated host cell damage (Sahu et al., "Complement Inhibitors: A Resurgent Concept in Anti-inflammatory Therapeutics," *Immunopharmacology* 49:133-148 (2000), which is hereby incorporated by reference in its entirety).

In one embodiment of this method of the present invention, the disease or disorder involves undesirable tissue remodeling. Accordingly, administering an aptamer to a patient is carried out under conditions effective to inhibit the undesirable tissue remodeling.

Tissue remodeling associated with inflammation is a central feature of most chronic human diseases including cancer, arthritis, and atherosclerosis. It is this type of tissue remodeling that is undesirable, and is intended to be inhibited by the aptamers of the present invention. Inflammatory cells participate in tissue remodeling by secreting products that promote cell migration, including cytokines such as TGFβ, growth factors such as VEGF, and enzymes that degrade the extracellular matrix ("ECM") (Nathan, "Points of Control In Inflammation," *Nature* 420(6917):846-52 (2002), which is hereby incorporated by reference in its entirety). For example, the enzyme heparanase degrades and remodels the ECM by cleaving heparan sulfate, and its activity is implicated in tumor metastasis, diabetic nephropathy, and autoimmunity (Ilan et al., "Regulation, Function and Clinical Significance of Heparanase In Cancer Metastasis and Angiogenesis," *Internat'l J. Biochem. Cell Biol.* 38(12):2018-39 (2006), which is hereby incorporated by reference in its entirety). High levels of matrix metalloproteinase activity associated with inflammation are implicated in tumor metastasis as well as atherosclerosis, coronary thrombosis, and restenosis after angioplasty (Newby, "Dual Role of Matrix Metalloproteinases (Matrixins) In Intimal Thickening and Atherosclerotic Plaque Rupture," *Physiological Reviews* 85(1):1-31 (2005); Coussens et al., "Inflammation and Cancer," *Nature* 420(6917):860-7 (2002); Libby, "Inflammation In Atherosclerosis," *Nature* 420(6917):868-74 (2002), which are hereby incorporated by reference in their entirety). Drugs targeted to effectors of inflammation therefore constitute potential therapies for a broad range of human diseases.

In an alternative embodiment, the nucleic acid aptamers of the present invention have a near-infrared emitting probe or radiolabel conjugated to the aptamer. Suitable near-infrared emitting probes include, without limitation, fluorophores, quantum dots, nanoparticles, fluorescent proteins, bioluminescent proteins, or silica nanoparticles encapsulating cyanine fluorophores. When nanoparticles are employed, preferred nanoparticles include, without limitation, gold and silver nanoparticles.

As described supra, aptamers of the present invention may be conjugated to a detectable secondary molecule, based on the precedent of the GFP-C3 aptamer described herein. Thus, another aspect of the present invention is directed to a method of imaging a tumor in a patient. This method involves administering to a patient a nucleic acid aptamer that recognizes a cancer cell-specific surface protein, where the aptamer is conjugated to an imaging label and detecting whether the conjugated imaging label is localized within any tissues of the patient.

Because human tissue is relatively transparent in the near-infrared ("NIR") range, a variety of NIR-emitting probes have been recently developed, including fluorophores, quantum dots, silver and gold nanoparticles, fluorescent and bioluminescent proteins, and silica nanoparticles encapsulating cyanine fluorophores. The organic fluorophore indocyanine green has been approved by the FDA for use in humans (Bringley et al., "Silica Nanoparticles Encapsulating Near-infrared Emissive Cyanine Dyes," *J. Colloid Interface Sci.* Sep. 7, 2007, which is hereby incorporated by reference in its entirety). In addition, multivalent aptamers can be used to detect molecular recognition events in vivo by means of quenching of fluorescent molecules or energy transfer, with an advantage similar to that of self-assembly of quantum dot-receptor complexes based on the ability to design aptamers with affinity for a designated surface material (Anikeeva et al., "Quantum Dot/peptide-MHC Biosensors Reveal Strong CD8-dependent Cooperation Between Self and Viral Antigens that Augment the T Cell Response," *Proc. Nat'l Acad. Sci. U.S.A.* 103(45):16846-51 (2006), which is hereby incorporated by reference in its entirety). Novel technologies enabling combined in vivo imaging with targeted therapy are opening new avenues for cancer treatment. Phototherapy involving metal nanoparticles is based on the ability of these nanoparticles to efficiently convert photon energy to heat energy, resulting in a dramatic release of heat from the nanoparticle to the local environment (Huo, "A Perspective on Bioconjugated Nanoparticles and Quantum Dots," *Colloids and Surfaces B. Biointerfaces* 59(1):1-10 (2007), which is hereby incorporated by reference in its entirety). In one example, targeted therapy using plasmonic gold nanoparticles with an average size of 40 nm conjugated with anti-epidermal growth factor ("EGF") antibodies has been attempted against cancer cell lines with promising results. The trial employed two oral squamous cell cancer cell lines and a control, nonmalignant line. After the cell lines were mixed with the conjugated particles, they were subjected to light from an argon laser at 514 nm. Malignant cells were killed using less than half the energy required to kill normal cells, and no cells were killed in the absence of gold particles using 4 times the level of energy used to kill malignant cells (El-Sayed et al., "Selective Laser Photo-thermal Therapy of Epithelial Carcinoma Using Anti-EGFR Antibody Conjugated Gold Nanoparticles," *Cancer Letters* 239(1):129-35 (2006), which is hereby incorporated by reference in its entirety). Similarly, aptamer-associated gold nanoparticles can be used for this type of phototherapy with lowered potential for immunogenicity.

Because iC3b is known to opsonize tumor cells and tumor margins, the aptamers described herein to C3b and iC3b, linked to an NIR-emitting detector molecule, can be useful to visualize tumor cells and the margins of tumors for in vivo diagnosis and treatment (Luker et al., "Optical Imaging: Current Applications and Future Directions," *J. Nuclear Med.* 49(1):1-4 (2008), which is hereby incorporated by reference in its entirety). Rituximab and epratuzumab, antibody therapies for the treatment of non-Hodgkins lymphoma, act by enhancing immune mechanisms of cytotoxicity toward cancer cells (Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma," *Cancer Immunology, Immunotherapy* 54(12):1172-9 (2005), which is hereby incorporated by reference in its entirety). The aptamers described herein with specificity for C3b/iC3b are potentially useful in association with metal nanoparticles to ablate cancer cells at the margins of tumors that have been opsonized by iC3b.

A further aspect of the present invention is directed to a method of removing an extracellular substance from a sample or body. This method involves providing a sample or body containing an extracellular biomolecule targeted for removal. The sample or body is contacted with an aptamer capable of binding the extracellular biomolecule under conditions effective to bind the extracellular biomolecule to the aptamer. The aptamer-bound biomolecule is removed from the sample or body.

As used herein with respect to any of the therapeutic or preventative methods of treatment, the term patient refers to any mammalian individual, including without limitation, humans and other primates, dogs, cats, horses, cows, sheep, pigs, rats, mice, and other rodents. The individual can be asymptomatic or symptomatic for a particular disease or condition.

All aptamers described herein can be formulated into pharmaceutical compositions comprising one or more aptamers or their derivatives together with a diluent, excipient, or carrier. Here the aptamers or their derivatives are the medically active compound which characterizes the composition, and the diluent, excipient, or carrier being any material suitable for the purpose and being selectable by knowledge of the art or by non-inventive experimentation.

Aptamers of the present invention can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. When administered orally, aptamers of the present invention can experience uptake via the mucosa and epithelia of the digestive tract.

In a preferred embodiment, the aptamers of the present invention can be administered through either intravenous or subcutaneous injection. They can also be dosed topically and via pulmonary administration.

The present invention includes compositions where the aptamers of the present invention are contained in an amount effective to achieve the intended purpose. While individual needs may vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt. Treatment regimen for the administration of the aptamers of the present invention can also be determined readily by those with ordinary skill in the art. That is, the frequency of administration and size of the dose can be established by routine optimization, preferably while minimizing any side effects.

For injectable dosages, solutions or suspensions containing the aptamers can be prepared in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the aptamers may be packaged in a pressurized aerosol container together with suitable propellants, for example, hydrocarbon propellants such as propane, butane, or isobutane with conventional adjuvants. The aptamers of the present invention also may be administered in a non-pressurized form such as in a nebulizer or atomizer.

Another aspect of the present invention is directed to a method of identifying compounds that bind C3 or a biologically active proteolytic product thereof. This method involves exposing C3 or biologically active proteolytic product thereof to the aptamer according to the first aspect of the present invention and a test compound and determining whether the test compound prevents aptamer binding to C3 or biologically active proteolytic product thereof. Prevention of binding identifies the compound as one that binds C3 or a biologically active proteolytic product thereof.

These aspects of the present invention are further illustrated by the examples below.

EXAMPLES

The Examples set forth below are for illustrative purposes only and are not intended to limit, in any way, the scope of the present invention.

Materials and Methods
Proteins and Nucleic Acids

Purified human C3 and iC3b proteins were purchased from Calbiochem (Gibbstown, N.J.). Human C3b protein was from Quidel (San Diego, Calif.). Green Fluorescent Protein (GFP) was purchased from Millipore (Billerica, Mass.). Azami Green, mCherry, d2EGFP and the GFP-mCherry fusion protein were generous gifts from Drs. B. Shui and M. Kotlikoff (Cornell University). All oligonucleotides were provided by Integrated DNA Technologies, Inc. (Coralville, Iowa). RNA aptamers were prepared by in vitro transcription using a MAXIscript T7 Kit or MEGAshortscript T7 kit from Ambion (Austin, Tex.) following the manufacturer's directions. Double-stranded templates resulting from primer extension were amplified by PCR. Sequences of aptamers are given in Example 1.

Triple Complex Formation

To detect triple complex formation, 10 μg of C3 protein diluted in 50 μl of binding buffer (containing 50 μg/ml of PMSF and 1 μg/ml of aprotinin) was immobilized on a 1 cm² nitrocellulose filter, presoaked with binding buffer. The filter was blocked with 10 mg/ml BSA for at least 1 hour to overnight, and washed with binding buffer (20 mM Tris-HCl pH 7.6, 150 mM NaCl, 10 mM $MgCl_2$). About 10 μg of bifunctional aptamer, which was ~4-fold the molar quantity of C3 used, was reconstituted in 100 μl of binding buffer with 40 U of SUPERase.In (Ambion) and incubated on the filter for at least 1 hour at 37° C. A comparable amount of yeast total RNA (~300 nt in length) was used in the controls. The filter was washed and incubated with 5 μg of GFP in 100 μl of binding buffer in the presence of SUPERase.In and protease inhibitors (PMSF and aprotinin), and washed again with binding buffer. GFP and other proteins were eluted with 150 μl of elution buffer (20 mM Tris-HCl pH 7.6, 750 mM NaCl), precipitated with trichloroacetic acid, and run on 6-12% SDS polyacrylamide gradient gels. Western blotting was performed with rabbit anti-GFP antibody (Sigma, St. Louis, Mo.). The signals were detected using the ECL kit (GE Healthcare).

Cell Culture and Cell-Based Assays

THP-1 human monocytic cells (obtained from ATCC, Manassas, Va.) were maintained in RPMI-1640 medium (ATCC) supplemented with 10% fetal bovine serum (FBS), 100 U/ml of penicillin, 100 μg/ml of streptomycin, and 0.05 mM 2-mercaptoethanol. For immunohistochemistry, cells were induced to differentiate to an adherent macrophage-like state by treatment with 50 ng/ml phorbol 12-myristate 13-acetate (PMA) (Kohro et al., "A Comparison of Differences in the Gene Expression Profiles of Phorbol 12-myristate 13-acetate Differentiated THP-1 Cells and Human Monocyte-derived Macrophage," *J. Atherosclerosis Thrombosis* 11:88-97 (2004); Whatling et al., "Effect of macrophage differentiation and exposure to mildly oxidized LDL on the proteolytic repertoire of THP-1 monocytes," *J. Lipid Res.* 45:1768-1776 (2004), each of which is hereby incorporated by reference in its entirety). Each experiment was repeated at least three times.

For the GFP internalization assays, 1 μg (~$10^{13}$ molecules) of Apt[C3-GFP] was reconstituted in 20 μl of binding buffer (see above), heated at 70° C. for 5 minutes, and renatured at 37° C. with 40 U of SUPERase.In. The aptamer was mixed with ~6×$10^{13}$ molecules (20 μg) of purified iC3b, followed by $10^{14}$ molecules (10 μg) of GFP or its derivatives in 200 μl of serum-free RPMI-1640 medium supplemented with 0.1 mg/ml of BSA and 2.5 mM $MgCl_2$, and incubated for 30 minutes. An additional 300 μl of RPMI-1640 medium was added for a total volume of 0.5 ml. Approximately 2×$10^6$ THP-1 cells were mixed with the prepared complex, and the cells and the protein-aptamer complexes were incubated for various times (15 to 30 minutes). Subsequently, the cells were washed with 15 ml of RPMI-1640 medium (ice-cold or warm, depending on the experiment) three times and kept on ice for microscopic observation. Live or fixed (with 4% paraformaldehyde) cells were observed and photographed using differential interference contrast (DIC) and GFP filters with a 40× objective on a Zeiss® Axiovert™ microscope.

Anti-iC3b antibody (Quidel) was used to visualize iC3b molecules associated with THP-1 cells. The cells were prepared on a coverslip (18×18 mm) in RPMI-1640 medium with 50 ng/ml PMA and allowed to grow for 2-3 days to a density of ~0.5 to 1×$10^5$ cells/cm². Before the assay, the cells were washed with pre-warmed serum-free RPMI-1640 medium five times. Then 150 μl of protein-aptamer mixture was added to the cells, and the cells were incubated for 30 minutes in a humid chamber at 37° C., followed by repeated washing in 1×PBS and fixation with 4% paraformaldehyde. Fixed cells were washed and permeabilized with 150 μl of 0.2% Triton X-100 in 1×PBS solution for 5 minutes followed by washing. Cells were incubated with anti-iC3b antibody for 1 hour, then with Alexa Fluor 594 secondary antibody (Molecular Probes, Eugene, Oreg.) for an additional hour. Cells were photographed using DIC, GFP, rhodamine and DAPI filters.

Lysotracker red DND99 (Invitrogen, Carlsbad, Calif.), a vital stain composed of a weak base linked to a fluorophore, was used to visualize lysosomal compartments of live cells. In our assays 25 nM LysoTracker (final concentration) was added to the cell suspension during endocytosis. Cells were washed as described above and fixed with 4% paraformaldehyde, and the images were photographed using green (GFP) and red (rhodamine) filters and merged.

To follow the degradation of the target proteins, after 15-minute incubation with the protein-aptamer complex, the cells were divided into two fractions to examine degradation at different stages. The first fraction was washed and immediately fixed with 4% paraformaldehyde. The remaining cells were incubated for an additional 15 minutes, then washed and incubated at 37° C. for several hours to several days in RPMI-1640 medium with FBS. For bi-color detection of the GFP-mCherry fusion protein, GFP and rhodamine filters were used (Anderson et al., "A New Configuration of the Zeiss LSM 510 for Simultaneous Optical Separation of Green and Red Fluorescent Protein Pairs," *Cytometry A* 69:920-929 (2006); Song et al., "*Arabidopsis* Primary MicroRNA Processing Proteins HYL1 and DCL1 Define a Nuclear Body Distinct from the Cajal Body," *Proc. Nat'l Acad. Sci. U.S.A.* 104:5437-5442 (2007), each of which is hereby incorporated by reference in its entirety).

Example 1

SELEX for C3

Iterative rounds of aptamer selection and amplification were performed using purified C3 protein as the target according to protocols described previously.

The aptamer candidate library was generated as single-stranded DNA on an automated solid-phase synthesizer by Integrated DNA Technologies, Inc. at 1 μmmole scale. This template strand, named Temp50, has the nucleotide sequence:

(SEQ ID NO: 1)
5'-ACCGAGTCCAGAAGCTTGTAGTACT(N)$_{50}$GCCTAGATGGCAGTT
GAATTCTCCCTATAGTGA-3', where "(N)$_{50}$"=A, G, T, C (1:1:1:1 expected, for 50 positions).

Double-stranded templates were generated by annealing to the Temp50 primer, named ForT7, followed by a bi-directional primer extension using the Taq DNA polymerase. The primer ForT7 contains the sequence of a T7 promoter for in vitro transcription, and has the nucleotide sequence:

(SEQ ID NO: 2)
5'-GTAATACGACTCACTATAGGGAGAATTCAACTGCCATCTA-3'.

The double stranded templates resulting from the bi-directional primer extension can be subsequently amplified by PCR using the primer ForT7 and another primer named RevUniv, which has the nucleotide sequence:

(SEQ ID NO: 3)
5'-ACCGAGTCCAGAAGCTTGTAGT-3'.

A fraction of this pool containing $10^{15}$ unique individuals was used as template in an in vitro transcription reaction to generate the RNA pool using the MEGAscript kit from Ambion (Austin, Tex.) according to the manufacturer's protocol.

The first in vitro selection experiment used C3 as the target. Six rounds of selection were done on nitrocellulose filter and the last round was done in the acrylamide gel. For the first round of selection, a degenerate pool of 100 μg of RNA was used in 1 ml of buffer containing 20 mM Tris HCl pH 7.6, 150 mM NaCl, 10 mM MgCl$_2$. RNA was denatured at 65° C. for 10 minutes and then incubated at 37° C. for 10 minutes. Into the RNA solution, 2 μl of RNase inhibitor (Superrase inhibitor, #AM2682 from Ambion) was added, and 150 pM human C3 protein (Calbiochem) was added and incubated for 2 hours at 37° C. The reaction mixture was separated on 0.25 micron nitrocellulose filter paper (Millipore) using a manifold (Sigma). The filter was washed with 5.5 ml of buffer (20 mM Tris HCl pH 7.6, 150 mM NaCl, 10 mM MgCl$_2$) under vacuum. Filter paper containing RNA-protein complexes was extracted with 8 M urea in 1×TBE buffer, incubated at 95° C. for 2 minutes, and extracted with phenol-chloroform (1:1). The mixture was centrifuged in a tabletop microfuge, the supernatant was extracted and precipitated with 1 μg of linear acrylamide, 0.3 mM sodium acetate (pH 5.2), and two volumes of ethanol. RNA was recovered by centrifugation at 12,000 rpm in a tabletop centrifuge, washed with 70% ethanol, dried, and used for cDNA synthesis. In the dried RNA, 7.5 μl of water, 2.5 μl of 20 μM oligo 5'-CCGAGTCCA-GAAGCTTGTAGT-3' (SEQ ID NO: 4), and 3 μl of 2.5 mM of all four dNTP mix was added and incubated at 70° C. for 10 minutes, followed by an incubation at 42° C. for 5 minutes. Then, 4 μl of 5×1$^{st}$ strand synthesis buffer, 1 μl of 0.1M DTT, 1 μl of RNase inhibitor, and 200 U of reverse transcriptase (Promega) was added and incubated at 37° C. for 20 min, followed by an incubation at 48° C. for 20 minutes. The resulting cDNA was used for an optimum round of PCR cycles using Taq DNA polymerase (New England Biolabs) and the primers as described before. A typical PCR reaction of 100 μl contains 1.5 M betain, 10 mM Tris pH 8.3, 50 mM KCl, 1.5 mM MgCl$_2$, 30 nM template, 500 nM primers, 200 μM dNTP, and 5 U Taq polymerase. Standard PCR cycles were used with an initial denaturation at 95° C. for 5 minutes, followed by a repeated cycle of denaturation at 95° C. for 1 minute, annealing at 60° C. for 2 minutes, and extension at 72° C. for 5 minutes. Product DNA was analyzed using an 8% polyacrylamide gel (acrylamide:bis-acrylamide=29:1). DNA obtained from the PCR was precipitated and dissolved in water. This PCR product was used for an in vitro transcription reaction to make RNA. RNA was made from the PCR product template using the Megashortscript™ kit (Ambion Inc., Austin, Tex.) following the manufacturer's recommendations. The resulting RNA was used for the next round of selection.

Several parameters were changed in the following round of selection, as described in Table 1 below.

TABLE 1

Parameters for Final Round of SELEX

| Generation | RNA: Protein | Incubation Time (min) | Reaction Vol. (ml) | Negative Selection | Filter Wash Vol. (ml) | PCR Cycles |
|---|---|---|---|---|---|---|
| 1 | 20:1 | 120 | 1.0 | no | 5.5 | 16 |
| 2 | 20:1 | 60 | 0.5 | no | 10 | 7 |
| 3 | 20:1 | 60 | 0.5 | yes | 15 | 16 |
| 4 | 20:1 | 30 | 0.5 | yes | 15 | 11 |
| 5 | 50:1 | 10 | 0.5 | yes | 15 | 10 |

TABLE 1-continued

Parameters for Final Round of SELEX

| Generation | RNA: Protein | Incubation Time (min) | Reaction Vol. (ml) | Negative Selection | Filter Wash Vol. (ml) | PCR Cycles |
|---|---|---|---|---|---|---|
| 6 | 50:1 | 10 | 0.5 | yes | 20 | 5 |
| 7* | 10:1 | 10 | 0.1 | yes | 0 | 6 |

*In this generation, RNA protein complex was separated in a polyacrylamide gel following the EMSA protocol.

Radiolabeled RNA was prepared using the DNA mentioned above and analyzed in a gel mobility shift assay to determine the binding ability of RNA aptamers (described below). An enriched pool of DNA was cloned in a plasmid vector and sequenced.

Cloning was performed using the pGEM-3Z plasmid vector (Promega). Vector and insert DNA were digested with restriction endonucleases EcoRI and HindIII (New England Bio Labs). Three μg of vector DNA and 1 μg of insert DNA were mixed with 20 U each of EcoRI and HindIII in a 40-μl volume. The mixture was incubated at 37° C. for 2 hours and extracted with phenol-chloroform (1:1) followed by chloroform. After extraction, DNA was precipitated with ethanol. DNA was dissolved and ligated with T4-DNA ligase (New England Bio Labs) in a 20-μl volume with a vector:insert ratio of 1:2. Ligated DNA was transformed into JM109 competent cells (Promega). Putative positive clones were selected from LB-agar plates containing IPTG, X-gal (New England Bio Labs), and ampicillin (Sigma). White colonies were selected for further use. Colonies were grown in 5 ml LB liquid medium with ampicillin. Plasmid DNA was prepared using a Qiagen kit (Qiagen) following manufacturer's guidance. Plasmid DNA was digested with endonucleases KpnI and PstI, followed by separation of the digested DNA on an 8% polyacrylamide gel to check for the presence of insert DNA.

Fifty-four individuals were sequenced from this final pool. Sequencing was done using the automated sequencing facilities available in the Life Sciences Building, State University of New York at Albany (SUNY). The most abundant sequence occurred 9 times in this sample, and the second most abundant sequence occurred 7 times. Both showed specific binding to C3 and were named AptC3-1 and 2, respectively. These aptamers have nucleotide sequences as shown below.

```
AptC3-1:
                                      (SEQ ID NO: 5)
5'GGGAGAAUUCAACUGCCAUCUAGGCUAGAAGAAUAUGACGGAUUGACC

GUAUCAGGGUAGCCGAAGGGAGACAGAAGUACUACAAGCUUCUGGACUCG

GU3'.

AptC3-2:
                                      (SEQ ID NO: 6)
5'GGGAGAAUUCAACUGCCAUCUAGGCAAAUCCGCGAGCGCCGGUACCGG

UGGCGCAUGCCCACACAGCACUAAACGAGUACUACAAGCUUCUGGACUCG

GU3'.
```

Figure 7A:
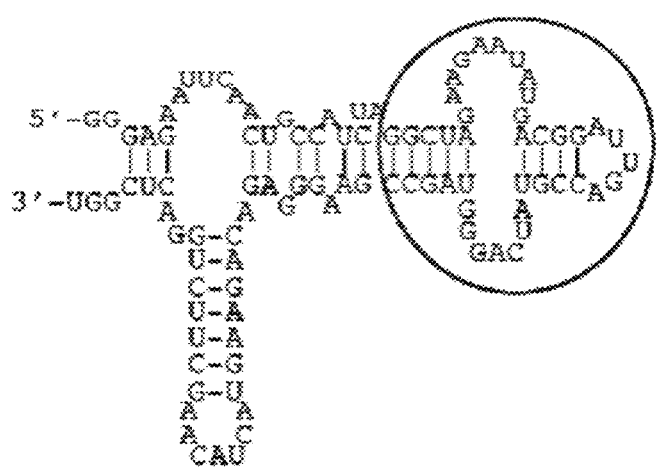
FIG. 7A illustrates the predicted secondary structure of aptamer AptC3-1 (SEQ ID NO: 5). The minimized functional aptamer portion is circled.

The predicted secondary structure of AptC3-1 is illustrated in FIG. 7A, with its minimized version encircled. This structure was predicted using the mfold program (Zuker, "Mfold Web Server for Nucleic Acid Folding and Hybridization Prediction," *Nucl. Acids Res.* 31:3406-3415 (2003), which is hereby incorporated by reference in its entirety) and confirmed by mutational analyses.

Example 2

Aptamer Binding Assays

The affinity of aptamers and their derivatives to C3, C3b, or iC3b were investigated using two independent binding assays.

RNA probes were uniformly labeled with [α-$^{32}$P]-CTP (GE Healthcare, Piscataway, N.J.) using the T7-MAXIscript™ in vitro transcription kit (Ambion, Austin, Tex.) according to the manufacturer's instructions. Prior to their use in the binding assay, the majority of transcripts of each RNA preparation were subjected to electrophoresis in an 8% polyacrylamide, 7M-urea gel and shown to be of the expected size. All binding assays were performed in 20-μl volumes in 1× binding buffer. The binding buffer contains 20 mM Tris-HCl pH 7.6, 150 mM NaCl, and 10 mM $MgCl_2$. A typical binding assay using labeled RNA contains approximately 20 fmole of $^{32}$P-labeled RNA probe and different amounts (usually 1 to 10 pmol) of protein.

Initially, RNA was heated to 65° C. for 10 minutes then switched to 37° C. for an additional 10 minutes before the addition of protein. The reactions were allowed to equilibrate for 15-20 minutes at ambient temperature before being subjected to Electrophoretic Mobility Shift Assay ("EMSA") or filter binding.

RNA-protein complexes were separated on a 5% polyacrylamide gel (acrylamide:bis-acrylamide=70:1) made with Tris-glycine buffer (12.5 mM Tris, 100 mM glycine, pH 8.0), containing 2.5 mM $MgCl_2$ and 10% glycerol. The gel was first subjected to 200 volts for 30 minutes in a cold room. The mixture was incubated in 5 μl of 50% glycerol then loaded onto the gel and further electrophoresed for 2 hours at 4° C. before drying and imaging. The image was scanned using a Typhoon™ phosphoimager with ImageQuant software (GE Healthcare) and the data was analyzed.

For filter binding, the above-mentioned reaction mixture was immobilized on nitrocellulose (Millipore) using a manifold (Millipore) or a Bio-Dot SF (slot format) Microfiltration System (Bio-Rad, Hercules, Calif.). The nitrocellulose membrane was first soaked in binding buffer containing 20 mM Tris-Cl (pH 7.6), 150 mM NaCl, 10 mM $MgCl_2$. Nitrocellulose and two pieces of 3M Whatmann filter paper (3M) were assembled in the manifold as per company recommendations. Each well was washed with 1 ml of binding buffer. Samples were loaded in the wells and vacuum was applied to bind the complex, then each well was washed with 2 ml of binding buffer. The nitrocellulose membrane was then air dried and exposed to a phosphor screen (GE Healthcare) for 1 hour. The image was scanned using a Typhoon imager and ImageQuant software and the data was analyzed.

Example 3

Minimization of C3 Aptamers

Because the "true aptamer" moiety may be only a fraction of a full-length isolate, the strategy of using the minimal active version of the aptamer when creating new constructs was adopted. Following nucleotide deletions of AptC3-1, the resulting sequence was tested for binding efficiency. For example, a deletion construct was made using the following primer pair to amplify the DNA template:

(SEQ ID NO: 7)
5'GTAATACGACTCACTATAGGGCTAGAAGAATATGACG3' and (SEQ ID NO: 8)
5'CGGCTACCCTGATACGGTC3'

The RNA sequence, designated MiniAptC3-1, is as follows:

(SEQ ID NO: 9)
5'GGGCUAGAAGAAUAUGACGGAUUGACCGUAUCAGGGUAGCCG3'.

Nucleotides 2-41 appear in FIG. 7A (encircled portion of secondary structure). This 42-nucleotide long radiolabeled RNA was used for EMSA and filter binding assay.

For AptC3-2, the following two primers were used to make the necessary deletion.

(SEQ ID NO: 10)
5'GTAATACGACTCACTATAGGGAGAATTCAACTGCCATCTA3' and (SEQ ID NO: 11)
5'GGGCATGCGCCACCGGT3'.

After transcription, the sequence of the RNA is:

(SEQ ID NO: 12)
5'GGGAGAAUUCAACUGCCAUCUAGGCAAAUCCGCGAGCGCCGGUACCGG UGGCGCAUGCCC3'.

Example 4

Affinity and Specificity of Aptamers to C3, C3b, or iC3b

C3 protein was used to evaluate the binding ability of different generations of aptamer (during SELEX). A discrete retarded band was evident by generation 4 and 5 and an increase in the amount of that band in generation 7.

Figure 4:
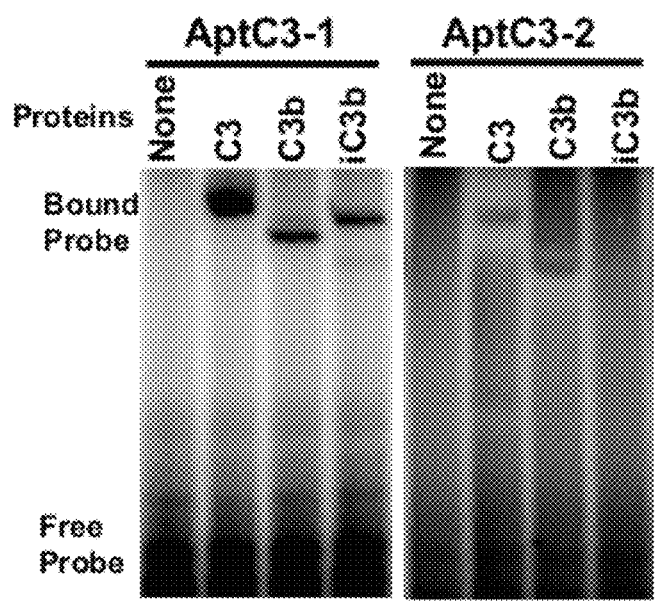
FIG. 4 is an Electrophoretic Mobility Shift Assay ("EMSA") image showing the aptamer complexes with C3 and its derivatives.

Using the minimized AptC3-1 aptamer, a retarded band was evident with all three forms of complement protein (C3, C3b, and iC3b) (FIG. 4, left panel). In the case of the AptC3-2 aptamer, retarded bands were visible only with C3 and C3b proteins (FIG. 4, right panel).

Figure 5:
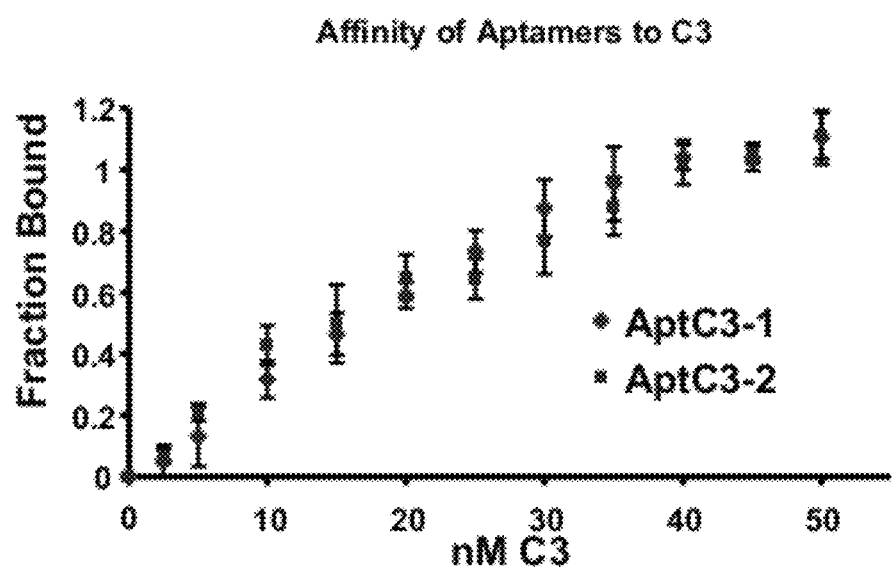
FIG. 5 is a graph showing the affinity of aptamers for C3 and its derivatives as measured by filter binding assay.
Figure 6:
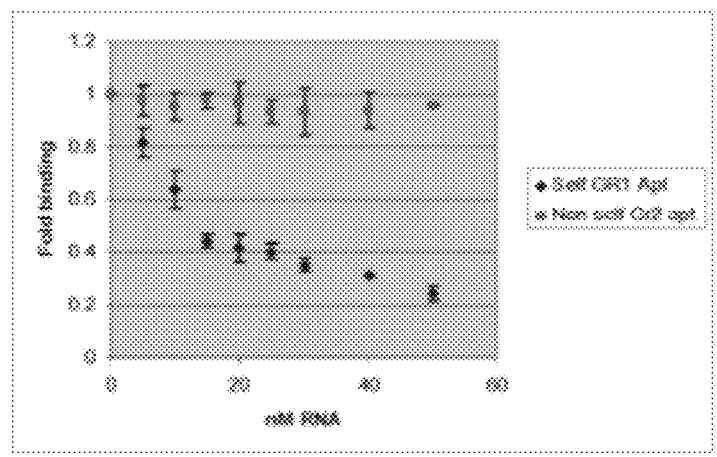
FIG. 6 is a graph showing the results of a competition assay that shows AptC3-2 does not compete with AptC3-1 for binding to C3.

The C3 aptamers were also characterized with filter binding assays. Filter binding assay shows that the $K_d$ of C3, C3b, and iC3b protein is around 20 nM for AptC3-1 (FIG. 5), whereas for AptC3-2 the $K_d$ for C3 and C3b was 30 nM (FIG. 5). Filter binding assay also demonstrates that AptC3-2 does not bind iC3b, confirming the result of the EMSA. Additionally, a competition assay further confirms that these two aptamers do not compete for the same position in C3 protein (FIG. 6).

Example 5

Screening and Titrating Inhibitory Activity of Aptamers

Inactivation of C3 results in the inhibition of C3a and C5a production and of C5b-C9 formation. The inhibitory effect of aptamers to C3 can be evaluated by detection of complement-induced hemolysis, which indicates the function of the complement pathways. In a hemolytic assay, serial dilutions of the sample to be analyzed are incubated with antibody-sensitized erythrocytes at a defined temperature. The number of red blood cells lysed is determined by spectrophotometric absorbance of released hemoglobin. This readout has a linear relationship to complement protein levels around 50% lysis range, and the activity of complement system is expressed as the concentration or dilution of the sample required to produce 50% lysis. The AptC3-1 and AptC3-2 aptamers were tested and found not to have inhibitory activity.

Example 6

Construction of Bi-functional Aptamers

A bi-functional aptamer comprises one or more targeting aptamers and one or more utility aptamers. The simplest version of a bi-functional aptamer is composed of one targeting aptamer and one utility aptamer. The method disclosed in U.S. patent application Ser. No. 11/103,122 (U.S. Patent Application Publication No. 2005/0282190A1), which is hereby incorporated by reference in its entirety, allows more than two aptamers to be operably connected in a single molecular entity with the help of structural modules. In this example, a few instances of the simplest version of bi-functional aptamers created by directly connecting two minimized aptamers are described.

An RNA aptamer for the green fluorescent protein (GFP) has been previously described (PCT Patent Application Publ. No. WO 2007/147149, which is hereby incorporated by reference in its entirety). This GFP aptamer, named AptGFP-AP3, has the nucleotide sequence of SEQ ID NO:13 as follows:

5'GCGUGAGACGUCUUGAUGAAAUCCGGCUCGGCAAUGGUUCGUGGCGAA UUGGGUGGGAAAGUCCUUAAAAGAGGGCCACCACAGAAGCUUGUGGAGU UAACAGCAA3'.

This aptamer binds GFP with a $K_d$ of 14.4 nM and also binds with roughly equivalent affinity to eGFP, eCFP, and eYFP. While the binding of the aptamer inhibits GFP fluorescence (510 nm emission), its binding enhances the eCFP and eYFP fluorescence. To develop an aptamer-mediated endocytosis assay (vide infra) bi-functional aptamers containing AptGFP-AP3 and AptC3-1 were designed and constructed.

Figure 7B:
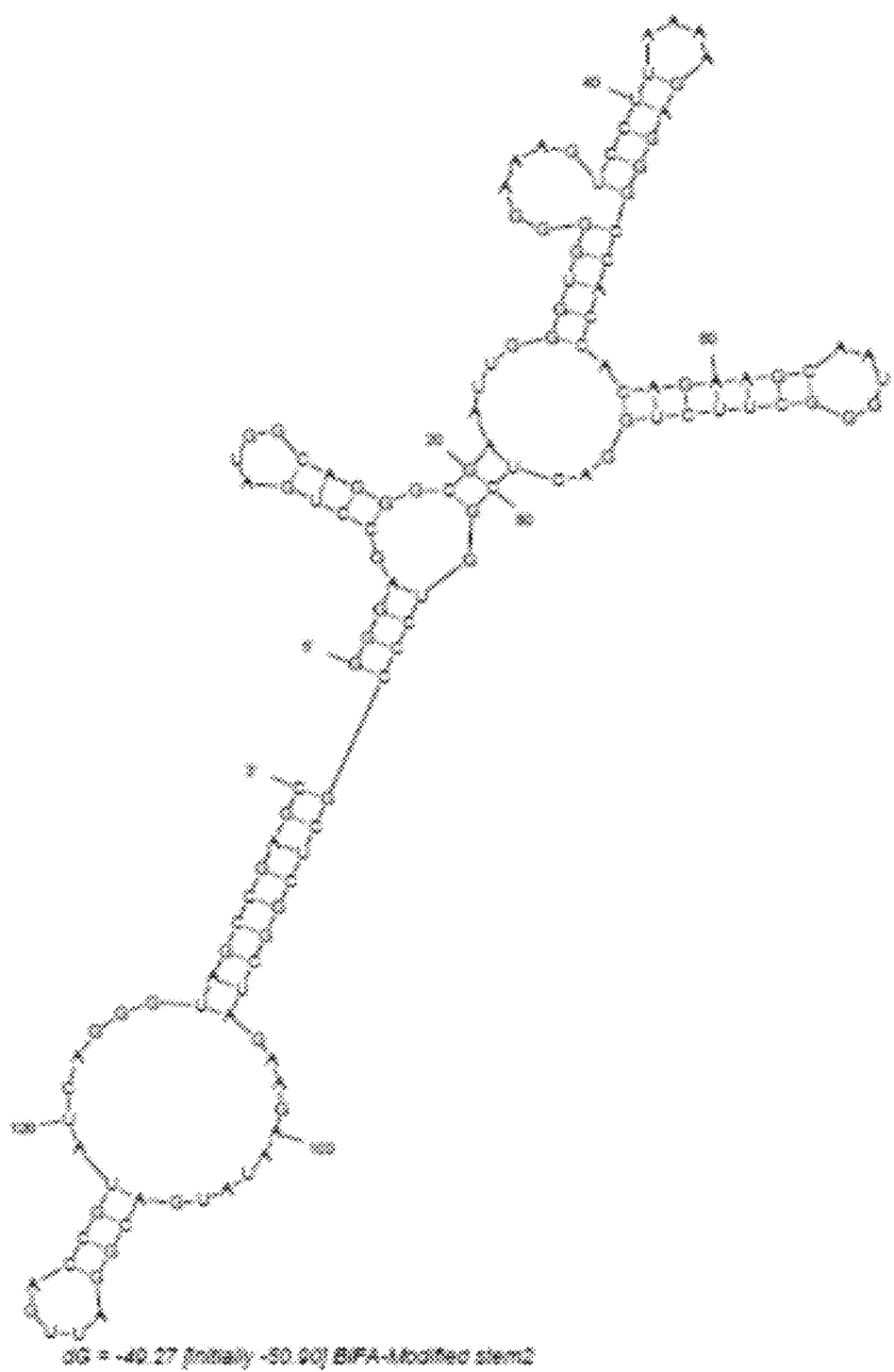
FIGS. 7B-D depict the predicted secondary structures of three bi-functional aptamers (SEQ ID NOS: 14, 17, and 19, respectively). SEQ ID NO: 14 is designated herein as Apt[C3-GFP].
Figure 7C:
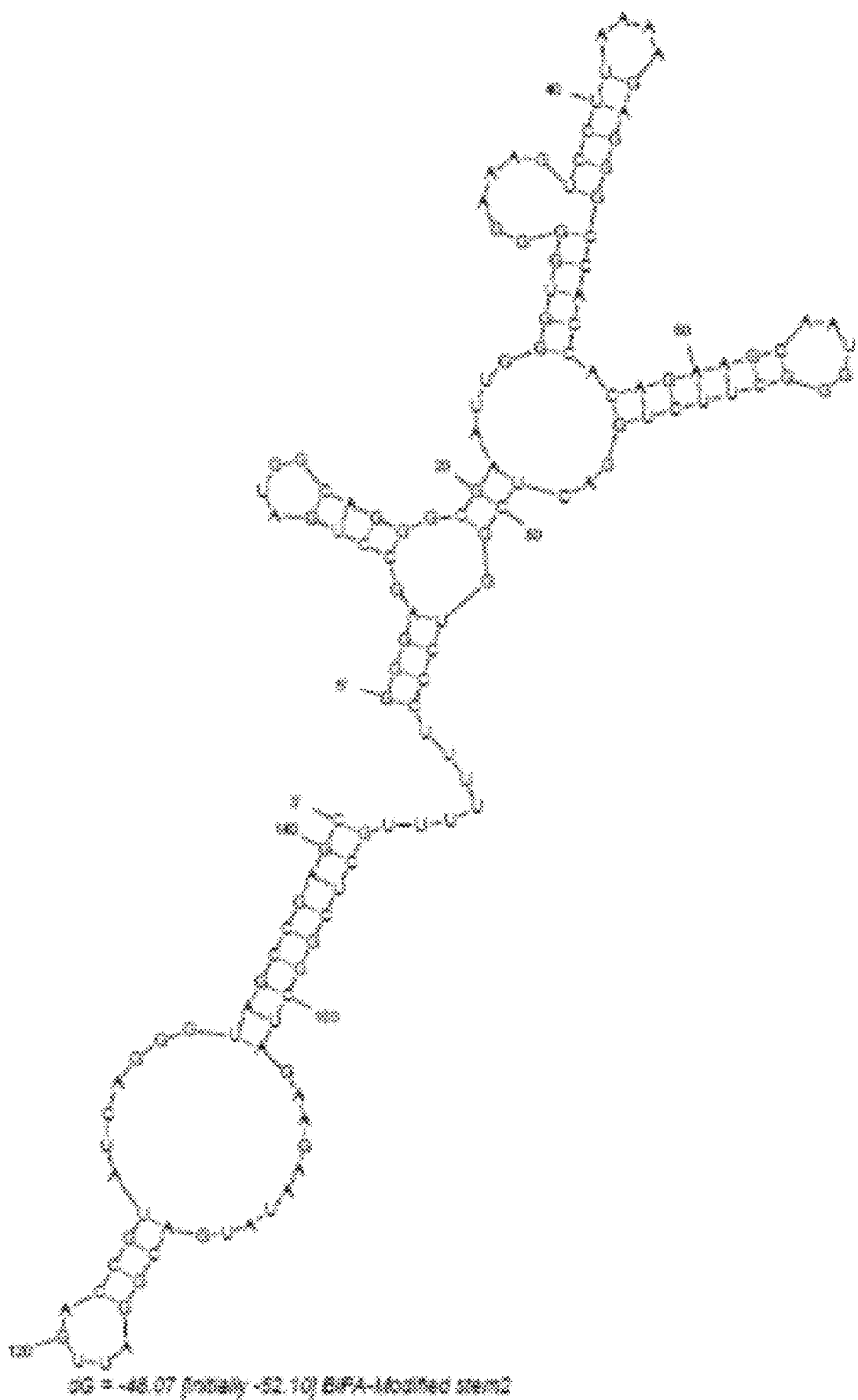
Figure 7D:
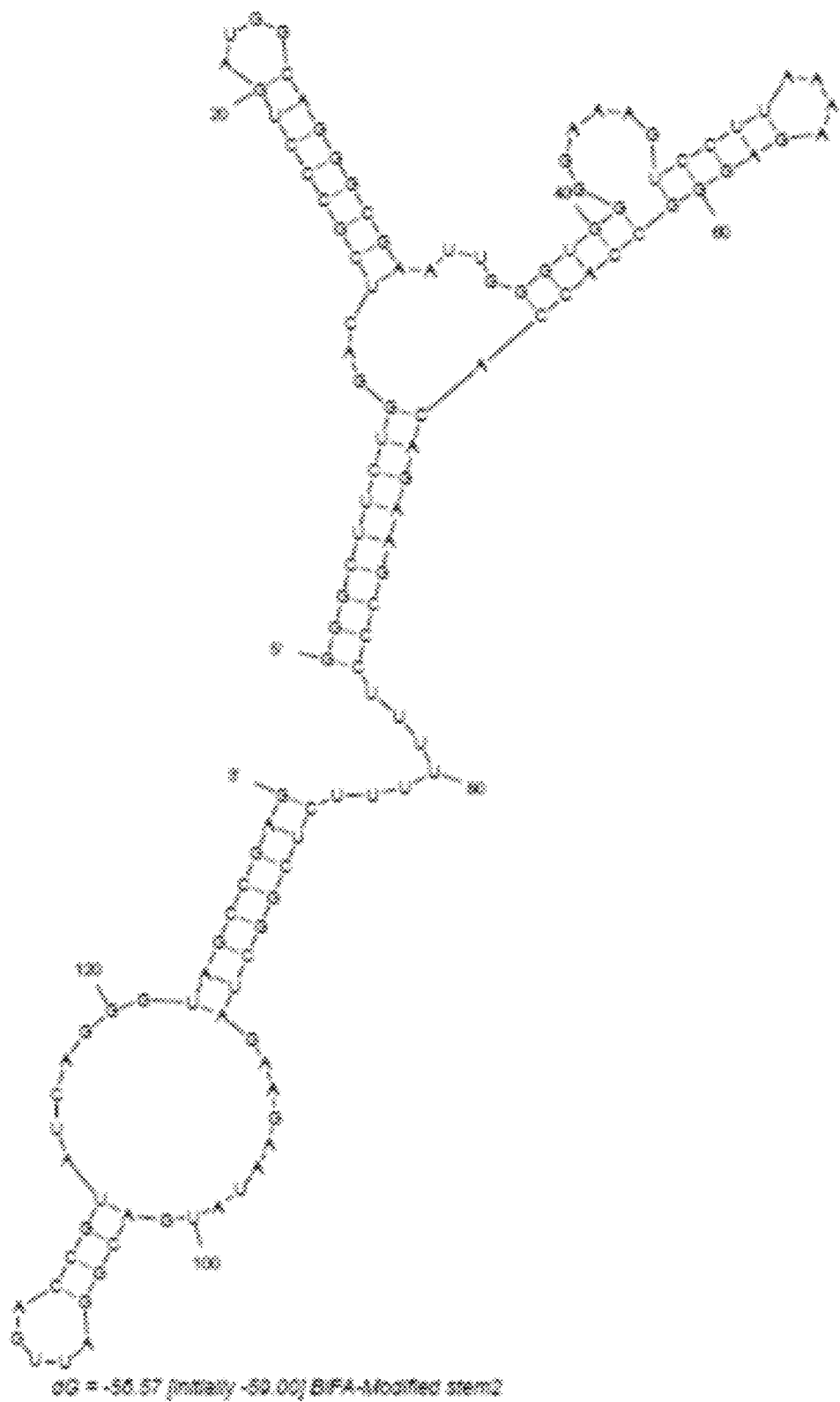

As disclosed previously, the secondary structure of AptGFP-AP3 has been confirmed, and it has three stems forming a three-way junction. One of these stems has an apical loop and a side loop that are critical to the activity of the aptamer; the other two stems can be used to connect with other aptamers. As described supra, AptC3-1 has been minimized to a hairpin with an apical loop and an internal loop. With these minimized structures, bi-functional aptamers can be created by simply engrafting AptC3-1 together with AptGFP-AP3. Three such constructs are depicted in FIGS. 7B-D. Type A and Type B are put together in different configurations by engrafting AptC3-1 to different stems of AptGFP-AP3. Type A2 and Type B1 are more flexible with a single strand poly-U linker to break the possible rigid stacking of the two stems in type A1. These constructs are described as follows. Type A1 aptamer, also designated Apt[C3-GFP], includes AptC3-1 connected to stem 3 of AptGFP and has the following RNA sequence:

```
                                                    (SEQ ID NO: 14)
5'GGGAGCCUGAUGGCAGGGCGAAUUGGGUGGGAAAGUCCUUAAAAGAG

GGCCACCACAGAAGCAAUGGGCUUCUGGACUCGGUCCCGCUCGGCUAGAA

GAAUAUGACGGAUUGACCGUAUCAGGGUAGCCGAGC3'.
```

To generate the above sequence, the following two PCR primers were used:

```
                                                    (SEQ ID NO: 15)
5'GTAATACGACTCACTATAGGGAGCCTGATGGCAGGGCGAATTGGGTGG

GGAAAGTCCTTAAAAGAGGGCCACCACAGAAGCAATGGGCTTCTGGACT

3'
and
                                                    (SEQ ID NO: 16)
5'GCTCGGCTACCCTGATACGGTCAATCCGTCATATTCTTCTAGCCGAGC

GGGACCGAGTCCAGAAGCCCATTGCTTC3'.
```

Type A2 aptamer (AptC3-1 connected to stem 3 of AptGFP via a spacer) has the following RNA sequence:

```
                                                    (SEQ ID NO: 17)
5'GGGAGCCUGAUGGCAGGGCGAAUUGGGUGGGAAAGUCCUUAAAAGAG

GGCCACCACAGAAGCAAUGGGCUUCUGGACUCGGUCCCUUUUUUGCUCG

GCUAGAAGAAUAUGACGGAUUGACCGUAUCAGGGUAGCCGAGC3'.
```

To generate the above sequence, the following two PCR primers were used:

```
                                                    (SEQ ID NO: 15)
5'GTAATACGACTCACTATAGGGAGCCTGATGGCAGGGCGAATTGGGTG

GGGAAAGTCCTTAAAAGAGGGCCACCACAGAAGCAATGGGCTTCTGGAC

T3'
and
                                                    (SEQ ID NO: 18)
5'GCTCGGCTACCCTGATACGGTCAATCCGTCATATTCTTCTAGCCGAGC

AAAAAAAGGGACCGAGTCCAGAAGCCCATTGCTTC3'.
```

Type B aptamer (AptC3-1 connected to stem 2 of AptGFP) has the following RNA sequence:

```
                                                    (SEQ ID NO: 19)
5'GGGCUUCUGGACUCGCCCUGAUGGCAGGGCGAAUUGGGUGGGGAAAGU

CCUUAAAAGAGGGCCACCACAGAAGCCCUUUUUUCUCGGCUAGAAGAAU

AUGACGGAUUGACCGUAUCAGGGUAGCCGAG3'.
```

To generate the above sequence, the following two PCR primers were used:

```
                                                    (SEQ ID NO: 20)
5'GTAATACGACTCACTATAGGGCTTCTGGACTCGCCCTGATGGCAGGGC

GAATTGGGTGGGGAAAGTCCTTAAAAGAGGGCCACCACAGAA3' and
                                                    (SEQ ID NO: 21)
5'CTCGGCTACCCTGATACGGTCAATCCGTCATATTCTTCTAGCCGAGAA

AAAAGGGCTTCTGTGGTGGCCCTCTTTT3'.
```

The secondary structures of the designed constructs were predicted by free energy minimization algorithms to ensure the correctly folded form of each component in the composite structure (FIGS. 7B-D).

Figure 8A:
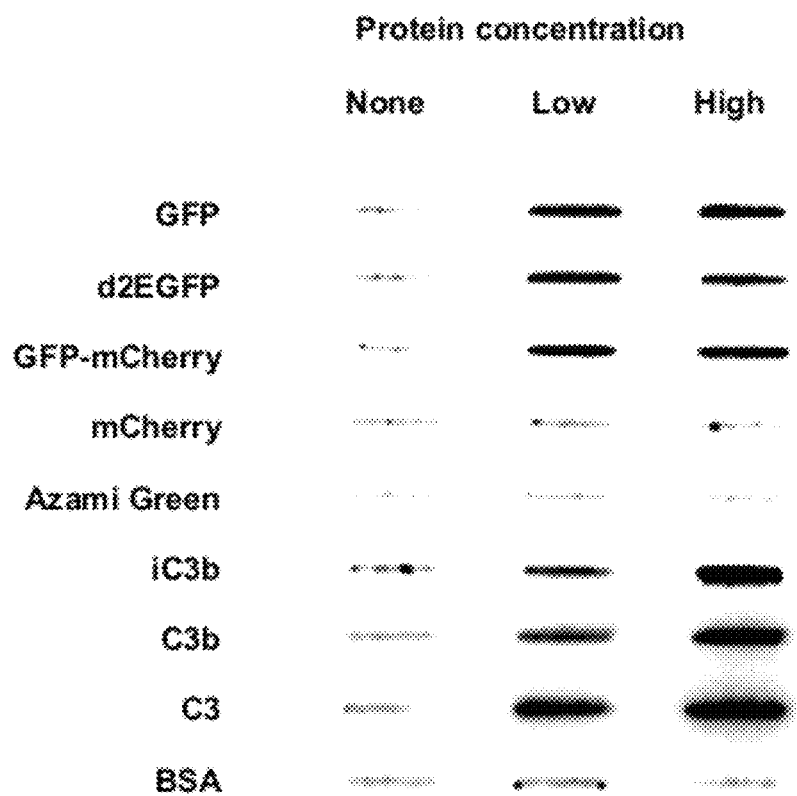
FIGS. 8A-C illustrate the activity of a bi-functional aptamer and formation of the triple complex.

Using the bi-functional aptamer of SEQ ID NO: 14 (FIG. 7C), it was next demonstrated that both component aptamers remain functional in the composite. As shown in FIG. 8A, this RNA molecule possesses the ability to bind GFP and C3b or iC3b. In addition, AptGFP-AP3 interacted with the GFP derivative d2EGFP, but did not interact with Azami Green or mCherry, fluorescent proteins unrelated to GFP (see FIG. 8A).

Figure 8B:
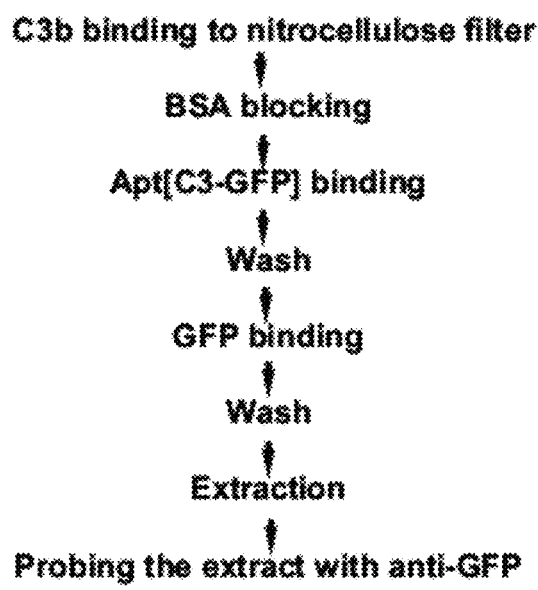
Figure 8C:
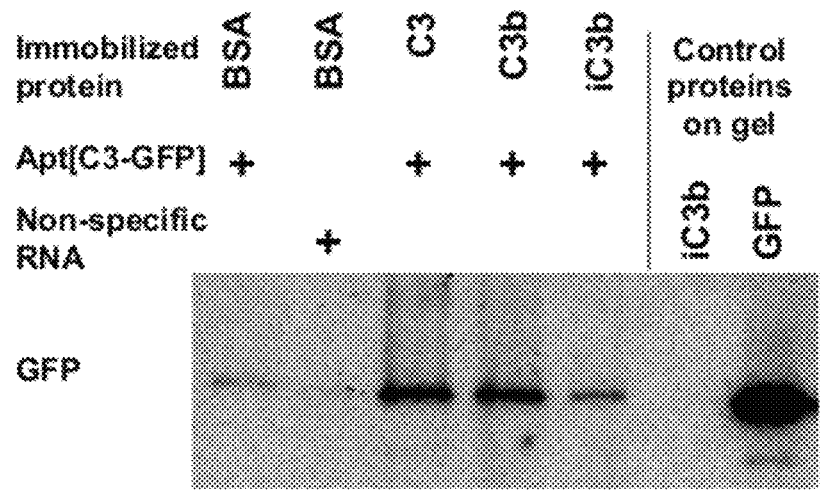

For the bi-functional aptamer to function as a molecular adaptor, it must bind both ligands independently and simultaneously. In the assay outlined in FIG. 8B, the capability of C3b/iC3b, Apt[C3-GFP], and GFP to form a stable triple complex was examined using the procedures described above. As shown in FIG. 8C, GFP was detected only when the bi-functional aptamer was present, indicating that the adaptor molecule was indeed able to function as a molecular adaptor to induce proximity of the two proteins.

Example 7

Figure 9:
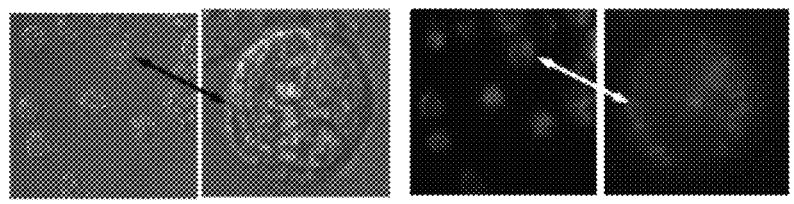
FIG. 9 illustrates aptamer-dependent GFP association with unfixed THP-1 cells. Representative micrographs of cells at two different magnifications, using differential interference contrast (DIC) or a green fluorescent filter. In the experimental panel, cells were incubated with Apt[C3-GFP], GFP and iC3b. iC3b was omitted in the control. Cells were washed with ice-cold serum-free RPMI medium and kept on ice before photography.
Figure 9:
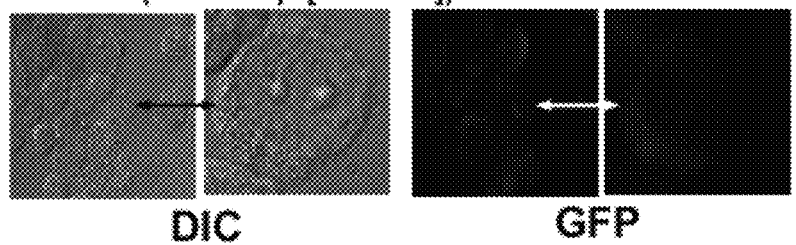

Specific Association of GFP with Macrophages Mediated by the Bi-Functional Aptamer and iC3b A cell-based functional assay was developed to examine whether the bi-functional aptamer was able to cause association of GFP with macrophages in the presence of iC3b. Analogous to the clearance of immune complexes, this experimental system contained four purified components: phagocytic cells, C3b or iC3b molecules, Apt[C3-GFP], and GFP or its derivatives. To represent phagocytes, the human acute monocytic leukemia cell line THP-1 was chosen (Tsuchiya et al., "Establishment and Characterization of a Human Acute Monocytic Leukemia Cell Line (THP-1),"*Internat'l J. Cancer* 26:171-176 (1980), which is hereby incorporated by reference in its entirety). This cell line expresses Fc and C3b receptors, but lacks surface and cytoplasmic immunoglobulins. It is capable of phagocytosis of latex particles and sensitized sheep erythrocytes. Treatment with phorbol esters can induce THP-1 cells to differentiate into macrophage-like cells that adhere to tissue-culture surfaces (Tsuchiya et al., "Induction of Maturation in Cultured Human Monocytic Leukemia Cells by a Phorbol DIESTER," *Cancer Res.* 42:1530-1536 (1982), which is hereby incorporated by reference in its entirety). Before using the THP-1 cell line in assays, the expression of CR3, a predominant iC3b receptor, was confirmed by immunostaining As phagocytes may have a natural tendency to engulf substances added to the media, two types of controls were designed to demonstrate the specificity of bi-functional aptamer mediated phagocytosis. In the first type of control, one molecular component (C3b/iC3b, Apt[C3-GFP], or GFP) was omitted. In the second type, GFP was substituted by another fluorescent protein not recognized by AptGFP-AP3: either Azami Green or mCherry. In these assays, the THP-1 cells were maintained as a continuous culture grown in suspension. The cells were incubated with iC3b, Apt[C3-GFP], and GFP or its derivatives (or a combination of any two components as controls) for 15 to 30 minutes. Live cells were washed extensively, and then examined under a microscope. In FIG. 9, fluorescent microscopic images of non-adherent THP-1 cells are shown at two different magnifications to show representative numbers of GFP-labeled cells and details of a single cell. In the experimental panels, cells treated with GFP, iC3b and Apt[C3-GFP] showed a strong signal for GFP in vesicles from multiple cells (more than 90% of the population). The control panels showed that in the absence of iC3b, only a weak and diffuse signal was detectable in cells. When Azami Green or mCherry was used in place of GFP, neither of these proteins produced fluorescent signals in THP-1 cells. Taken together, these controls confirmed that both the aptamer and the opsonin iC3b were necessary to generate the green fluorescent signal.

Example 8

Aptamer-Initiated Transportation of Extracellular GFP to Lysosomes

Figure 10A:
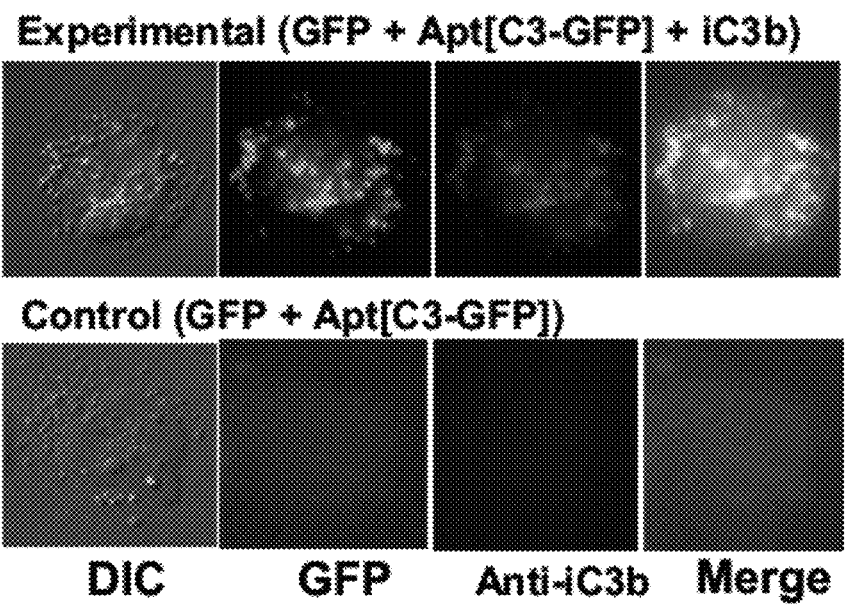
FIGS. 10A-B illustrate commandeering the C3 pathway for clearance and destruction of an opsonized particle.

To demonstrate that the triple complex (iC3b, Apt[C3-GFP], and GFP) was responsible for the specific uptake of GFP by the phagocytes, anti-iC3b antibody was used to localize and visualize iC3b molecules associated with the THP-1 cells. If the bi-functional aptamer functioned as a molecular adaptor, then GFP and iC3b should co-localize. Indeed, as shown in FIG. 10A, when the images with GFP signals and anti-iC3b signals were merged, perfect co-localization of the two signals was observed. To improve the quality of images for overlay in this experiment, fixed and permeabilized adherent THP-1 cells differentiated with 50 ng/ml phorbol myristate acetate were used. As mentioned before, these differentiated cells mimic native monocyte-derived macrophages in several aspects (Kohro et al., "A Comparison of Differences in the Gene Expression Profiles of Phorbol 12-myristate 13-acetate Differentiated THP-1 Cells and Human Monocyte-derived Macrophage," *J. Atherosclerosis Thromb* 11:88-97 (2004); Whatling et al., "Effect of Macrophage Differentiation and Exposure to Mildly Oxidized LDL on the Proteolytic Repertoire of THP-1 Monocytes," *J. Lipid Res.* 45:1768-1776 (2004), each of which is hereby incorporated by reference in its entirety).

Figure 10B:
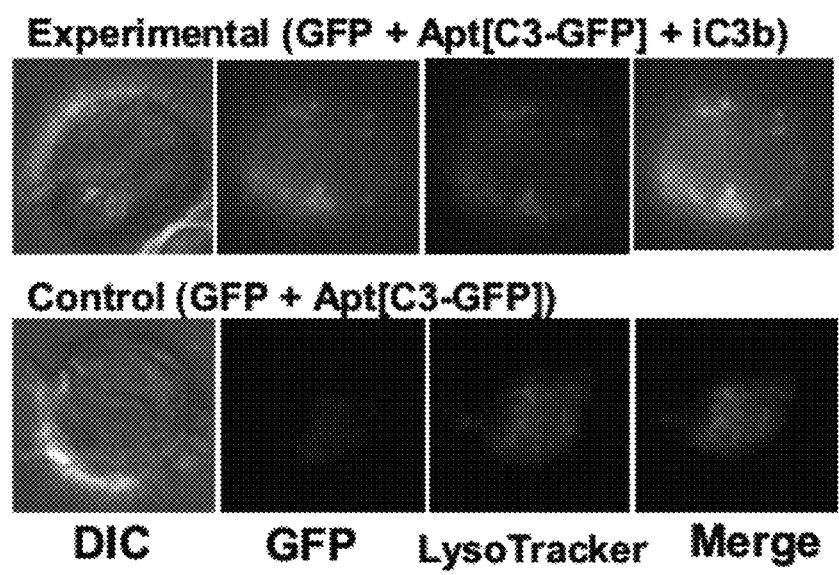

Particles are internalized by cells by means of two primary mechanisms. Small particles (<0.5 μm in diameter) such as macromolecules and viruses enter cells through receptor-mediated endocytosis, which is a clathrin-based mechanism. Large particles (>0.5 μm) are taken up into cells by actin-dependent phagocytosis (Aderem et al., "Mechanisms of phagocytosis in macrophages," *Annual Rev. Immunol.* 17:593-623 (1999), which is hereby incorporated by reference in its entirety). C3b receptors are involved in both types of internalization (Fearon et al., "Membrane Distribution and Adsorptive Endocytosis by C3b Receptors on Human Polymorphonuclear Leukocytes," *J. Exp. Med.* 153:1615-1628 (1981); Abrahamson et al., "Endocytosis of the C3b Receptor of Complement within Coated Pits in Human Polymorphonuclear Leukocytes and Monocytes," *Laboratory Investigation: A Journal of Technical Methods and Pathology,* 48:162-168 (1983), each of which is hereby incorporated by reference in its entirety). While the starting point of this pathway is the cell surface receptor that recognizes the opsonin, the end point is the lysosome. Upon successful commandeering of this pathway, GFP should be detected in the lysosomes. After incubation of the cells with iC3b, Apt[C3-GFP], and GFP, GFP fluorescence was concentrated in vesicle-like structures. To investigate the identity of these endosome-like structures, the same experimental setup for visualizing GFP was used with LysoTracker, an acidophilic dye, to visualize lysosomes. As shown in FIG. 10B, the merged image showed distinct co-localization of GFP with lysosomes.

Example 9

Degradation of Target Molecules in the *Lysosome*

The ultimate goal of using an aptamer-derived adaptor to commandeer the opsonization—phagocytosis pathway is to downregulate a target protein by directing it to the lysosome for degradation. However, GFP is a poor subject for investigation of the fate of target proteins after transport into lysosomes, because it is extremely stable inside cells (Cubitt et al., "Understanding, Improving and Using Green Fluorescent Proteins," *TIBS* 20:448-455 (1995), which is hereby incorporated by reference in its entirety), presumably due to its unique and compact β-can structure (Ormo et al., "Crystal Structure of the *Aequorea victoria* Green Fluorescent Protein," *Science* 273:1392-1395 (1996); Yang et al., "The Molecular Structure of Green Fluorescent Protein," *Nature Biotechnology* 14:1246-1251 (1996), each of which is hereby incorporated by reference in its entirety). While this feature allowed for tracking its pathway, even in the harsh environment of lysosomes, the fate of GFP after reaching lysosomes could not be generalized to other proteins, because GFP signals persisted for several days in THP-1 cells. To address this issue, the fate of two GFP derivatives were also investigated. These derivatives, d2EGFP and a GFP-mCherry fusion protein, were modified to degrade in a manner more like that of most other proteins.

Figure 11A:
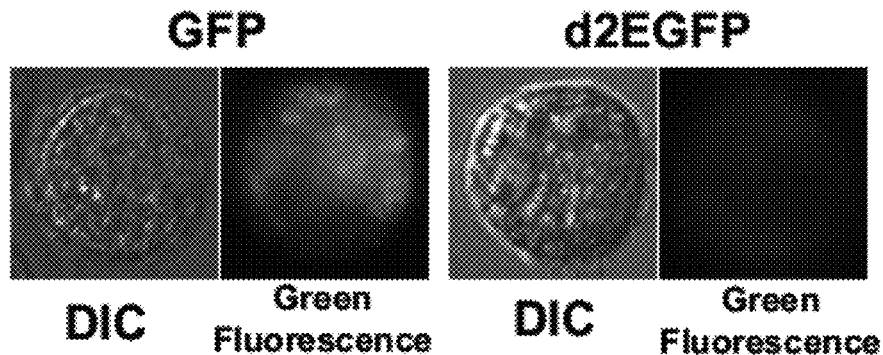
FIGS. 11A-B confirm degradation of target molecules by lysosomes.

The d2EGFP derivative is a destabilized variant of the enhanced GFP (eGFP) with residues 422-461 of mouse ornithine decarboxylase (MODC) fused to its C-terminus (Li et al., "Generation of Destabilized Green Fluorescent Protein as a Transcription Reporter," *J. Biol. Chem.* 273:34970-34975 (1998), which is hereby incorporated by reference in its entirety). This region of the MODC contains a PEST amino acid sequence that targets the protein for degradation and results in rapid protein turnover (Rechsteiner et al., "PEST Sequences and Regulation by Proteolysis," *TIBS* 21:267-271 (1996), which is hereby incorporated by reference in its entirety), so that degradation of d2EGFP correlates with decay of its fluorescent signal (L1 et al., "Generation of destabilized green fluorescent protein as a transcription reporter," *J. Biol. Chem.* 273:34970-34975 (1998), which is hereby incorporated by reference in its entirety). As shown in FIG. 8A, the AptGFP-AP3 component bound d2EGFP with affinity identical to that for GFP. In solution, the fluorescence of d2EGFP is comparable to that of GFP in the presence or absence of aptamer binding. However, when d2EGFP was used in the cell-based assay, the fluorescent signal was barely visible after incubation, suggesting a very short half-life for this protein after it was taken up by the cells (FIG. 11A).

Figure 11B:
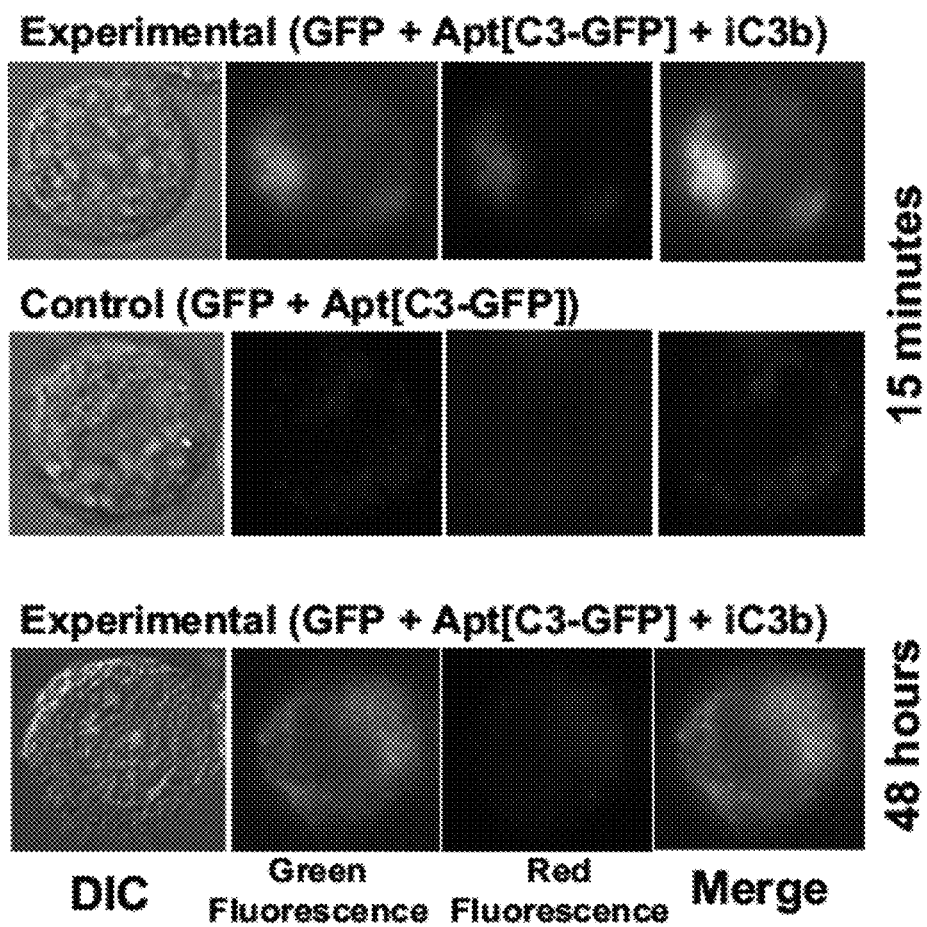

In the second derivative, the GFP-mCherry fusion protein, GFP is recognized by the aptamer but mCherry, an unrelated protein (Shaner et al., "Improved Monomeric Red, Orange and Yellow Fluorescent Proteins Derived from *Discosoma* sp. Red Fluorescent Protein," *Nature Biotechnology* 22:1567-1572 (2004), which is hereby incorporated by reference in its entirety), is not (FIG. 8A). The two fluorescent proteins are connected via a peptide linker and therefore function independently. The dual green and red fluorescent signals of GFP-mCherry afforded a much more specific test than d2GFP, whose signals quickly disappeared when used as the target for Apt[C3-GFP]. As shown in FIG. 11B, a gradual dissociation of the two types of fluorescent signals was observed during long incubation. Compared to the green signals, the red signals from mCherry became more diffuse and weaker as time elapsed, indicating that either the peptide linker had been severed or that mCherry was degraded faster than GFP.

Discussion of Examples 1-9

The above examples establish a mechanism to irreversibly downregulate target proteins and to potentially induce cytotoxicity to cancer cells using aptamer-mediated opsonization. This mechanism explores the physical-chemical fact that the probability of an effective interaction between two molecules decreases as a cube function of distance. As a result, a qualitative difference in reactivity may be mediated by mere proximity. Based on this principle, bi-functional aptamers were used to induce the proximity of a target molecule to the active forms of the complement C3. In this molecular configuration, C3b/iC3b acted as an opsonin and in effect tagged the target protein as "foreign" to cause its clearance or damage by phagocytes. Using GFP as a surrogate target, this principle was successfully proven. The composite bi-functional aptamer Apt[C3-GFP] made it possible to commandeer the opsonization-phagocytosis pathway to specifically transport extracellular GFP into the lysosome for degradation. The data presented above clearly demonstrated the formation of the iC3b.Apt[C3-GFP].GFP triple complex (FIG. 8C), the aptamer-mediated uptake of GFP by a large fraction of the phagocytic cells (FIG. 9), the transportation of GFP to lysosomes initiated by binding to the C3b receptor on phagocytes (FIGS. 10A-B), and the degradation of target molecules in the lysosome (FIGS. 11A-B).

The idea of conscripting the complement system in cancer immunotherapy was proposed more than 20 years ago (Cooper, "Complement and Cancer: Activation of the Alternative Pathway as a Theoretical Base for Immunotherapy," *Advances in Immunity and Cancer Therapy* 1:125-166 (1985), which is hereby incorporated by reference in its entirety), but then neglected for a long time as the major emphasis was placed, instead, on cell-mediated immune response against cancer. With the introduction of customized monoclonal antibodies (mAbs), the potential of complement to function as an effector system has been recognized once again (Gelderman et al., "Complement Function in mAb-mediated Cancer Immunotherapy," *Trends in Immunology* 25:158-164 (2004); Macor et al., "Complement as Effector System in Cancer Immunotherapy," *Immunology Letters* 111: 6-13 (2007), each of which is hereby incorporated by reference in its entirety). Complement has a number of advantages over other systems in that it is composed of molecules that can easily penetrate the tumor mass, and many of these molecules can be supplied locally by nearby cells. Human C3 is the most abundant complement protein in serum (1.2 mg/ml), and low levels of C3b/iC3b are constitutively available as part of the alternative pathway of complement activation involved in innate immune responses (Carroll, "The Role of Complement and Complement Receptors in Induction and Regulation of Immunity," *Annual Rev. Immunol.* 16:545-568 (1998), which is hereby incorporated by reference in its entirety). At any given time about 0.5% of the total C3 present in fresh human plasma is in its hydrolyzed form (Sahu et al., "Structure and Biology of Complement Protein C3, a Connecting Link Between Innate and Acquired Immunity," *Immunological Reviews* 180:35-48 (2001), which is hereby incorporated by reference in its entirety).

Normally, opsonization with antibodies or complement components facilitates removal of antigens from the circulation by macrophages in the liver and spleen, and by monocytes and neutrophils in other tissues (Tosi, "Innate Immune Responses to Infection," *J Allergy Clin. Immunol.* 116:241-249 (2005), which is hereby incorporated by reference in its entirety). C3b is preferentially cleared by the complement receptor CR1, and iC3b is preferentially cleared by CR3 (Yan et al., "Critical Role of Kupffer cell CR3 (CD11b/CD18) in the Clearance of IgM-opsonized Erythrocytes or Soluble Beta-glucan," *Immunopharmacology* 46:39-54 (2000), which is hereby incorporated by reference in its entirety). Enhancement of the immune response to targeted proteins via linkage to C3b has been demonstrated previously (Villiers et al., "Covalent Binding of C3b to Tetanus Toxin: Influence on Uptake/internalization of Antigen by Antigen-specific and Non-specific B Cells," *Immunology* 89:348-355 (1996); Villiers et al., "Amplification of the Antibody Response by C3b Complexed to Antigen Through an Ester Link," *J. Immunology* 162:3647-3652 (1999); Villiers et al., "Improvement of Long-lasting Response and Antibody Affinity by the Complexation of Antigen with Complement C3b," *International Immunology* 15:91-95 (2003), each of which is hereby incorporated by reference in its entirety). Bi-functional polyvalent aptamers with high affinity to both a target and C3b/iC3b will therefore promote clearance of the target by either CR1 or CR3. The examples presented above demonstrate the efficacy of this approach quite clearly. Moreover, the systematic design of additional bi-functional polyvalent aptamers directed to different target proteins of interest, particularly those associated with disease conditions such as cancer (e.g., VEGF), should achieve the same result: degradation of the target protein via opsonization.

If the target is on the surface of a cancer cell, bi-functional aptamers will increase the deposition of C3b/iC3b on the cell in the same manner as demonstrate above, and thereby help to induce or enhance complement-mediated cytotoxicity. C3b/iC3b deposited on tumor cells promotes adhesion of effector cells such as macrophages and NK cells through complement receptors, whereby cytotoxicity may ensue with the help of additional signals (Ross et al., "Therapeutic Intervention with Complement and Beta-glucan in Cancer," *Immunopharmacology* 42:61-74 (1999); Hong et al., "Beta-glucan Functions as an Adjuvant for Monoclonal Antibody Immunotherapy by Recruiting Tumoricidal Granulocytes as Killer Cells," *Cancer Res.* 63:9023-9031 (2003); Li et al., "Yeast beta-glucan Amplifies Phagocyte Killing of iC3b-opsonized Tumor Cells via Complement Receptor 3-Syk-phosphatidylinositol 3-kinase Pathway," *J. Immunol.* 177:1661-1669 (2006), each of which is hereby incorporated by reference in its entirety). While the inhibitory effect of membrane-bound complement regulatory proteins (mCRPs) that are often overexpressed on tumor cells may still provide a mechanism for these cells to evade complement attack (Jurianz et al., "Complement Resistance of Tumor Cells: Basal and Induced Mechanisms," *Mol. Immunol.* 36:929-939 (1999), which is hereby incorporated by reference in its entirety), this can be overcome through the blockade or overwhelming of these mCRPs to allow the efficient elimination of opsonized tumor cells (Gelderman et al., "Complement Function in mAb-mediated Cancer Immunotherapy," *Trends in Immunology* 25:158-164 (2004); Gelderman et al., "Inhibiting Complement Regulators in Cancer Immunotherapy with Bispecific mAbs," *Exp. Opin. Biol. Ther.* 5:1593-1601 (2005), each of which is hereby incorporated by reference in its entirety).

Example 10

Synthesis of Bi-functional Aptamer Targeting C3b/iC3b and VEGF

Because the bi-functional aptamers synthesized and utilized in Examples 1-9 contain natural RNA and would be degraded in vivo, the SELEX procedure will be repeated using 2' fluoro-pyrimidine RNA, which is resistant to degradation. This type of aptamer has improved stability in vivo with a half-life up to 80 hours in serum (Kubik et al., "Isolation and Characterization of 2'-Fluoro-, 2'-Amino-, and 2'-Fluoro-amino-Modified RNA Ligands to Human IFN-gamma that Inhibit Receptor Binding," *J. Immunol.* 159:259-267 (1997), which is hereby incorporated by reference in its entirety). In addition, rather than selecting aptamers that bind to C3 and its derivatives, aptamers specific for C3b and/or iC3b, but not C3, will be selected and then optimized in the manner described in the preceding examples. Because the isolation of aptamers for discrete sites on a protein has been previously demonstrated (Shi et al., "A Specific RNA Hairpin Loop Structure Binds the RNA Recognition Motifs of the *Drosophila* SR Protein B52," *Mol. Cell. Biol.* 17:1649-1657 (1997), which is hereby incorporated by reference in its entirety), this process is expected to involve no more than routine experimentation. The fluorescent functional assay established in the preceding examples will facilitate the screening of these aptamers.

After demonstrating the ability of the modified RNA aptamers to promote opsonization, bivalent aptamers that target VEGF will be formed by integrating known VEGF aptamers into the construct. Several 2'F-Py RNA based aptamers have been identified for VEGF-165 (Ruckman et al., "2'-Fluoropyrimidine RNA-based Aptamers to the 165-amino Acid Form of Vascular Endothelial Growth Factor (VEGF165) Inhibition of Receptor Binding and VEGF-induced Vascular Permeability Through Interactions Requiring the Exon 7-encoded Domain," *J. Biol. Chem.* 273:20556-20567 (1998), which is hereby incorporated by reference in its entirety). One of these has been further developed into the drug Macugen (pegaptanib sodium injection) to treat the wet form of age-related macular degeneration (AMD). This aptamer can also serve as a targeting aptamer in the bi-functional aptamer of the present invention.

Recombinant human VEGF purified from *E. coli* or modified human 293 cells is commercially available. Degradation of VEGF in aptamer-treated and control macrophage cultures will be evaluated by quantifying the clearance of purified VEGF added to macrophage (e.g., THP-1) cultures. The media will be collected and concentrated using trichloroacetic acid to precipitate total protein or affinity purification using heparin-sepharose beads, which will bind all forms of VEGF except VEGF120 (Robinson et al., "The Splice Variants of Vascular Endothelial Growth Factor (VEGF) and Their Receptors," *J. Cell Science* 114(Pt 5):853-865 (2001), which is hereby incorporated by reference in its entirety), and target degradation will be assayed using Western blot immunoassay. The dosage and time course for the degradation experiments will be empirically established.

After demonstrating the efficacy of the VEGF-bivalent aptamers for promoting opsonization of VEGF in vitro, the efficacy of these bivalent aptamers in xenograft animal cancer models will be assessed. Angiogenesis is a critical process in the progression of cancer from small, localized neoplasms to larger, growing, and potentially metastatic tumors. VEGF is the most potent and prominent cytokine responsible for endothelial cell differentiation, migration, proliferation, tube formation, and vessel assembly. A large and growing body of evidence shows that VEGF gene expression and VEGF production are associated with a range of solid tumor types and with poor prognosis (Shinkaruk et al., "Vascular Endothelial Cell Growth Factor (VEGF), An Emerging Target for Cancer Chemotherapy," *Current Med. Chem.* 3:95-117 (2003), which is hereby incorporated by reference in its entirety). These include bladder cancer, breast cancer, cervical cancer, colorectal cancer, esophageal cancer, glioblastoma multiforme, head and neck cancer, lung cancer, ovarian cancer, pancreatic cancer, prostate cancer, and renal cell carcinoma. VEGF is also expressed by certain cell lines derived from a wide variety of lymphomas and leukemias. Among different isoforms, VEGF-A is considered the most important form in tumor tissues. VEGF-165 is a heparin-binding glycoprotein and is the most abundant and active isoform of VEGF-A.

Example 11 iC3b Deposition on Cancer Cells and CR3-DCC

The proposed mechanism of aptamer-mediated opsonization of cancer cells using prostate cell lines will be demonstrated. An excellent prostate tumor cell marker is the prostate-specific membrane antigen ("PSMA"), for which aptamers have been identified in the form of 2'F-Py RNA (Lupold et al., "Identification and Characterization of Nuclease-stabilized RNA Molecules that Bind Human Prostate Cancer Cells Via the Prostate-specific Membrane Antigen," *Cancer Research* 62:4029-4033 (2002), which is hereby incorporated by reference in its entirety). PSMA expression is primarily prostate specific and elevated in malignant prostate cells. While malignant prostate cells express the full-length membrane bound form, normal cells predominantly express an alternatively spliced cytosolic form.

Using the 2' fluoro-pyrimidine RNA aptamers specific for C3b and/or iC3b, which will be synthesized and optimized as described in Example 10 above, the selected aptamers will be grafted to the known PMSA-specific 2'F-Py RNA aptamer to form a bi-functional aptamer of the present invention. This bi-functional aptamer will be capable of labeling prostate cancer cells for opsonization.

Prostate cancer cells lines that express PSMA (such as LNCaP) and cell lines that do not express PSMA (such as PC-3) will be used to test whether a bi-functional opsonizing aptamer targeting PSMA can increase the deposition of iC3b on cancer cells. Various amounts of bi-functional aptamers will be added into the culture media with fixed amount of purified iC3b. After incubation and washing, iC3b molecules on the cell surface will be detected and quantified using confocal microscopy by anti-human iC3b (neoantigen) monoclonal antibodies, which are commercially available.

Upon confirming that bi-functional aptamers can significantly increase iC3b deposition on tumor cells, it will subsequently be tested whether this can lead to cytotoxicity mediated by β-glucan-primed monocytes or neutrophils. As an initial test, the same set-up described above will be used by adding bi-functional aptamers and purified iC3b to the tumor cell lines. Meanwhile, THP-1 cells will be incubated with soluble β-glucan. The two types of cells at a ratio of 1:20 (tumor cell:effector cell) will be mixed and incubated for 12 hours. Cytotoxicity will be measured by a colorimetric assay to quantitate the release of the stable cytoplasmic enzyme lactate dehydrogenase (LDH).

The in vitro cellular cytotoxicity assay described above uses purified iC3b and the established tumor cell line THP-1 as effectors. While the components of this assay are easy to control, the assay may not faithfully recapitulate the in vivo situation. If increased iC3b deposition on the target tumor cells can be demonstrated, but not induction of cytotoxicity using this simplistic assay, the purified iC3b and the THP-1 cell line will be substituted with fresh human serum and isolated $CD14^+$ monocytes. Regarding β-glucan, there are several formulations prepared by different procedures. The major difference is their molecular size. A recent study showed that a 25-kDa fragment of β-glucan released by macrophage processing of the long parental compound binds to CR3 and elicits CR3-dependent cytotoxicity (Li et al., "Yeast Beta-glucan Amplifies Phagocyte Killing of iC3b-opsonized Tumor Cells Via Complement Receptor 3-Syk-phosphatidylinositol 3-kinase Pathway," *J. Immunol.* 177:1661-1669 (2006), which is hereby incorporated by reference in its entirety). For the in vitro studies described here, the neutral soluble glucan ("NSG") prepared from yeast will be used, which has a small molecular mass of 20 kDa or less. This type of β-glucan has been demonstrated to bind to a lectin domain within the C-terminal region of the CD11b subunit of CR3 (Thornton et al., "Analysis of the Sugar Specificity and Molecular Location of the Beta-glucan-binding Lectin Site of Complement Receptor Type 3 (CD11b/CD18)," *J. Immunology* 156:1235-1246 (1996), which is hereby incorporated by reference in its entirety).

Effective demonstration of in vitro results warrants study of the bi-functional PMSA-specific aptamer for its efficacy in the treatment of prostate cancer in an animal model. Both xenograft studies using PMSA⁺ prostate cancer cells and a dual Pten⁻/p27⁻ knockout model will be used to assess the efficacy of the bi-functional aptamer in the treatment of prostate cancer.

Example 12

Multi-functional Aptamer Constructs Specific for Heat Shock Protein-Mediated Uptake Heat shock proteins ("HSPs"), a class of proteins that protect cells against stress by preventing protein unfolding, were once believed to be solely intracellular proteins. They are now known to take soluble forms in which they play crucial roles in cross-presentation of antigens leading to induction of immune response. HSPs are taken up by internalizing receptors such as CD91, along with their peptide cargo, and also interact with signaling receptors such as the toll-like receptors TLR-2 and -4 (Calderwood et al., "Cell Surface Receptors for Molecular Chaperones," *Methods* 43(3):199-206 (2007), which is hereby incorporated by reference in its entirety).

HSPs are promising targets as molecules that can bridge aptamers specific for an HSP as well as another target protein with a receptor for uptake or signaling. The HSPs have been a focus of cancer therapy in an attempt to exploit their ability to induce cross-presentation of self antigens from tumors, which are known to contain many mutations that render them distinct from proteins expressed by normal cells (Parmiani et al., "Heat Shock Proteins and Their Use as Anticancer Vaccines," *Clin. Cancer Res.* 10(24):8142-6 (2004), which is hereby incorporated by reference in its entirety). In particular, an HSP-peptide complex using purified HSP-gp96 and peptides derived from patients' resected tumors was tested in patients with non-Hodgkin's lymphoma, which resulted in statistically significant but limited improvement of patient outcome (Oki et al., "Experience with Heat Shock Protein-peptide Complex 96 Vaccine Therapy in Patients with Indolent Non-Hodgkin Lymphoma," *Cancer* 109(1):77-83 (2007), which is hereby incorporated by reference in its entirety).

Example 13

Multi-Functional Aptamer Constructs Specific for MHC I and II receptors and/or CD1

Dendritic cells ("DCs") are immune system cells whose major role is to sample and take up material from the external environment by phagocytosis and receptor-mediated and non-receptor mediated endocytosis, break down the captured proteins into peptides, and present these peptides to T cells in order to provoke specific immune responses. Several subsets of DCs exist including interstitial, langherans, and plasmacytoid DCs, which express specific markers. Immature DCs are found in the bone marrow and the blood, and mature DCs reside in both lymphoid and non-lymphoid tissues. DCs have been manipulated in experimental immunotherapies to induce both enhanced immunity and immune tolerance. In mice, levels of infection with the parasitic organism *Leishmania donovani* were reduced when DCs overexpressing IL-12 were pulsed with *L. donovani* antigens and reintroduced. Rat bone marrow DCs pulsed with myelin basic protein and reinjected were able to induce tolerance of this protein in an experimental model of autoimmune disorders (Lipscomb et al., "Dendritic Cells: Immune Regulators in Health and Disease," *Physiological Reviews* 82(1):97-130 (2002), which is hereby incorporated by reference in its entirety). In a hypothetical example, blood drawn from patients infected with tuberculosis can be drawn and DCs removed based on affinity for their specific markers. These DCs can be pulsed with a multi-functional aptamer with binding sites for MHC I and II receptors and/or CD1, a non-polymorphic histocompatibility protein with affinity for hydrophobic antigens, as well as peptides derived from the mycobacterial antigen MPT64, in order to stimulate a more aggressive T-cell response to *M. tuberculosis* infection.

Example 14

Multi-Functional Aptamer Constructs Specific for Cancer Cell Markers for Diagnostics and Imaging Due to their low toxicity and immunogenicity, and also to the ability to predict their folding and interactions a priori, aptamers have an advantage over conventional and peptide or protein drugs in that aptamers for multiple targets can easily be combined and injected or otherwise introduced simultaneously. Patterns of expression of multiple cytokines have been identified as a signature of various cancers, including ovarian cancer, which is notoriously difficult to detect (Gorelik et al., "Multiplexed Immunobead-based Cytokine Profiling for Early Detection of Ovarian Cancer," *Cancer Epidemiology, Biomarkers and Prevention* 14(4):981-7 (2005), which is hereby incorporated by reference in its entirety).

A combination of several distinct multivalent aptamers with specificity for individual cytokines and NIR-emitting detector molecules can be developed to quantify cytokine levels as a means of detecting cancer in vivo. Similarly, multivalent aptamers with affinity for receptors overexpressed in cancer (for example, HER2/Neu) and for gold nanoparticles can be developed so as to couple in vivo imaging with a therapy such as laser-ablation of gold nanoparticles.

Example 15

Multi-Functional Aptamers for Screening Complement Activation Inhibitors

High throughput technologies for SELEX and drug discovery are being developed that make use of various modifications for labeling such as fluorophores and/or fluorophores in combination with quenching molecules for easy detection of binding (Blank et al., "Aptamers as Tools for Target Validation," *Current Opinion in Chemical Biology* 9(4):336-42 (2005), which is hereby incorporated by reference in its entirety). Aptamers similar to the tools already developed—the aptamers described herein that are specific for both GFP and C3b/iC3b—should be useful for the purpose of screening for small molecule inhibitors of complement activation.

Alternatively, by developing aptamers using high throughput methods, or by using a large library of aptamers of random sequence, a group of multivalent aptamers with affinity for HSP-gp96 can be engineered that can be combined with resected tumors of cancer patients and then injected to produce a heightened immune response to mutated proteins from the patient's own tumor.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A nucleic acid aptamer comprising:
a first domain that binds to a biologically active proteolytic product of complement protein C3 that is C3b, iC3b, or both thereof, wherein the first domain binds to a site on C3b or iC3b that is distinct of, respectively, a CR1 or CR3 receptor binding site on C3b or iC3b, wherein the first domain comprises a nucleotide sequence according to nucleotides 2-41 of SEQ ID NO: 9; and
a second domain that binds to a molecule different from the biologically active proteolytic product of complement protein C3.

2. The nucleic acid aptamer according to claim 1 further comprising:
a plurality of first domains that bind to the biologically active proteolytic product of complement protein C3; or
a plurality of second domains that bind to a molecule different from the biologically active proteolytic product of complement protein C3.

3. The nucleic acid aptamer according to claim 1, wherein the biologically active proteolytic product of complement protein C3 is one of C3b and iC3b.

4. The nucleic acid aptamer according to claim 1, wherein the molecule different from the biologically active proteolytic product of complement protein C3 is a target protein.

5. The nucleic acid aptamer according to claim 4, wherein the target protein is a cell surface protein.

6. The nucleic acid aptamer according to claim 4, wherein the target protein is an extracellular protein.

7. The nucleic acid aptamer according to claim 1 further comprising a near-infrared emitting probe conjugated to the aptamer.

8. A molecular complex comprising:
the nucleic acid aptamer according to claim 1; and
the biologically active proteolytic product of complement protein C3 bound to the nucleic acid aptamer at the first domain.

9. The molecular complex according to claim 8, wherein the biologically active proteolytic product of complement protein C3 is one of C3b and iC3b.

10. The molecular complex according to claim 8 further comprising:
a target protein bound to the nucleic acid aptamer at the second domain.

11. The molecular complex according to claim 10, wherein the target protein is a cell surface protein.

12. The molecular complex according to claim 11, wherein the cell surface protein is a cancer cell-specific surface protein.

13. The molecular complex according to claim 10, wherein the target protein is an extracellular protein.

14. The molecular complex according to claim 13, wherein the extracellular protein is VEGF.

15. The molecular complex according to claim 10, wherein the target protein is a fluorescent protein.

16. A cell comprising a target protein on its surface, wherein the target protein is a component of the molecular complex according to claim 10.

17. The cell according to claim 16, wherein the cell is a cancer cell.

18. A method of promoting opsonization of a cell, said method comprising:
providing a nucleic acid aptamer according to claim 1; and
contacting a cell surface protein on a cell with the aptamer, wherein the aptamer binds the target protein at the second domain and the biologically active proteolytic product of complement protein C3 at the first domain, thereby promoting opsonization of the cell.

19. The method according to claim 18, wherein the cell is a cancer cell and the cell surface protein is cancer cell-specific.

20. The nucleic acid aptamer according to claim 1 wherein the nucleic acid aptamer comprises 2'-fluoro RNA.

* * * * *